(12) United States Patent
Fu et al.

(10) Patent No.: US 12,103,968 B2
(45) Date of Patent: Oct. 1, 2024

(54) ANTIBODIES TO HUMAN ZNT8

(71) Applicant: THE JOHNS HOPKINS UNIVERSITY, Baltimore, MD (US)

(72) Inventors: Dax Fu, Short Hills, NJ (US); Chengfeng Merriman, Essex, MD (US)

(73) Assignee: The Johns Hopkins University, Baltimore, MD (US)

( * ) Notice: Subject to any disclaimer, the term of this patent is extended or adjusted under 35 U.S.C. 154(b) by 805 days.

(21) Appl. No.: 17/268,925

(22) PCT Filed: Aug. 16, 2019

(86) PCT No.: PCT/US2019/046747
§ 371 (c)(1),
(2) Date: Feb. 16, 2021

(87) PCT Pub. No.: WO2020/037174
PCT Pub. Date: Feb. 20, 2020

(65) Prior Publication Data
US 2021/0238279 A1    Aug. 5, 2021

Related U.S. Application Data

(60) Provisional application No. 62/719,016, filed on Aug. 16, 2018.

(51) Int. Cl.
C07K 16/28    (2006.01)
(52) U.S. Cl.
CPC .......... C07K 16/28 (2013.01); *C07K 2317/33* (2013.01); *C07K 2317/76* (2013.01); *C07K 2317/92* (2013.01)
(58) Field of Classification Search
None
See application file for complete search history.

(56) References Cited

U.S. PATENT DOCUMENTS

| 4,399,216 A | 8/1983 | Axel et al. |
| 4,634,665 A | 1/1987 | Axel et al. |

(Continued)

FOREIGN PATENT DOCUMENTS

| CN | 101646781 | 2/2010 |
| CN | 106084051 B | 9/2016 |

(Continued)

OTHER PUBLICATIONS

Abdiche et al "Determining Kinetics and Affinities of Protein Interactions Using a Parallel Real-time Label-free Biosensor the Octet," Analytical Biochemistry, 2008, 377:209-217.

(Continued)

*Primary Examiner* — Daniel E Kolker
*Assistant Examiner* — Hilary Ann Petrash
(74) *Attorney, Agent, or Firm* — Casimir Jones, S.C.

(57) ABSTRACT

The present invention relates to the fields of immunology and autoimmunity. More specifically, the present invention provides methods and compositions directed to the generation and use of antibodies to the pancreatic zinc transporter, ZnT8. The present invention also provides an isolated antibody or antigen-binding fragment thereof that specifically binds ZnT8 comprising a VH comprising one of the amino acid sequences set forth in SEQ ID NOS:2, 12, 22, 32, 42 and 52. In alternative embodiments an isolated antibody or antigen-binding fragment thereof that specifically binds ZnT8 comprises a VL comprising one of the amino acid sequences as set forth in SEQ ID NOS:7, 17, 27, 37, 47 and 57.

15 Claims, 10 Drawing Sheets

Specification includes a Sequence Listing.

(56) References Cited

U.S. PATENT DOCUMENTS

| | | |
|---|---|---|
| 4,880,935 A | 11/1989 | Thorpe |
| 5,122,368 A | 6/1992 | Greenfield et al. |
| 5,179,017 A | 1/1993 | Axel et al. |
| 5,225,539 A | 7/1993 | Winter |
| 5,399,363 A | 3/1995 | Liversidge et al. |
| 5,466,468 A | 11/1995 | Schneider et al. |
| 5,530,101 A | 6/1996 | Queen et al. |
| 5,543,158 A | 8/1996 | Greg et al. |
| 5,580,579 A | 12/1996 | Ruddy et al. |
| 5,585,089 A | 12/1996 | Queen et al. |
| 5,613,308 A | 3/1997 | Little |
| 5,622,929 A | 4/1997 | Willner et al. |
| 5,624,821 A | 4/1997 | Winter et al. |
| 5,629,001 A | 5/1997 | Michael et al. |
| 5,641,515 A | 6/1997 | Ramtoola |
| 5,641,640 A | 6/1997 | Hanning |
| 5,725,871 A | 3/1998 | Illum |
| 5,731,168 A | 3/1998 | Carter et al. |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 5,824,805 A | 10/1998 | King et al. |
| 5,834,597 A | 11/1998 | Tso et al. |
| 5,859,205 A | 1/1999 | Adair et al. |
| 5,869,046 A | 2/1999 | Presta et al. |
| 5,892,019 A | 4/1999 | Schlom et al. |
| 6,165,710 A | 12/2000 | Robinson |
| 6,214,345 B1 | 4/2001 | Firestone et al. |
| 6,407,213 B1 | 6/2002 | Carter et al. |
| 6,613,308 B2 | 9/2003 | Bartus et al. |
| 6,737,514 B1 | 5/2004 | Wang |
| 6,881,557 B2 | 4/2005 | Foote |
| 8,563,291 B2 | 10/2013 | Yoshimura et al. |
| 8,563,327 B2 | 10/2013 | Park et al. |
| 9,023,984 B2 | 5/2015 | Hutton et al. |
| 9,568,482 B2 | 2/2017 | Seve et al. |
| 9,810,697 B2 | 11/2017 | McKenna et al. |
| 11,016,085 B2 | 5/2021 | Fu |
| 11,078,251 B2 | 8/2021 | Mallone et al. |
| 11,510,996 B2 | 11/2022 | Pearson et al. |
| 11,841,363 B2 | 12/2023 | Fu |
| 11,892,457 B2 | 2/2024 | Fu et al. |
| 2009/0186364 A1 | 7/2009 | Yoshimura et al. |
| 2009/0191574 A1 | 7/2009 | Halperin |
| 2010/0068199 A1 | 3/2010 | Liang |
| 2010/0158909 A1 | 6/2010 | McDonagh et al. |
| 2012/0238572 A1 | 9/2012 | Su et al. |
| 2016/0025744 A1 | 1/2016 | Feldman et al. |
| 2017/0096497 A1 | 4/2017 | Weisbart |
| 2018/0243408 A1 | 8/2018 | Fanger et al. |
| 2019/0137485 A1 | 5/2019 | Fu |
| 2020/0132698 A1 | 4/2020 | Fu et al. |
| 2021/0154247 A1 | 5/2021 | Rottiers et al. |
| 2021/0263021 A1 | 8/2021 | Fu |
| 2021/0302413 A1 | 9/2021 | Fu et al. |
| 2022/0308052 A1 | 9/2022 | Fu et al. |

FOREIGN PATENT DOCUMENTS

| | | |
|---|---|---|
| CN | 106084043 | 11/2016 |
| CN | 106771233 | 5/2017 |
| EP | 404097 | 12/1990 |
| WO | WO 198705330 | 9/1987 |
| WO | WO 198912624 | 12/1989 |
| WO | WO 199311161 | 6/1993 |
| WO | 2008083331 A2 | 7/2008 |
| WO | WO 2008131224 | 10/2008 |
| WO | WO 2009064901 | 5/2009 |
| WO | WO 2012062697 | 5/2012 |
| WO | WO 2012173184 | 12/2012 |
| WO | WO 2013071055 | 5/2013 |
| WO | WO 2014142517 | 9/2014 |
| WO | WO 2014160175 | 10/2014 |
| WO | 2017189483 A1 | 11/2017 |
| WO | WO 2019014044 | 1/2019 |
| WO | WO 2020037174 | 2/2020 |
| WO | WO 2020247920 | 12/2020 |

OTHER PUBLICATIONS

Aplin et al., "Preparation, Properties, and Applications of Carbohydrate Conjugates of Proteins and Lipids," CRC Crit. Rev. Biochem., 1981, 10(4):259-306.

Arnon et al, "Monoclonal Antibodies for Immunotargeting of Drugs in Cancer Therapy," Monoclonal Antibodies and Cancer Therapy, 1986, pp. 243-256.

Arvan et al., "Islet autoantigens: structure, function, localization, and regulation," Cold Spring Harb Perspect Med, Aug. 2012, 2(8):a007658.

Barelle et al., "VNARs: An Ancient and Unique Repertoire of Molecules That Deliver Small, Soluble, Stable and High Affinity Binders of Proteins," Antibodies, 2015, 4(3):240-258.

Berge et al., "Pharmaceutical salts," J. Pharm. Sci. Jan. 1977, 66(1):1-19.

Better et al., "*Escherichia coli* secretion of an active chimeric antibody fragment," Science, May 1988, 240(4855):1041-1043.

Better et al., "Expression of Engineered Antibodies and Antibody Fragments in Microorganisms," Methods in Enzymology, 1989, 178:476-496.

Bindels et al., "mScarlet: a bright monomeric red fluorescent protein for cellular imaging," Nat Methods, 2017, 14:53-56.

Bird et al., "Single chain antibody variable regions," Trends in Biotechnology, Jan. 1991, 9:132-137.

Bird et al., "Single-chain antigen-binding proteins," Science, Oct. 1988, 242(4877):423-426.

Bloem et al., "The elusive role of B lymphocytes and islet autoantibodies in (human) type 1 diabetes," Diabetologia, Jul. 2017, 60(7):1185-1189.

Bonner-Weir et al., "New perspectives on the microvasculature of the islets of Langerhans in the rat," Diabetes, Oct. 1982, 31(10):883-889.

Carter et al., "High Level *Escherichia coli* Expression and Production of a Bivalent Humanized Antibody Fragment," Bio/Technology, Feb. 1992, 10:163-167.

Chimienti, "Zinc, pancreatic islet cell function and diabetes: new insights into an old story," Nutr Res Rev, Jun. 2013, 26(1):1-11.

Cieslak et al., "Role of proinflammatory cytokines of pancreatic islets and prospects of elaboration of new methods for the diabetes treatment," Acta Biochim Pol, 2015, 62(1):15-21.

Co et al., "A humanized antibody specific for the platelet integrin gpIIb/IIIa," J Immunol, 1994, 152(6):2968-2976.

Corbin et al., "A Practical Guide to Rodent Islet Isolation and Assessment Revisited," Biol Proced Online, 2021, 23:7.

Darling et al., "Kinetic exclusion assay technology: characterization of molecular interactions," Assay and Drug Dev Tech, 2004, 2:647-657.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol, 2002, 169(6):3076-3084.

Dodson et al., "The role of assembly in insulin's biosynthesis," Curr Opin Struct Biol., Apr. 1998, 8(2):189-194.

Donath et al., "Type 2 diabetes as an inflammatory disease," Nat Rev Immunol, 2011, 11:98-107.

Dubowchik et al., "Receptor-mediated and enzyme-dependent targeting of cytotoxic anticancer drugs," Pharm. Therapeutics, Aug. 1999, 83(2):67-123.

Dwivedi et al., "Loss of ZnT8 function protects against diabetes by enhanced insulin secretion," Nat Genet, 2019, 51:1596-1606.

Edge et al., "Deglycosylation of glycoproteins by trifluoromethanesulfonic acid," Anal. Biochem., Nov. 1981, 118(1):131-137.

El-Gohary et al., "Three-dimensional analysis of the islet vasculature," Anat Rec, 2012, 295(9):1473-1481.

(56) References Cited

OTHER PUBLICATIONS

Eriksson et al., "Pancreatic imaging using an antibody fragment targeting the zinc transporter type 8: a direct comparison with radio-iodinated Exendin-4," Acta Diassbetol, 2018, 55(1):49-57.
Extended European Search Report in European Application No. 19849457.7, dated Jul. 13, 2022, 14 pages.
Fukuda et al., "In vitro evolution of single-chain antibodies using mRNA display," Nucleic Acids Res., Oct. 2006, 34(19):e127.
Garner et al., "Na,K-ATPase in the nuclear envelope regulates Na+: K+ gradients in hepatocyte nuclei," J Membr Biol, 2002, 187:97-115.
Ghazalpour et al., "Comparative analysis of proteome and transcriptome variation in mouse," PLoS Genet, 2011, 7:e1001393.
Ghetie et al., "Multiple roles for the major histocompatibility complex class I—related receptor FcRn," Annu. Rev. Immunol., 2000, 18:739-766.
Ghetie et al., "Transcytosis and catabolismof antibody," Immunol. Res., 2002, 25(2):97-113.
Gu et al., "Novel autoantibodies to the beta-cell surface epitopes of ZnT8 in patients progressing to type-1 diabetes," J Autoimmun, Aug. 2021, 122:102677.
Hahn et al., "3D imaging of human organs with micrometer resolution—applied to the endocrine pancreas," Commun Biol, Sep. 2021, 4(1):1063.
Hara et al., "Transgenic mice with green fluorescent protein-labeled pancreatic beta—cells," Am J Physiol Endocrinol Metab, Jan. 2003, 284(1):E177-183.
Hieter et al., "Evolution of human immunoglobulin kappa J region genes.," J. Biol. Chem., Feb. 1982, 257(3):1516-1522.
Hinton et al., "Engineered human IgG antibodies with longer serum half-lives in primates," J. Biol. Chem., Feb. 2004, 279(8):6213-6216.
Ho et al, Gene, "Site-directed mutagenesis by overlap extension using the polymerase chain reaction." Apr. 1989, 77(1):51-59.
Holliger et al., "'Diabodies': small bivalent and bispecific antibody fragments," Proc. Natl. Acad. Sci. U S A., Jul. 1993, 90:6444-6448.
Hudson, et al., "High avidity scFv multimers; diabodies and triabodies," J Immunol. Methods, Dec. 1999, 231(1-2):177-189.
Huston et al., "Protein engineering of antibody binding sites: recovery of specific activity in an anti-digoxin single-chain Fv analogue produced in Escherichia coli," Proc. Natl. Acad. Sci. U S A., Aug. 1988, 85:5879-5883.
Ionescu-Tirgoviste et al., "A 3D map of the islet routes throughout the healthy human pancreas," Sci Rep, 2015, 5:14634.
Iwahashi et al., "CDR substitutions of a humanized monoclonal antibody (CC49): contributions of individual CDRs to antigen binding and immunogenicity," Mol. Immunol., 1999, 36:1079-1091.
Jefferis et al., "Human immunoglobulin allotypes: possible implications for immunogenicity," Mabs, 2009, 1(4):332-338.
Jermutus et al., "Tailoring in vitro evolution for protein affinity or stability," Proc. Natl. Acad. Sci. USA, Dec. 2000, 98:75-80.
Johne et al., "Epitope mapping and binding kinetics of monoclonal antibodies studied by real time biospecific interaction analysis using surface plasmon resonance," J. Immunol. Methods, Apr. 1993, 160(2):191-198.
Johnson et al., "Anti-tumor activity of CC49-doxorubicin immunoconguates," Anticancer Res. 1995, 15:1387-93.
Kambe et al., "Zinc transporters and their functional integration in mammalian cells," J Biol Chem, 2021, 100320.
Kaufman et al., "Amplification and expression of sequences cotransfected with a modular dihydrofolate reductase complementary dna gene," J Mol. Biol. 1982, 159(4):601-621.
Kim et al., "In situ quantification of pancreatic beta-cell mass in mice," J Vis Exp., 2010, 40:1-4.
Lamoyi, "Preparation of F(ab')2 fragments from mouse IgG of various subclasses," Methods in Enzymology, 1989, 121:652-663.
Lau et al., "Conjugation of doxorubicin to monoclonal anti-carcinoembryonic antigen antibody via novel thiol-directed cross-linking reagents," Bioorg-Med-Chem., 1995, 3(10):1299-1304.
Lau et al., "Novel doxorubicin-monoclonal anti-carcinoembryonic antigen antibody immunoconjugate activity in vitro," Bioorg-Med-Chem., 1995, 3(10):1305-12.
Lazar et al., "Engineered antibody Fc variants with enhanced effector function," Proc. Natl. Acad. Sci. USA, 2006, 103(11):4005-4010.
Lebowitz et al., "Modem analytical ultracentrifugation in protein science: a tutorial review," Protein Science, 2002, 11(9):2067-2079.
Lei et al., "Characterization of the Erwinia carotovora pelB gene and its product pectate lyase," J. Bacteriol., Sep. 1987, 169(9):4379-4383.
Lernmark et al., "Islet-cell-surface antibodies in juvenile diabetes mellitus," N Engl J Med, 1978, 299:375-380.
Lippow et al., "Computational design of antibody-affinity improvement beyond in vivo maturation," Nat. Biotechnol., 2005, 25(10):1171-1176.
Liston et al., "Beta-Cell Fragility as a Common Underlying Risk Factor in Type 1 and Type 2 Diabetes," Trends Mol Med, 2017, 23:181-194.
Lukowiak et al., "Identification and purification of functional human beta-cells by a new specific zinc-fluorescent probe," J Histochem Cytochem, Apr. 2001, 49(4):519-528.
Lund et al., "Human Fc gamma RI and Fc gamma RII interact with distinct but overlapping sites on human IgG," J Immun., Oct. 1991, 147(8):2657-2662.
Mattila et al, "Extensive allelic sequence variation in the J region of the human immunoglobulin heavy chain gene locus," Eur. J. Immunol., 1995, 25:2578-2582.
Merriman et al., "Down-regulation of the islet-specific zinc transporter-8 (ZnT8) protects human insulinoma cells against inflammatory stress," J Biol Chem, 2019, 294:16992-17006.
Merriman et al., "Highly specific monoclonal antibodies for allosteric inhibition and immunodetection of the human pancreatic zinc transporter ZnT8," J Biol Chem, 2018, 293:16206-16216.
Merriman et al., "Lipid-tuned Zinc Transport Activity of Human ZnT8 Protein Correlates with Risk for Type-2 Diabetes," J Biol Chem, 2016, 291(53):26950-26957.
Milenic et al, "Construction, Binding Properties, Metabolism, and Tumor Targeting of a Single-Chain Fv Derived from the Pancarcinoma Monoclonal Antibody CC49," Cancer Research, 1991, 51:6363-6371.
Millstein et al., "Hybrid hybridomas and their use in immunohistochemistry," Nature, Oct. 1983, 305:537-539.
Mizushima et al., "pEF-BOS, a powerful mammalian expression vector," Nucleic Acids Res., 1990, 18:5322.
Morgan et al., "The N-terminal end of the CH2 domain of chimeric human IgG1 anti-HLA-DR is necessary for C1q, Fc gamma RI and Fc gamma RIII binding," Immunology, 1995, 86(5):319-24.
Morton et al., "Kinetic analysis of macromolecular interactions using surface plasmon resonance biosensors," Methods in Enzymology, 1998 295:268-294.
Mulligan et al., "Synthesis of rabbit β-globin in cultured monkey kidney cells following infection with a SV40 β-globin recombinant genome," Nature, 1979, 277:108-114.
Muratore et al., "The vascular architecture of the pancreatic islets: a homage to August Krogh," Comp Biochem Physiol a Mol Integr Physiol, 2021, 252:110846.
Neumann et al., "Gene transfer into mouse lyoma cells by electroporation in high electric fields, " EMBO J. 1982, 1(7):841-845.
Neville et al, "Enhancement of Immunotoxin Efficacy by Acid-cleavable Cross-linking Agents Utilizing Diphtheria Toxin and Toxin Mutants," Journal of Biological Chemistry., 1989, 264(25):14653-14661.
Noguchi et al., "Pharmacokinetic prediction of an antibody in mice based on an in vitro cell-based approach using target receptor-expressing cells," Sci Rep, 2020, 10:16268.
Ovacik et al., "Tutorial on Monoclonal Antibody Pharmacokinetics and Its Considerations in Early Development," Clin Transl Sci, 2018, 11:540-552.
Pantoliano et al, "Conformational stability, folding, and ligand-binding affinity of single-chain Fv immunoglobulin fragments expressed in Escherichia coli," Biochemistry, 1991, 30(42):10117-10125.

(56) References Cited

OTHER PUBLICATIONS

PCT International Preliminary Report on Patentability in International Application No. PCT/US2019/046747, dated Feb. 16, 2021, 7 pages.
PCT International Search Report and Written Opinion in International Application No. PCT/US2019/046747, dated Nov. 28, 2019, 8 pages.
Peterson et al., "A long-lived IL-2 mutein that selectively activates and expands regulatory T cells as a therapy for autoimmune disease," J Autoimmun, 2018, 95:1-14.
Pierce et al., "Isothermal Titration Calorimetry of Protein-Protein Interactions," Methods, 1999, 19:213-221.
Pluckthun et al., "Expression of functional antibody Fv and Fab fragments in *Escherichia coli*," Methods in Enzymology, 1989, 178:497-515.
Qian et al., "Screening and identification of human ZnT8-specific single-chain variable fragment (scFv) from type 1 diabetes phage display library," Science China Life Sciences, Jun. 2016, 59(7):686-693.
Rajpal et al., "A general method for greatly improving the affinity of antibodies by using combinatorial libraries," PNAS, 2005, 102(24):8466-71.
Roep et al., "Type 1 diabetes mellitus as a disease of the beta-cell (do not blame the immune system?," Nat Rev Endocrinol, 2021, 17(3):150-161.
Rousseaux et al., "Optimal conditions for the preparation of proteolytic fragments from monoclonal IgG of different rat IgG subclasses," Methods in Enzymology, 1989, 121:663-669.
Saunders et al., "Ectonucleoside Triphosphate Diphosphohydrolase-3 Antibody Targets Adult Human Pancreatic beta Cells for In Vitro and In Vivo Analysis," Cell Metab, Mar. 2019, 29(3):745-754.e4.
Schwanhausser et al., "Global quantification of mammalian gene expression control," Nature, 2011, 473:337-342.
Shields et al, "High resolution mapping of the binding site on human IgG1 for Fc gamma RI, Fc gamma RII, Fc gamma RIII, and FcRn and design of IgG1 variants with improved binding to the Fc gamma R," High resolution mapping of the binding site on human IgG1 for Fc gamma RI, Fc gamma RII, Fc gamma RIII, and FcRn and design of IgG1 variants with improved binding to the Fc gamma R, J. Biol. Chem., 2001, 276(9):6591-604.
Shin et al, "Physical map of the 3' region of the human immunoglobulin heavy chain locus: clustering of autoantibody-related variable segments in one haplotype," EMBO J. 1991, 10:3641-3645.
Sjolander et al., "Integrated fluid handling system for biomolecular interaction analysis," Anal. Chem, 1991, 63:2338-2345.
Sojar et al., "A chemical method for the deglycosylation of proteins," Arch. Biochem. Biophys., Nov. 1987, 259(1):52-57.
Stull et al., "Mouse islet of Langerhans isolation using a combination of purified collagenase and neutral protease," J Vis Exp., Sep. 2012, 67:4137.
Sun et al., "Gene silencing of ZnT8 attenuates inflammation and protects pancreatic tissue injury in T1D," Immunology Letters, Jun. 2018, 198:1-6.
Surface Plasmons on Smooth and Rough Surfaces and on Gratings, Springer Verlag, 1988, 140 pages.
Szabo et al., "Surface plasmon resonance and its use in biomolecular interaction analysis (BIA)," Curr. Opin. Struct. Biol. Oct. 1995, 5(5):699-705.
Takkinen et al, "An active single-chain antibody containing a cellulase linker domain is secreted by *Escherichia coli*," Protein Engineering, 1991, 4:837-841.
Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000, 164(3):1432-1441.
Thomas et al., "The natural autoantibody repertoire of nonobese diabetic mice is highly active," J Immunol, 2002, 169(11):6617-6624.
Thorpe et al., "New Coupling Agents for the Synthesis of Immunotoxins Containing a Hindered Disulfide Bond with Improved Stability in Vivo," Cancer Res., 1987, 47(22):5924-5931.
Thorpe et al., "The preparation and cytotoxic properties of antibody-toxin conjugates," Immunol. Rev., 1982, 62:119-58.
Thorpe, "Antibody Carriers of Cytotoxic Agents in Cancer Therapy: a Review," in Monoclonal Antibodies '84: Biological and Clinical Applications, Pinchera et al., eds., 1984, pp. 475-512.
Thorp-Greenwood et al., "Multimodal radio- (PET/SPECT) and fluorescence imaging agents based on metallo-radioisotopes: current applications and prospects for development of new agents," Dalton Trans, 2011, 40(23):6129-6143.
Thotakura et al., "Enzymatic deglycosylation of glycoproteins," Meth. Enzymol., 1987, 138:350-359.
Tozzoli, "Receptor autoimmunity: diagnostic and therapeutic implications," Auto Immun Highlights, 2020, 11:1.
Urlaub et al., "Isolation of Chinese hamster cell mutants deficient in dihydrofolate reductase activity," Proc. Natl. Acad. Sci. USA, 1980, 77:4216-4220.
Ustinova et al., "Characterization of monoclonal ZnT8-specific antibody," Frontiers in Immunology, Jan. 2013, retrieved from URL<https://internal-www.frontiersin.org/Community/AbstractDetails.aspx?ABS_DOI=10.3389/conf.fimmu.2013.02.00326&eid=&sname=>, 2 pages.
Vajdos et al., "Comprehensive functional maps of the antigen-binding site of an anti-ErbB2 antibody obtained with shotgun scanning mutagenesis," Journal of Molecular Biology, Jul. 2002, 320(2): 415-428.
Wan et al., "Proteoliposome-based full-length ZnT8 self-antigen for type 1 diabetes diagnosis on a plasmonic platform," Proc Natl Acad Sci U S A, 2017, 114:10196-10201.
Ward et al., "Binding activities of a repertoire of single immunoglobulin variable domains secreted from *Escherichia coli*," Nature, Oct. 1989, 341:544-546.
Wigler et al., "Biochemical transfer of single-copy eucaryotic genes using total cellular DNA as donor," Cell, 1978, 14(3):725-731.
Wijesekara et al., "Beta cell-specific Znt8 deletion in mice causes marked defects in insulin processing, crystallisation and secretion," Diabetologia, Aug. 2010, 53(8):1656-1668.
Winkel et al., "Islet cell surface antibodies from insulin-dependent diabetics bind specifically to pancreatic B cells," J Clin Invest, 1982, 70(1):41-49.
Xue et al., "Cryo-EM structures of human ZnT8 in both outward- and inward-facing conformations," Elife, 2020, 9:e58823.
European Search Report in European Application No. 20817829.3, dated Jun. 1, 2023, 20 pages.
Gu et al., "Identification of Autoantibodies to ZnT8 Extracellular Epitope(s) in Patients with T1D," Diabetes, 79th Scientific Sessions of the American-Diabetes-Association (ADA), Jun. 7-11, 2019, 68(Suppl. 1):162-OR.
Extended European Search Report in European Application No. 18832105.3, dated Mar. 11, 2021, 11 pages.
GenBank Accession No. NM_001172814.1, "*Homo sapiens* solute carrier family 30 (zinc transporter), member 8 (SLC30A8), transcript variant 2, mRNA," dated Mar. 15, 2015, 5 pages.
Hwang et al., "Budding yeast Cdc20: a target of the spindle checkpoint," Science, Feb. 1998, 279(5353):1041-1044 (abstract only).
International Preliminary Report on Patentability in International Appln. No. PCT/US2018/040890, dated Jan. 14, 2020, 6 pages.
International Search Report and Written Opinion in International Appln. No. PCT/US2018/040890, mailed Oct. 25, 2018, 8 pages.
International Search Report and Written Opinion in International Appln. No. PCT/US2022/075156, mailed Jan. 10, 2023, 13 pages.
Koh et al., "Visible to Near-Infrared Fluorescence Enhanced Cellular Imaging on Plasmonic Gold Chips," small, Jan. 27, 2016, 12(4):457-465 (abstract only).
Akerfeldt et al., "Cytokine-induced beta-cell death is independent of endoplasmic reticulum stress signaling," Diabetes, 2008, 57(11):3034-3044.
Atkinson et al., "How does type 1 diabetes develop?: the notion of homicide or beta-cell suicide revisited," Diabetes, 2011, 60(5):1370-1379.

(56) References Cited

OTHER PUBLICATIONS

Barlow et al., "Novel insights into pancreatic beta-cell glucolipotoxicity from real-lime functional analysis of mitochondrial energy metabolism in INS-1E insulinoma cells," Biochem J, 2013, 456(3):417-426.

Benton et al., "Screening lambdagt recombinant clones by hybridization to single plaques in situ," Science, Apr. 1977, 196(4286):180-182.

Bodganov et al., "Lipids and topological rules governing membrane protein assembly," Biochim. Biophys. Acta, 2014, 1843(8):1475-1488.

Brenner et al., "Encoded combinatorial chemistry," Proc. Natl. Acad. Sci. USA. Jun. 1992, 89(12):5381-5383.

Burbelo et al., "Luciferase Immunoprecipilalion Systems for Measuring Antibodies in Autoimmune and nfectious Diseases," Transl Res, 2015, 165:325-335.

Busch et al., "Increased fatty acid desaturation and enhanced expression of stearoyl coenzyme A desaturase protects Jancreatic beta-cells from lipoapoptosis," Diabetes, 2005, 54(10):2917-2924.

Butcher et al., "Association of proinflammatory cytokines and islet resident leucocytes with islet dysfunction in type 2 dliabetes," Diabetologia, 2014, 57(3):491-501.

Carell et al., "New promise in combinatorial chemistry: synthesis, characterization, and screening of small-molecule libraries in solution," Chem. Biol. 1995, 2(3):171-183.

Chabosseau et al., "Mitochondrial and ER-targeted eCALWY probes reveal high levels of free Zn2+," ACS Chem Biol, 2014, 9:2111-2120.

Chabosseau et al., "Zinc and diabetes, Arch Biochem Biophys," 2016, 611:79-85.

Chao et al., "Kinetic Study of the Antiport Mechanism of an *Escherichia coli* Zinc Transporter, ZitB," J Biol Chem, 2004, 279(13):12043-12050.

Cheng et al., "Prokaryotic Expression of Bioactive Zinc Transporter 8 Antigens and Detection of Diabetes Specific Autoantibodies in a Single Dot Immunogold Filtration Assay," Clin Lab, 2015, 10:1445-1452.

Cheng et al., "Tumor necrosis factor alpha-induced protein-3 protects zinc transporter 8 against proinflammatory cytokine-induced downregulation," Exp Ther Med, 2016, 12:1509-1514.

Cnop et al., "Mechanisms of pancreatic beta-cell death in type 1 and type 2 diabetes: many differences, few imilarities," Diabetes, 2005, 54(Suppl 2):S97-107.

Cwirla et al., "Peptides on phage: a vast library of peptides for identifying ligands," Biochemistry 1990, 87(16):6378-6382.

Darmon et al., "Oriented reconstitution of red cell membrane proteins and assessment of their transmembrane :lisposition by immunoquenching of fluorescence," Biochimica et Biophysica Acta, 1985, 817:238-248.

Davidson et al., "Zinc transporter 8 (ZnT8) and beta cell function," Trends Endocrinol Metab, 2014, 25(8):415-424.

Delic-Sarac et al., "ELISA Test for Analyzing of Incidence of Type 1 Diabetes Autoantibodies (GAD and A2) in Children and Adolescents," Acta Inform Med, 2016, 24:61-65.

Dudek et al., "Constitutive and inflammatory immunopeptidome of pancreatic beta-cells," Diabetes, 2012, 61(11):3018-3025.

Egefjord et al., "Zinc transporter gene expression is regulated by pro-inflammatory cytokines: a potential role for inc transporters in beta-cell apoptosis?" BMC Endocr Disord, 2009, 7(9).

Eide, "The oxidative stress of zinc deficiency," Metallomics, 2011, 3(11):1124-1129.

Eizirik et al., "The role of inflammation in insulitis and beta-cell loss in type 1 diabetes," Nat Rev Endocrinol, 2009, 5(4):219-226.

El Muayed et al., "Acute cytokine-mediated downregulation of the zinc transporter ZnT8 alters pancreatic beta-cell unction," J Endocrinol, 2010, 206 (2):159-169.

Enee et al., "ZnTB is a major COB+ T cell-recognized autoantigen in pediatric type 1 diabetes, Diabetes," 2012, 61(7):1779-1784.

Fabregat et al., "The Reactome Pathway Knowledgebase," Nucleic Acids Res, 2018, 46(D1):D649-D655.

Farino et al., "Development of a Rapid Insulin Assay by Homogenous Time-Resolved Fluorescence," PLoS One, 2016, 11(2):e0148684.

Felder, "The Challenge of Preparing and Testing Combinatorial Compound Libraries in the Fast Lane, at the Front end of Drug Development,," Chimia 1994, 48:512-541.

Ferrannini et al., "Progression to diabetes in relatives of type 1 diabetic patients: mechanisms and mode of onset," Diabetes, 2010, 59(3):679-685.

Flannick et al., "Exome sequencing of 20,791 cases of type 2 diabetes and 24,440 controls," Nature, 2019, 570(7759):71-76.

Fonseca et al., "Endoplasmic reticulum stress in beta-cells and development of diabetes," Curr Opin Pharmacol, 2009, 9(6):763-770.

Fred et al., "Role of the AMP kinase in cytokine-induced human EndoC-belaH1 cell death, Mol Cell Endocrinol," 2015, 414:53-63.

Gallop et al, "Applications of combinatorial technologies to drug discovery. 1. Background and peptide combinatorial libraries," J. Med. Chem., 1994, 37(9):1233-1251.

Geertsma et al., "Membrane reconstitution of ABC transporters and assays of translocator function," Nature Protocols, 2008, 3(2):256-266.

Gordon et al., "Applications of Combinatorial Technologies to Drug Discovery. 2. Combinatorial Organic Synthesis, Library Screening Strategies, and Future Directions," J Med. Chern. 1994, 37(10):1385-1401.

Grunstein et al., "Colony hybridization: a method for the isolation of cloned DNAs that contain a specific gene," Proc. Nat. Acad. Sci. USA, 1975, 72(10):3961-3965.

Gupta et al., "Visualizing the kinetic power stroke that drives proton-coupled zinc(II) transport," Nature, 2014, 512:101-104.

Gurgul-Convey et al., "Sensitivity profile of the human EndoC-betaH1 beta cell line to proinflammatory cytokines," Diabetologia, 2016, 59(10):2125-2133.

Hakonen et al., "MANF protects human pancreatic beta cells against stress-induced cell death," Diabetologia, 2018, 61(10):2202-2214.

Homma et al., "SOD1 as a molecular switch for initiating the homeostatic ER stress response under zinc deficiency," Mol Cell, 2013, 52(1):75-86.

Hotamisligil et al., "Inflammation, metaflammation and immunometabolic disorders," Nature, 2017, 542(7640):177-185.

Houghten et al., "Generation and use of synthetic peptide combinatorial libraries for basic research and drug discovery," Nature, 1991, 354:84-86.

Houghten, "Peptide libraries: criteria and trends," Trends Genet, 1993, 9:235-239.

Huang, "Zinc and its transporters, pancreatic beta-cells, and insulin metabolism," Vitarn Horm, 2014, 95:365-390.

Ilonen et al., "Patterns of beta-cell autoantibody appearance and genetic associations during the first years of life," Diabetes, 2013, 32(10):3636-3640.

International Preliminary Report on Patentability in International Application No. PCT/US2020/036625, dated Dec. 7, 2021, 5 pages.

International Search Report and Written Opinion in International Application No. PCT/US2020/036625, dated Sep. 17, 2020, 7 pages.

Jaraosz-Chobot et al., "Rapid increase in the incidence of type 1 diabetes in Polish children from 1989 to 2004, and predictions for 2010 to 2025," Diabetologia, 2011, 54:508-515.

Jarchum et al., "In vivo cytotoxicity of insulin-specific COB+ Tcells in HLA-A*0201 transgenic NOD mice," Diabetes, 2007, 56(10):2551-2560.

Kawasaki, "ZnT8 and type 1 diabetes," Endocrine Journal, 2012, 59(7):531-537.

Kay et al., "Overexpression of class I major histocompatibility complex accompanies insulitis in the nonobese :liabetic mouse and is prevented by anti-interferon-gamma antibody," Diabetologia, 1991, 34(11):779-785.

Kharroubi et al., "Free fatty acids and cytokines induce pancreatic beta-cell apoptosis by different mechanisms: role of nuclear factor-kappaB and endoplasmic reticulum stress," Endocrinology, 2004, 145(11):5087-5096.

(56) References Cited

OTHER PUBLICATIONS

Kimmel, "Identification and characterization of specific clones: strategy for confirming the validity of presumptive lones," Methods in Enzymology, 1987, 152:507.
Klingensmith et al., "The presence of GAD and IA-2 antibodies in youth with a type 2 diabetes phenotype: results from the TODAY study," Diabetes Care., 2010, 33:1970-1975.
Kodama et al., "Expression-Based Genome-Wide Association Study Links Vitamin D-Binding Protein With A\utoantigenicity in Type 1 Diabetes," Diabetes, 2016, 65(5):1341-1349.
Lam et al., "A new type of synthetic peptide library for identifying ligand-binding activity," Nature, 1991, 354:82-84.
Leahy et al., "Chronic hyperglycemia is associated with impaired glucose influence on insulin secretion. A study in normal rats using chronic in vivo glucose infusions," J Clin Invest, 1986, 77(3):908-915.
Lebl et al., "One-Bead-One-Structure Cornbinatorial Libraries," Biopolymers, 1995, 37:177-198.
Li et al., "A syntaxin 1, Galpha{o), and N -type calcium channel complex at a presynaptic nerve terminal: analysis by quantitative immunocolocalization," J Neurosci, 2004, 24(16):4070-4081.
Li et al., "Identification of novel HLA-A 0201-restricled cytotoxic T lymphocyte epilopes from Zinc Transporter 8," Vaccine, 2013, 31(12):1610-1615.
Li et al., "Multiplexed Anli-Toxoplasma IgG, IgM and IgA Assay on Plasmonic Gold Chips: Towards Making Mass Screening Possible with Dye Test Precision," J Clin Microbiol, 2016, 54:1726-1733.
Li et al., "Temporal Proteomic Analysis of Pancreatic beta-Cells in Response to Lipotoxicity and Glucolipotoxicity," Mol Cell Proteomics, 2018, 17(11):2119-2131.
Liu et al., "Characterization of Zinc Influx Transporters (ZIPs) in Pancreatic beta Cells: Roles in Regulating Cytosolic Zinc Homeostasis and Insulin Secretion," J Biol Chem, 2015, 290(30):18757-18769.
Liu et al., "Proinsulin maturation, misfolding, and proteotoxicity," Proc Natl Acad Sci USA, 2007, 104:15841-15846.
Long et al., "Rising incidence of type 1 diabetes is associated with altered immunophenotype at diagnosis," Diabetes, 2012, 61:683-686.
Madden et al., "Synthetic Combinatorial Libraries: Views on Techniques and Their Application,," Perspectives in Drug Discovery and Design, 1995, 2:269-282.
Maedler et al., "Distinct effects of saturated and monounsaturated fatty acids on betacell turnover and function," Diabetes, 2001, 50(1):69-76.
Mathiowitz et al., "Biologically erodable microssheres as potential oral drug delivery systems," Nature, 1997, 386(6623):410-4.
Meng et al., "Epoxomicin, a potent and selective proteasome inhibitor, exhibits in vivo antiinflammatory activity," Proc Natl Acad Sci USA, 1999, 96(18):10403-10408.
Murata et al., "The immunoproteasome and thymoproteasome: functions, evolution and human disease," Nat Immunol, 2018, 19(9):923-931.
NCBI Accession No. ABQ59023. 1, "SLC30A8 protein [*Homo sapiens*]".
NCBI Accession No. KR712225. 1, "Synthetic construct *Homo sapiens* clone CCSBHm_00900180 SLC30A8 (SLC30A8) mRNA, encodes complete protein."
Ohashi et al., "Zinc Transporter SLC39A7/ZIP7 Promotes Intestinal Epithelial Self-Renewal by Resolving ER Stress," DLoS Genet, 2016, 12 (10):e1006349.
PCT International Preliminary Report on Patentability in International Application No. PCT/US2017/029250, dated Oct. 30, 2018, 5 pages.
PCT International Search and Written Opinion in International Application No. PCT/US2017/029250, dated Aug. 17, 2017, 6 pages.
PCT Invitation to Pay Additional Fees and, Where Applicable, Protest Fee in International Application No. PCT/US2022/075156, mailed on Nov. 3, 2022, 2 pages.

Pietropaolo et al., "Primer: immunity and autoimmunity," Diabetes, 2008, 57(11):2872-2882.
Poitout et al., "Glucolipotoxicity of the pancreatic beta cell," Biochim Biophys Acta, 2010, 1801(3):289-298.
Regazzi et al., "VAMP-2 and cellubrevin are expressed in pancreatic beta-cells and are essential for Ca(2+)-but not or GTP gamma S-induced insulin secretion," EMBO J, 1995, 14(12):2723-2730.
Robertson et al., "Beta-cell glucose toxicity, lipotoxicity, and chronic oxidative stress in type 2 diabetes," Diabetes, 2004, 53(Suppl 1):S119-124.
Rojas et al., "Pancreatic Beta Cell Death: Novel Potential Mechanisms in Diabetes Therapy," J Diabetes Res, 2018, 9601801.
Saltiel et al., "Inflammatory mechanisms linking obesity and metabolic disease," J Clin Invest, 2017, 127(1):1-4.
Scheuner et al., "The unfolded protein response: a pathway that links insulin demand with beta-cell failure and diabetes," Endocr Rev, 2008, 29(3):317-333.
Schuit et al., "Glucose stimulates proinsulin biosynthesis by a dose-dependent recruitment of pancreatic beta cells," Droc Natl Acad Sci USA, 1988, 85(11):3865-386.
Scotto et al., "Zinc transporter $\{ZnT\}8\{$ 186-194) is an immunodominant COB+ T cell epitope in HLA-A2+ type 1 dliabetic patients," Diabetologia, 2012, 55(7):2026-2031.
Skarstrand et al., "Zinc transporter 8 (ZnT8) autoantibody epitope specificity and affinity examined with ecombinant ZnT8 variant proteins in specific ZnT8R and ZnT8W autoantibody-positive type 1 diabetes patients," Clinical & Experimental Immunology, 2015, 179(2):220-229.
Solimena et al., "ICA 512, an autoantigen of type I diabetes, is an intrinsic membrane protein of neurosecretory granules," EMBO J, 1996, 15(9):2102-2114.
Sosenko et al., "The Use of Electrochemiluminescence Assays to Predict Autoantibody and Glycemic Progression Toward Type 1 Diabetes in Individuals with Single Autoantibodies," Diabetes Technol Ther, 2017, 3:183-187.
Steck et al., "Predictors of Progression From the Appearance of Islet Autoantibodies to Early Childhood Diabetes: the Environmental Determinants of Diabetes in the Young (TEDDY)," Diabetes Care., 2015, 38(5):808-813.
Szoka et al., "Comparative properties and methods of preparation of lipid vesicles (liposomes)," Annu Rev Biophys Bioeng, 1980, 9:467-508 9.
Tabakman et al., "Plasmonic substrates for multiplexed protein microarrays with femlomolar sensitivity and broad dynamic range," Nat Commun.
Takenaga et al., "Microparticle resins as a potential nasal drug delivery system for insulin," J Control Release, 1998, 52:81-87.
Taylor et al., "Protein kinase CK2 triggers cytosolic zinc signaling pathways by phosphorylation of zinc channel ZIP7," Sci Signal, 2012, 5(210):ra11.
Thul et al., "A subcellular map of the human proteome," Science, 2017, 356(6340):eaal3321.
Tiberti et al., "Detection of four diabetes specific autoantibodies in a single radioimmunoassay: an nnovative high-throughput approach for autoimmune diabetes screening," 2011, Clin Exp Immunol 3:317-324.
Tsai et al., "Are obesity-related insulin resistance and type 2 diabetes autoimmune diseases?" Diabetes, 2015, 64(6):1886-1897.
Tuncay et al., "Hyperglycemia-Induced Changes in ZIP7 and ZnT7 Expression Cause Zn$\{2+$) Release From the Sarco(endo)plasmic Reticulum and Mediate ER Stress in the Heart," Diabetes, 2017,66(5):1346-1358.
Vinkenborg et al., "Genetically encoded FRET sensors to monitor intracellular Zn2+ homeostasis," Nat Methods, 2009, 6(10):737-740.
Wahl, "Molecular hybridization of immobilized nucleic acids: theoretical concepts and practical considerations," Methods in Enzymology, 1987, 152:399.
Wenzlau et al., "A common nonsynonymous single nucleotide polymorphism in the SLC30A8 gene determines ZnT8 Autoantibody specificity in type 1 diabetes," Diabetes, 2008, 57(10):2693-2697.

(56) References Cited

OTHER PUBLICATIONS

Wenzlau et al., "Changes in Zinc Transporter 8 Autoantibodies Following Type 1 Diabetes Onset: The Type 1 Diabetes Genetics Consortium Autoantibody Workshop," Diabetes Care, 2015, 38(Supplement 2):S14-20.
Wenzlau et al., "Novel diabetes autoantibodies and prediction of type 1 diabetes," Current Diabetes Reports, 2013, 13:608-615.
Wenzlau et al., "The cation efflux transporter Zn TB (Slc30A8) is a major autoantigen in human type 1 diabetes," Proc Natl Acad Sci USA, 2007, 104(43):17040-17045.
Woodruff et al., "The Zinc Transporter SLC39A7 (ZIP7) Is Essential for Regulation of Cytosolic Zinc Levels," Mol Dharmacol, 2018, 94(3):1092-1100.
Wu et al., "An electrochemiluminescence (ECL)-based assay for the specific detection of anti-drug antibodies of the IgE isotype," J Pham Biomed Anal, 2013, 86:73-81.
Yi et al., "Different role of zinc transporter 8 between type 1 diabetes mellitus and type 2 diabetes mellitus" J Diabetes Investig, 2016, 7:459-465.
Yu et al., "Antiislet autoantibodies usually develop sequentially rather than simultaneously," Journal of Clinical Endocrinology & Metabolism, 1996, 81(12):4264-4267.
Yu et al., "Early expression of antiinsulin autoantibodies of humans and the NOD mouse: evidence for early dletermination of subsequent diabetes," Proc Nall Acad Sci USA, 2000, 97(4):1701-1706.
Yu et al., "Identification of Candidate Tolerogenic CD8(+) T Cell Epitopes for Therapy of Type 1 Diabetes in the NOD Mouse Model," J Diabetes Res, 2016, 2016:9083103.
Yu et al., "Proinsulin/Insulin autoantibodies measured with electrochemiluminescent assay are the earliest indicator of prediabetic islet autoimmunity," Diabetes Care, 2013, 36(8):2266-2270.
Zhang et al., "A plasmonic chip for biomarker discovery and diagnosis of type 1 diabetes," Nat Med, 2013, 20:948-953.
Zhang et al., "Diagnosis of Zika virus infection on a nanotechnology platform," Nat Med 2017, 23:548-550.
Ziegler et al., "Seroconversion to multiple islet autoantibodies and risk of progression to diabetes in children," JAMA, 2013, 309(23):2473-2479.
Zumsteg et al., "Nitric oxide production and Fas surface expression mediate two independent pathways of cytokinenduced murine beta-cell damage," Diabetes, 2000, 49(1):39-47.
Kambe, et al., Current understanding of ZIP and ZnT zinc transporters in human health and diseases. Cell Mol Life Sci. Sep. 2014;71(17):3281-95.
Chimienti, et al., Identification and cloning of a beta-cell-specific zinc transporter, ZnT-8, localized into insulin secretory granules. Diabetes. Sep. 2004;53(9):2330-7.
Lemaire, et al., Zinc transporters and their role in the pancreatic β-cell. J Diabetes Investig. Jun. 6, 2012; 3(3): 202-211.
Segerstolpe, et al., Single-Cell Transcriptome Profiling of Human Pancreatic Islets in Health and Type 2 Diabetes. Cell Metab. Oct. 11, 2016;24(4):593-607.
Chimienti, et al., In vivo expression and functional characterization of the zinc transporter ZnT8 in glucose-induced insulin secretion. J Cell Sci. Oct. 15, 2006;119(Pt 20):4199-206.
Lemaire, et al., Insulin crystallization depends on zinc transporter ZnT8 expression, but is not required for normal glucose homeostasis in mice. Proc Natl Acad Sci U S A. Sep. 1, 2009;106(35):14872-7.
Nicolson, et al., Insulin storage and glucose homeostasis in mice null for the granule zinc transporter ZnT8 and studies of the type 2 diabetes-associated variants. Diabetes. Sep. 2009;58(9):2070-83.
Foster, et al., Elemental composition of secretory granules in pancreatic islets of Langerhans. Biophys J. Feb. 1993;64(2): 525-532.
Dunn, Zinc-ligand interactions modulate assembly and stability of the insulin hexamer—a review. Biometals. Aug. 2005;18(4):295-303.
Rutter, Think zinc: New roles for zinc in the control of insulin secretion. Islets. Jan.-Feb. 2010;2(1):49-50.

Tamaki, et al., The diabetes-susceptible gene SLC30A8/ZnT8 regulates hepatic insulin clearance. J Clin Invest. Oct. 2013;123(10):4513-24.
Ashcroft, et al., Diabetes mellitus and the β cell: the last ten years. Cell. Mar. 16, 2012;148(6):1160-71.
Prasad, et al., Genetics of Type 2 Diabetes—Pitfalls and Possibilities. Genes (Basel). Mar. 2015; 6(1): 87-123.
Bonneford, et al., Rare and common genetic events in type 2 diabetes: what should biologists know? Cell Metab. Mar. 3, 2015;21(3):357-68.
Flannick, et al., Loss-of-function mutations in SLC30A8 protect against type 2 diabetes. Nat Genet. Apr. 2014;46(4):357-63.
Pearson, Zinc transport and diabetes risk. Nat Genet. Apr. 2014;46(4):323-4.
Sladek, et al., A genome-wide association study identifies novel risk loci for type 2 diabetes. Nature. Feb. 22, 2007;445(7130):881-5.
Scott, et al., A genome-wide association study of type 2 diabetes in Finns detects multiple susceptibility variants. Science. Jun. 1, 2007;316(5829):1341-5.
Zeggini, et al., Replication of genome-wide association signals in UK samples reveals risk loci for type 2 diabetes. Science. Jun. 1, 2007;316(5829):1336-41.
Merriman, et al., Lipid-tuned Zinc Transport Activity of Human ZnT8 Protein Correlates with Risk for Type-2 Diabetes. J Biol Chem. Dec. 30, 2016;291(53):26950-26957.
Wong, et al., Exploring the Association Between Demographics, SLC30A8 Genotype, and Human Islet Content of Zinc, Cadmium, Copper, Iron, Manganese and Nickel. Sci Rep. Mar. 28, 2017;7(1):473.
Li, et al., hZnT8 (Slc30a8) Transgenic Mice That Overexpress the R325W Polymorph Have Reduced Islet Zn2+ and Proinsulin Levels, Increased Glucose Tolerance After a High-Fat Diet, and Altered Levels of Pancreatic Zinc Binding Proteins. Diabetes. Feb. 2017;66(2):551-559.
Pound, et al., Deletion of the mouse Slc30a8 gene encoding zinc transporter-8 results in impaired insulin secretion. Biochem J. Jul. 15, 2009;421(3):371-6.
Friend, et al., Translational genomics. Clues from the resilient. Science. May 30, 2014;344(6187):970-2.
Pound, et al., The physiological effects of deleting the mouse SLC30A8 gene encoding zinc transporter-8 are influenced by gender and genetic background. PLoS One. 2012;7(7):e40972.
Ohana, et al., Identification of the Zn2+ binding site and mode of operation of a mammalian Zn2+ transporter. J Biol Chem. Jun. 26, 2009;284(26):17677-86.
Hoch, et al., Histidine pairing at the metal transport site of mammalian ZnT transporters controls Zn2+ over Cd2+ selectivity. Proc Natl Acad Sci U S A. May 8, 2012;109(19):7202-7.
Lu, et al., Structure of the zinc transporter YiiP. Science. Sep. 21, 2007;317(5845):1746-8.
Lu, et al., Structural basis for autoregulation of the zinc transporter YiiP. Nat Struct Mol Biol. Oct. 2009;16(10):1063-7.
Degorce, et al., HTRF: A technology tailored for drug discovery—a review of theoretical aspects and recent applications. Curr Chem Genomics. May 28, 2009;3:22-32.
Merriman, et al., A subclass of serum anti-ZnT8 antibodies directed to the surface of live pancreatic β-cells. J Biol Chem. Jan. 12, 2018;293(2):579-587.
Ravassard, et al., A genetically engineered human pancreatic β cell line exhibiting glucose-inducible insulin secretion. J Clin Invest. Sep. 2011;121(9):3589-97.
Parsons, et al., The C-terminal cytosolic domain of the human zinc transporter ZnT8 and its diabetes risk variant. FEBS J. Apr. 2018;285(7):1237-1250.
Cherezov, et al., Insights into the mode of action of a putative zinc transporter CzrB in Thermus thermophilus. Structure. Sep. 10, 2008;16(9):1378-88.
Boesgaard, et al., The common SLC30A8 Arg325Trp variant is associated with reduced first-phase insulin release in 846 non-diabetic offspring of type 2 diabetes patients—the EUGENE2 study. Diabetologia. May 2008;51(5):816-20.
Lim, et al., High-efficiency screening of monoclonal antibodies for membrane protein crystallography. PLoS One. 2011;6(9):e24653.

(56) References Cited

OTHER PUBLICATIONS

Rohou, et al., CTFFIND4: Fast and accurate defocus estimation from electron micrographs. J Struct Biol. Nov. 2015;192(2):216-21.
Scheres, Relion: implementation of a Bayesian approach to cryo-EM structure determination. J Struct Biol. Dec. 2012;180(3):519-30.
Punjani, et al., cryoSPARC: algorithms for rapid unsupervised cryo-EM structure determination. Nat Methods. Mar. 2017;14(3):290-296.
Vyas, et al., Molecular recognition of oligosaccharide epitopes by a monoclonal Fab specific for Shigella flexneri Y lipopolysaccharide: X-ray structures and thermodynamics. Biochemistry. Nov. 19, 2002;41(46):13575-86.
Pettersen, et al., UCSF Chimera—a visualization system for exploratory research and analysis. J Comput Chem. Oct. 2004;25(13):1605-12.
Huang, et al., Coupling of Insulin Secretion and Display of a Granule-resident Zinc Transporter ZnT8 on the Surface of Pancreatic Beta Cells. J Biol Chem. Mar. 10, 2017;292(10):4034-4043.
Zhang, et al., A Simple Statistical Parameter for Use in Evaluation and Validation of High Throughput Screening Assays. J Biomol Screen. 1999;4(2):67-73.
Chatterjee, et al., Type 2 diabetes. Lancet. Jun. 3, 2017;389(10085):2239-2251.
Mittermayer, et al., Addressing unmet medical needs in type 2 diabetes: a narrative review of drugs under development. Curr Diabetes Rev. 2015;11(1):17-31.
Stumvoll, et al., Type 2 diabetes: principles of pathogenesis and therapy. Lancet. Apr. 9-15, 2005;365(9467):1333-46.
Inzucchi, et al., Management of hyperglycemia in type 2 diabetes: a patient-centered approach: position statement of the American Diabetes Association (ADA) and the European Association for the Study of Diabetes (EASD). Diabetes Care. Jun. 2012;35(6):1364-79.
Kim Sang Jick et al., Antibody Engineering for the Development of Therapeutic Antibodies. Molecules and Cells. 2005;20 (1): 17-29.
Atkinson, "The pathogenesis and natural history of type 1 diabetes," Cold Spring Harb Perspect Med, Nov. 2012, 2(11):a007641, 18 pages.
Batista et al., "B cells acquire antigen from target cells after synapse formation," Nature, May 24, 2011, 411(6836):489-494.
Campbell-Thompson et al., "Insulitis and beta-Cell Mass in the Natural History of Type 1 Diabetes," Diabetes, Nov. 18, 2015, 65(3):719-731.
Cheung et al., "The Current State of Beta-Cell-Mass PET Imaging for Diabetes Research and Therapies," Biomedicines, Dec. 3, 2021, 9:1824, 14 pages.
Controlled Drug Delivery: Fundamentals and Applications, 2nd ed., Robinson et al. (eds.), 1987, Chapter 15, 32 pages.
Grinberg-Bleyer et al., "IL-2 reverses established type 1 diabetes in NOD mice by a local effect on pancreatic regulatory T cells," J. Exp. Med., Aug. 2, 2010, 207(9):1871-1878.
Guo et al., "Cell-Surface Autoantibody Targets Zinc Transporter-8 (ZnT8) for In Vivo β-Cell Imaging and Islet-Specific Therapies," Diabetes, Feb. 1, 2023, 72(2):184-195.
Hartemann et al., "Low-dose interleukin 2 in patients with type 1 diabetes: a phase 1/2 randomised, double-blind, placebo-controlled trial," Lancet Diabetes Endocrinol., Dec. 2013, 1(4):295-305.
In't Veld, "Insulitis in human type 1 diabetes: a comparison between patients and animal models," Semin. Immunopathol., Sep. 2014, 36(5):569-579.
International Preliminary Report on Patentability in International Appln. No. PCT/US2022/075156, mailed on Feb. 29, 2024, 9 pages.
Jain et al., "Targeting pancreatic B cells for diabetes treatment," Nat Metab., Sep. 2022, 4:1097-1108.
Johnson et al., "β-cell-specific IL-2 therapy increases islet Foxp3+ Treg and suppresses type 1 diabetes in NOD mice," Diabetes, Oct. 18, 2013, 62(11)::3775-3784.
Kaestner et al., "NIH Initiative to Improve Understanding of the Pancreas, Islet, and Autoimmunity in Type 1 Diabetes: The Human Pancreas Analysis Program (HPAP)," Diabetes, May 24, 2019, 68(7):1394-1402.
Kahn et al., "The B cell in Diabetes: Integrating Biomarkers With Functional Measures," Endocr Rev., Jun. 28, 2021, 42:528-583.
Katsarou et al., "Type 1 diabetes mellitus," Nature Reviews Disease Primers, Mar. 30, 2017, 3:17016, 17 pages.
Kavishwar et al., "Unique sphingomyelin patches are targets of a beta-cell-specific antibody," J. Lipid Res., Sep. 2011, 52(9):1660-1671.
Khoryati et al., "An IL-2 mutein engineered to promote expansion of regulatory T cells arrests ongoing autoimmunity in mice," Sci. Immunol., Aug. 14, 2020, 5(50):eaba5264, 21 pages.
Manirarora et al.,"Combination therapy using IL-2/IL-2 monoclonal antibody complexes, rapamycin, and islet autoantigen peptides increases regulatory T cell frequency and protects against spontaneous and induced type 1 diabetes in nonobese diabetic mice," J. Immunol., Oct. 19, 2015, 195:5203-5214.
Marino et al., "B-cell cross-presentation of autologous antigen precipitates diabetes," Diabetes, Oct. 16, 2012, 61(11):2893-2905.
Milstein et al., "Hybrid hybridomas and their use in immunohistochemistry," Nature, Oct. 1983, 305(5834):537-540.
Modern Pharmaceutics, 4th ed., Banker et al. (eds.), 2002, Chapter 15, 29 pages.
Monoclonal Antibodies '84: Biological and Clinical Applications, 1st ed., Pinchera et al. (eds), 1984, 475-512.
Monoclonal Antibodies for Cancer Detection and Therapy, 1st ed., Baldwin et al.(eds.), 1985, Chapter 15, 14 pages.
Montanini et al., "Phylogenetic and functional analysis of the Cation Diffusion Facilitator (CDF) family: improved signature and prediction of substrate specificity," BMC Genomics, Apr. 23, 2007, 8:107, 16 pages.
Nayak et al., "ZnT8-reactive T cells are weakly pathogenic in NOD mice but can participate in diabetes under inflammatory conditions," Diabetes, Sep. 15, 2014, 63(10):3438-3448.
Orban et al., "Co-Stimulation Modulation with Abatacept in Patients with Recent-Onset Type 1 Diabetes: A Randomised Double-Masked Controlled Trial," Lancet, Jul. 30, 2011, 378(9789):412-419.
Reiner et al., "Accurate measurement of pancreatic islet beta-cell mass using a second-generation fluorescent exendin-4 analog," Proc. Natl. Acad. Sci. USA, Aug. 2, 2011, 108(31):12815-12820.
Rigby et al., "Alefacept provides sustained clinical and immunological effects in new-onset type 1 diabetes patients," J. Clin. Invest., Jul. 20, 2015, 125(8):3285-3296.
Rosenzwajg et al., "Low-dose IL-2 in children with recently diagnosed type 1 diabetes: a phase I/II randomised, double-blind, placebo-controlled, dose-finding study," Diabetologia, Jul. 1, 2020, 63:1808-1821.
Smith et al., "B cells in type 1 diabetes mellitus and diabetic kidney disease," Nat. Rev. Nephrol., Oct. 17, 2017, 13(11):712-720.
Sojar et al., "A chemical method for the deglycosylation of proteins," Arch Biochem Biophys., 1987, 259:52-57.
The Pharmacology of Monoclonal Antibodies, 1st ed., Rosenberg et al. (eds.), 1994, Chapter 11, 47 pages.
Uhlen et al., "Proteomics. Tissue-based map of the human proteome," Science, Jan. 23, 2015, 347(6220):1260419, 11 pages.
Wei et al., "Molecular imaging of B-cells: diabetes and beyond," Adv Drug Deliv Rev., Jan. 15, 2019, 139:16-31.
MacCallum et al., "Antibody-antigen Interactions: Contact Analysis and Binding Site Topography," J. Mol. Biol., 262:732-745 (Year: 1996).
Rudikoff et al., "Single amino acid substitution altering antigen-binding specificity," Proc Natl Acad Sci USA, 79:1979-1983 (Year: 1982).

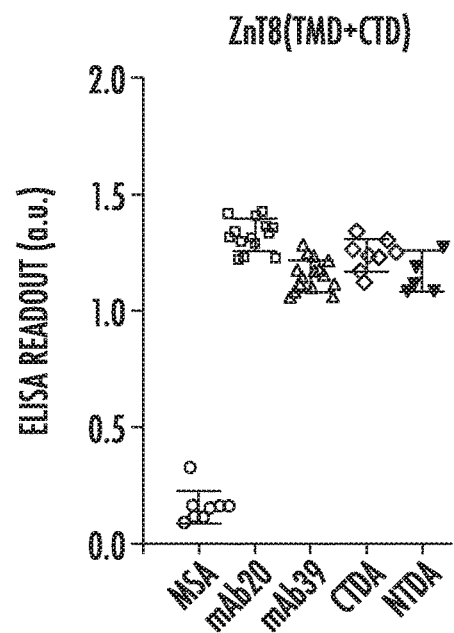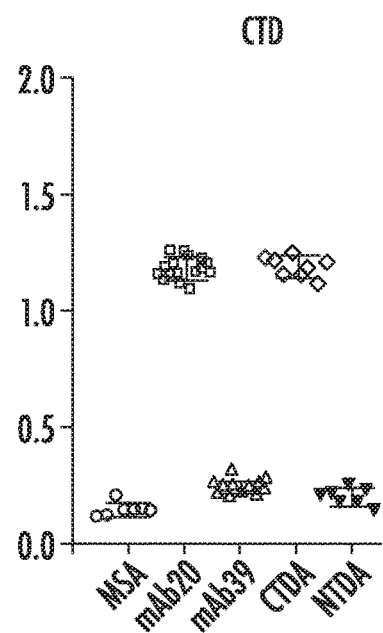
FIG. 1A  FIG. 1B
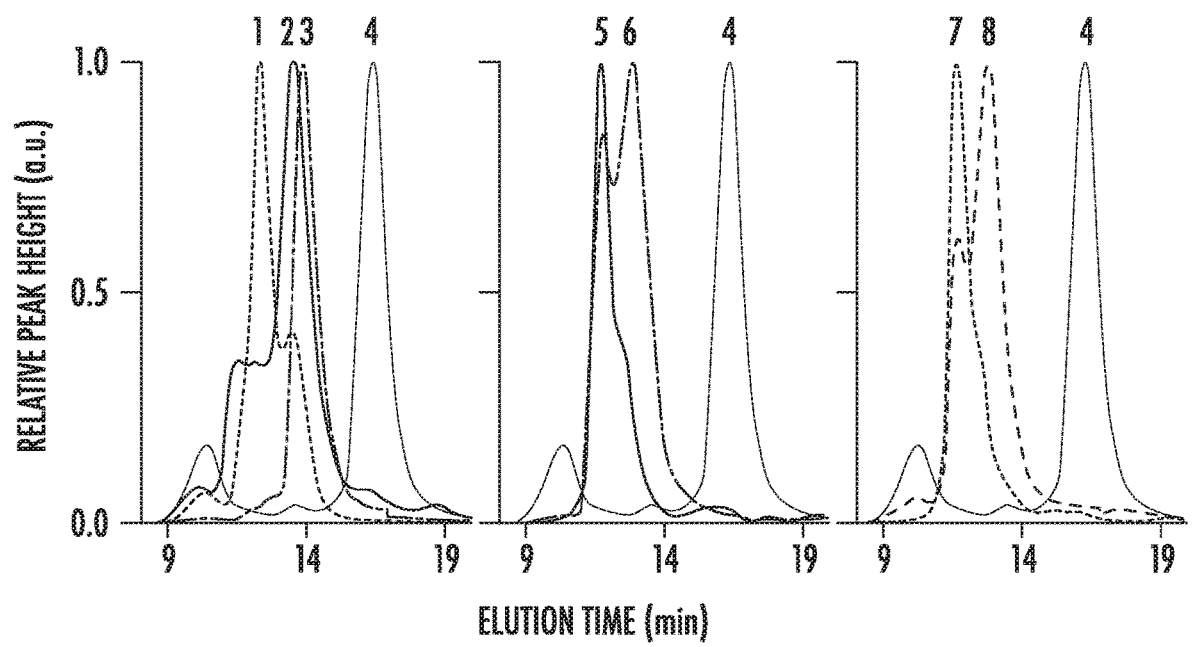
FIG. 2

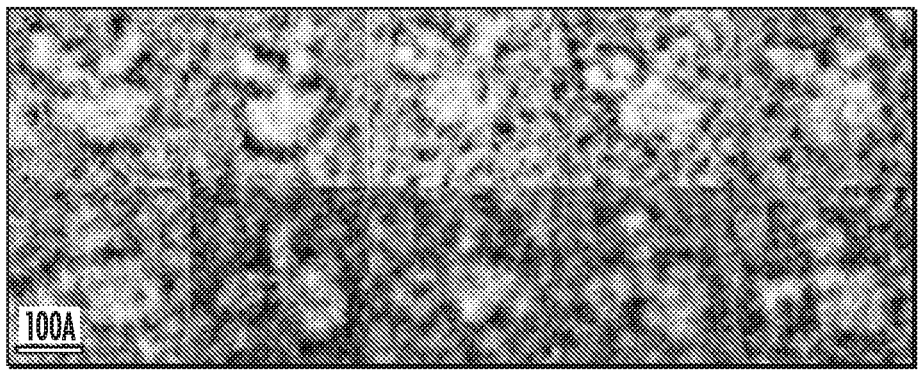
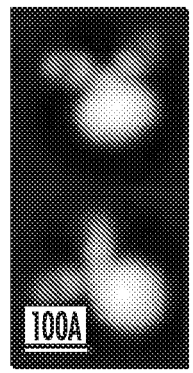
FIG. 3A                                    FIG. 3B
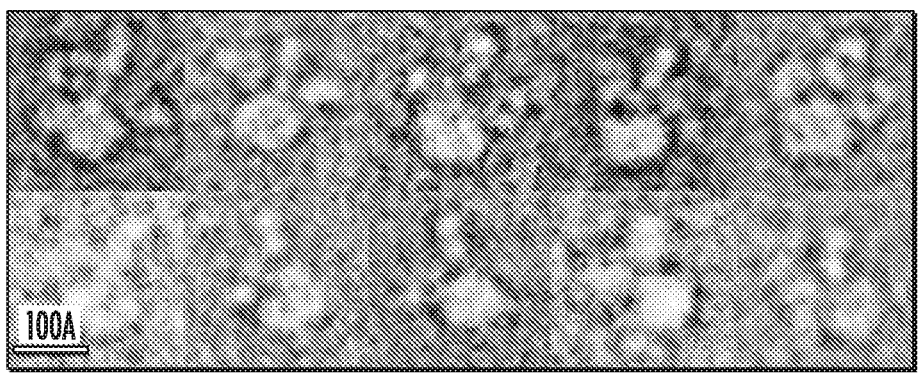
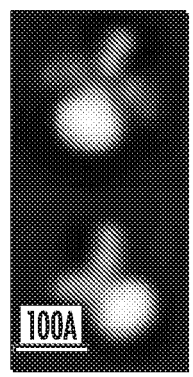
FIG. 3C                                    FIG. 3D

ANTIBODIES TO HUMAN ZNT8

CROSS-REFERENCE TO RELATED APPLICATIONS

This application is a 35 U.S.C. § 371 U.S. national entry of International Application PCT/US2019/046747 having an international filing date of Aug. 16, 2019, which claims the benefit of U.S. Provisional Application No. 62/719,016, filed Aug. 16, 2018, the content of each of the aforementioned applications is herein incorporated by reference in their entireties.

STATEMENT OF GOVERNMENTAL INTEREST

This invention was made with government support under grant no. GM065137, awarded by the National Institutes of Health. The government has certain rights in the invention.

FIELD OF THE INVENTION

The present invention relates to the fields of immunology and autoimmunity. More specifically, the present invention provides methods and compositions directed to the generation and use of antibodies to the pancreatic zinc transporter, ZnT8.

INCORPORATION-BY-REFERENCE OF MATERIAL SUBMITTED ELECTRONICALLY

This application contains a sequence listing. It has been submitted electronically via EFS-Web as an ASCII text file entitled "P15404-02_ST25.txt." The sequence listing is 69,547 bytes in size, and was created on Aug. 15, 2019. It is hereby incorporated by reference in its entirety.

BACKGROUND OF THE INVENTION

The human genome encodes a multitude of zinc transporters involved in regulation of cellular zinc homeostasis and signaling (1). Among all zinc transporters, Zinc Transporter-8 (ZnT8) is unique in its tissue-specific expression (2). Microarray profiling of mouse tissues (3) and single-cell transcriptome profiling of human pancreatic islets (4) showed that SCL30A8 transcription is mostly restricted to the endocrine cells of pancreatic islets. The transcriptional profile of SLC30A8 has a similar degree of islet specificity to that of well-known β-cell markers such as PDX1 and NKX6.1 (4). Single cell RNAseq showed that these β-cell markers also had "spill-over" transcription to non-β-endocrine cells, but the "spill-over" did not extend to exocrine or ductal cells (4). In islet β-cells, ZnT8 is primarily expressed in insulin secretory granules (2,5) where ZnT8 is required for granular zinc enrichment and zinc-insulin crystalline packaging in the form of hexameric insulins (6,7). The zinc content within insulin granules is over 10 mM (8). This high zinc level is implicated in insulin synthesis, storage, regulation of insulin secretion and hepatic insulin clearance following glucose stimulated insulin secretion (GSIS) (9-11).

Islet β-cells are the sole source in the human body for providing insulin. Insufficient insulin production is a major pathogenic component of type-2 diabetes (T2D) (12). The common T2D is a complex polygenic disease associated with more than 150 T2D-risk genes (13). Until now, SCL30A8 is the only one known for harboring protective loss-of-function (LOF) mutations (14). Genotyping ~150,000 individuals across multiple population cohorts revealed that carriers of LOF mutations had a 65% lower risk for T2D (15). This unique position of SLC30A8 in the genetic landscape of T2D susceptibility makes ZnT8 an attractive therapeutic target (16). Notably, a missense single-nucleotide polymorphism in SCL30A8 (rs13266634) is associated with increased susceptibility to T2D (17-19). Zinc transport activity of the higher-risk R325 variant is hyperactive compared with the lower-risk W325 variant (20), corresponding to a higher zinc level in human pancreatic islets from donors carrying the R325 variant (21). Moreover, transgenic mice overexpressing the R325 variant increased islet zinc level and decreased glucose tolerance after a high-fat diet (22), although GSIS phenotypes of ZnT8 KO-mouse models were heterogeneous (6,7,23,24). Emerging evidence from ZnT8 biochemistry, animal models and human genetics seems coalesced to suggest a causal relationship linking the gain-of-function R235 variant and increased T2D risk, supporting the case for ZnT8 inhibition as a potential antidiabetogenic strategy (16,25).

Two alternative approaches may be used to downregulate ZnT8 activity in β-cells: inhibiting zinc transport or reducing ZnT8 expression. The mechanism driving zinc transport is conserved from bacteria to humans (26,27). In a bacterial homolog YiiP (28), zinc transport is susceptible to allosteric regulation by zinc binding to a cytosolic C-terminal domain (CTD) (29). Likewise, allostery may be targeted for ZnT8 inhibition using mAb to trap ZnT8 in a fixed conformation, but a proof-of-principle allosteric inhibitor is still lacking. Moreover, functional regulation of ZnT8 expression in β-cells has yet to be investigated due to a lack of ZnT8-specific reagents for tracking the cellular ZnT8 level over a heterogenous background. Discovering specific and high affinity mAbs would permit testing the allosteric inhibition hypothesis while developing assays to quantify the cellular ZnT8 level.

SUMMARY OF THE INVENTION

The present invention is based, at least in part, on the development of monoclonal antibodies that specifically bind the pancreatic zine transporter, ZnT8. SLC30A8, the gene encoding ZnT8, is a susceptibility gene for type 2 diabetes. Reducing ZnT8 transport activity or downregulating its cellular expression is thought to be an antidiabetogenic strategy mimicking the protective effect of SLC30A8 haploinsufficiency in humans. However, research tools to inhibit ZnT8 and measure the cellular ZnT8 level are not available. As described herein, the present invention have developed monoclonal ZnT8 antibodies applicable to addressing these unmet needs. The mAbs exhibit sub-nanomolar affinities for human ZnT8 and selectivities against homologous zinc transporters with distinct cross-species reactivities and epitope recognition. Antigen binding fragments (Fab) protected ZnT8 from unfolding and inhibited ZnT8-mediated zinc transport in proteoliposomes. Negative-stain electron microscopy revealed a ternary binding complex of a ZnT8 monomer and two different Fabs at a 1:1:1 stoichiometry. The co-binding of two mAbs to a single ZnT8 protein multiplied individual anti-ZnT8 specificities, allowing for quantification of the cellular ZnT8 level by homogeneous time resolved fluorescence (HTRF). The mAbs described herein can be used as allosteric inhibitors and highly specific biosensors of human ZnT8.

In specific embodiments, the present invention provides an isolated antibody or antibody-binding fragment thereof that specifically binds to ZnT8, wherein the antibody or antibody-binding fragment comprises heavy chain complementarity determining regions (CDRs) 1, 2 and 3, wherein the heavy chain CDR1 comprises an amino acid sequence as set forth in one of SEQ ID NOS:3, 13, 23, 33, 43 and 53, or the amino acid sequence as set forth in one of SEQ ID NOS:3, 13, 23, 33, 43 and 53 with a substitution at two or fewer amino acid positions, the heavy chain CDR2 comprising an amino acid set forth in one of SEQ ID NOS:4, 14, 24, 34, 44 and 54, or the amino acid set forth in one of SEQ ID NOS:4, 14, 24, 34, 44 and 54 with a substitution at two or few amino acid positions, and the heavy chain CDR3 comprising an amino acid sequence as set forth in one of SEQ ID NOS:5, 15, 25, 35, 45, and 55, or the amino acid sequence as set forth in one of SEQ ID NOS:5, 15, 25, 35, 45, and 55 with a substitution at two or fewer amino acid positions.

In further embodiments, the isolated antibody or antigen-binding fragment further comprises light chain CDRs 1, 2 and 3, wherein the light chain CDR1 comprises an amino acid sequence as set forth in one of SEQ ID NOS:8, 18, 28, 38, 48 and 58, or the amino acid sequence as set forth in one of SEQ ID NOS:8, 18, 28, 38, 48 and 58 with a substitution at two or fewer amino acid positions, the light chain CDR2 comprising an amino acid sequence as set forth in one of SEQ ID NOS:9, 19, 29, 39, 49 and 59, or the amino acid sequence as set forth in one of SEQ ID NOS:9, 19, 29, 39, 49 and 59 with a substitution at two or fewer amino acid positions, and the light chain CDR3 comprising an amino acid sequence as set forth in one of SEQ ID NOS: 10, 20, 30, 40, 50 and 60, or the amino acid sequence as set forth in one of SEQ ID NOS: 10, 20, 30, 40, 50 and 60 with a substitution at two or fewer amino acid positions.

The present invention also provides an isolated antibody or antigen-binding fragment thereof that specifically binds to ZnT8, wherein the antibody or antigen-binding fragment thereof comprises a heavy chain variable region (VH) comprising CDR1, CDR2, and CDR3 consisting of the amino acid sequences as set forth in (a) SEQ ID NOS:3-5, respectively; (b) SEQ ID NOS:13-15, respectively; (c) SEQ ID NOS:23-25, respectively; (d) SEQ ID NOS:33-35, respectively; (e) SEQ ID NOS:43-45, respectively; and (f) SEQ ID NOS:53-55, respectively.

In alternative embodiments, an isolated antibody or antigen-binding fragment thereof that specifically binds to ZnT8 comprises a light chain variable region (VL) comprising CDR1, CDR2, and CDR3 consisting of the amino acid sequences as set forth in (a) SEQ ID NOS:8-10, respectively; (b) SEQ ID NOS:18-20, respectively; (c) SEQ ID NOS:28-30, respectively; (d) SEQ ID NOS:38-40, respectively; (e) SEQ ID NOS:48-50, respectively; and (f) SEQ ID NOS:58-60, respectively.

In particular embodiments, an isolated antibody or antigen-binding fragment thereof that specifically binds to ZnT8 comprises (a) a VH comprising CDR1, CDR2, and CDR, consisting of the amino acid sequences as set forth in (i) SEQ ID NOS:3-5, respectively; (ii) SEQ ID NOS:13-15, respectively; (iii) SEQ ID NOS:23-25, respectively; (iv) SEQ ID NOS:33-35, respectively; (v) SEQ ID NOS:43-45, respectively; or (vi) SEQ ID NOS:53-55, respectively; and (b) a VL comprising CDR1, CDR2, and CDR3, consisting of the amino acid sequences as set forth in (vii) SEQ ID NOS:8-10, respectively; (viii) SEQ ID NOS:18-20, respectively; (ix) SEQ ID NOS:28-30, respectively; (x) SEQ ID NOS:38-40, respectively; (xi) SEQ ID NOS:48-50, respectively; or (xii) SEQ ID NOS:58-60, respectively.

In certain embodiments, the isolated antibody or antigen-binding fragment is an antagonist of ZnT8 activity. The present invention also provides isolated nucleic acid molecules encoding the anti-ZnT8 antibodies or antigen-binding fragments thereof described herein. The present invention also provides vectors comprising a nucleic acid molecule described herein. In particular embodiments, a host cell comprises a vector described herein. The host cell can be a prokaryotic or a eukaryotic cell.

In another aspect, the present invention provides methods for producing an anti-ZnT8 antibody or antigen-binding fragment thereof. In one embodiment, a method for producing an anti-ZnT8 antibody or antigen-binding fragment thereof comprises the steps of (a) culturing a host cell described herein under conditions suitable for expression of the ZnT8 antibody or antigen-binding fragment thereof by the host cells; and (b) recovering the ZnT8 antibody or antigen-binding fragment thereof. The host cell can be a prokaryotic or a eukaryotic cell.

In another aspect, the present invention provides compositions comprising the anti-ZnT8 antibody or antigen-binding fragment thereof described herein and a suitable pharmaceutical carrier. The composition can be formulated for intravenous, intramuscular, oral, subcutaneous, intraperitoneal, intrathecal or intramuscular administration.

In a further aspect, the present invention provides methods for treating ZnT8-mediated diseases or conditions including, but not limited to, diabetes. In a specific embodiment, a method of treating diabetes in a mammal comprises the step of administering to the mammal a therapeutically effective amount of the antibody or antigen-binding fragment thereof described herein that specifically binds to ZnT8.

In specific embodiment, an isolated antibody or antigen-binding fragment thereof that specifically binds ZnT8, wherein the antibody or antigen-binding fragment thereof comprises (a) a VH comprising CDRs 1, 2, and 3 with the amino acid sequences set forth in SEQ ID NOS:3-5, respectively and a VH comprising CDRs 1, 2, and 3 with the amino acid sequences set forth in SEQ ID NOS:8-10, respectively; or (b) a VH comprising CDRs 1, 2, and 3 with the amino acid sequences set forth in SEQ ID NOS:13-15, respectively and a VH comprising CDRs 1, 2, and 3 with the amino acid sequences set forth in SEQ ID NOS:18-20, respectively; or (c) a VH comprising CDRs 1, 2, and 3 with the amino acid sequences set forth in SEQ ID NOS:23-25, respectively and a VH comprising CDRs 1, 2, and 3 with the amino acid sequences set forth in SEQ ID NOS:28-30, respectively; or (d) a VH comprising CDRs 1, 2, and 3 with the amino acid sequences set forth in SEQ ID NOS:33-35, respectively and a VH comprising CDRs 1, 2, and 3 with the amino acid sequences set forth in SEQ ID NOS:38-40, respectively; or (e) a VH comprising CDRs 1, 2, and 3 with the amino acid sequences set forth in SEQ ID NOS:43-45, respectively and a VH comprising CDRs 1, 2, and 3 with the amino acid sequences set forth in SEQ ID NOS:48-50, respectively; or (f) a VH comprising CDRs 1, 2, and 3 with the amino acid sequences set forth in SEQ ID NOS:53-55, respectively and a VH comprising CDRs 1, 2, and 3 with the amino acid sequences set forth in SEQ ID NOS:58-60, respectively. In certain embodiments, the antigen-binding fragment is selected from the group consisting of an scFv, sc(Fv)2, Fab, F(ab)2, and a diabody.

The present invention also provides an isolated antibody or antigen-binding fragment thereof that specifically binds ZnT8 comprising a VH comprising one of the amino acid sequences set forth in SEQ ID NOS:2, 12, 22, 32, 42 and 52. In alternative embodiments an isolated antibody or antigen-binding fragment thereof that specifically binds ZnT8 comprises a VL comprising one of the amino acid sequences as set forth in SEQ ID NOS:7, 17, 27, 37, 47 and 57.

In further embodiments, an isolated antibody or antigen-binding fragment thereof that specifically binds ZnT8 comprises: (a) a VH comprising the amino acid sequence as set forth in SEQ ID NO:2 and a VL comprising the amino acid sequence as set forth in SEQ ID NO:7; (b) a VH comprising the amino acid sequence as set forth in SEQ ID NO: 12 and a VL comprising the amino acid sequence as set forth in SEQ ID NO:17; (c) a VH comprising the amino acid sequence as set forth in SEQ ID NO:22 and a VL comprising the amino acid sequence as set forth in SEQ ID NO:27; (d) a VH comprising the amino acid sequence as set forth in SEQ ID NO:32 and a VL comprising the amino acid sequence as set forth in SEQ ID NO:37; (e) a VH comprising the amino acid sequence as set forth in SEQ ID NO:42 and a VL comprising the amino acid sequence as set forth in SEQ ID NO:47; or (f) a VH comprising the amino acid sequence as set forth in SEQ ID NO:52 and a VL comprising the amino acid sequence as set forth in SEQ ID NO:57.

BRIEF DESCRIPTION OF THE FIGURES

FIG. 1A-1B. Mapping mAb binding sites (FIG. 1A) ELISA against ZnT8 (TMD+CTD) in proteoliposomes immobilized by passive coating. Bound antibodies were detected by HRP-conjugated secondary antibodies. The assay was calibrated by CTDA and NTDA as positive controls and MSA as a negative control with a Z' factor>0.5. Error bars represent standard deviations. (FIG. 1B) ELISA against a monomeric CTD antigen immobilized to Ni-NTA plate via a C-terminal poly-histidine tag. CTDA and NTDA were used a positive and negative control, respectively (Z>0.5).

FIG. 2. ZnT8-antibody complexes Size-exclusion HPLC chromatograms of ZnT8 in complex with mAb20, Fab20 and/or mAb39 in various combinations and binding stoichiometries. Eight distinct peaks were resolved, labeled as 1 through 8. Corresponding complex molecular weights and predicted complex compositions are summarized in Table-1. mAb20/Fab20 and mAb39 were fluorescently labeled and detected either in green (shown as blue traces) or red (red traces) channel of a multi-channel fluorescence detector. Grey traces are unbound ZnT8 detected by UV absorption.

FIG. 3A-3F. EM analysis of ZnT8-Fab complexes. (FIG. 3A) Representative raw particles of the binary complex ZnT8-(Fab20)$_2$ in negative stain. Scale bar, 100 Å. (FIG. 3B) Representative reference-free 2D-class averages of the binary complexes. (FIG. 3C) Representative raw particles of ternary complex (Fab20)$_2$-ZnT8-(Fab39)$_2$. (FIG. 3D) Representative reference-free 2D-class averages of the ternary complexes. (FIG. 3E) 3D map of ZnT8-(Fab20)$_2$ in two views related by a 90° rotation around a two-fold axis perpendicular to the membrane plane (black dashed line). Atomic models of a Fab20 (PDB ID 1M71) and ZnT8 homolog (PDB ID 3H90) were fitted into the low-resolution envelope, and colored in cyan and yellow, respectively. (FIG. 3F) 3D model of (Fab20)$_2$-ZnT8-(Fab39)$_2$ in two views docked with four Fab structures, representing two Fab20 (cyan) and two Fab39 (magenta), respectively. ZnT8 dimer model is shown in yellow. A blue dashed curve marks the boundary between two Fab39 molecules on top in close proximity.

(FIG. 4B) mAb binding to folded ZnT8-GFP in detergent micelles. mAb20 or mAb39 was mixed with ZnT8-GFP and then the binding mixture was analyzed by size-exclusion HPLC with GFP-fluorescence detection. Note, mAb20 shifted the unbound ZnT8-GFP peak (black) leftward to a mAb20-ZnT8-GFP position (red) while mAb39 did not cause peak shift (magenta). (FIG. 4C) Protection of ZnT8 unfolding. Aliquots of ZnT8 in detergent micelles were incubated with Fab20 (red), Fab39 (magenta), or Fab20+Fab39 (brown). Free ZnT8 was used as a control (black). After a designated time of heat denaturation as indicated, protein aggregates were removed by ultracentrifugation, and the amount of remaining ZnT8 in the supernatant was detected by mAb20 immunoblotting (upper panel). Error bars are standard errors of 6 independent densitometric measurements of one representative experiment using ImageJ.

(FIG. 5B) Steady-state kinetics for zinc transport mediated by ZnT8, or ZnT8 bound with Fab20, Fab39 or Fab20+Fab39 as indicated. Solid lines are least squares fits to the Michaelis-Menten equation. Km and Vmax values are summarized in Table-2.

(FIG. 6A) Representative confocal microscopy images of immunofluorescence staining of fixed and saponin-permeabilized HEK293 cells with mAb20 or mAb39 staining as indicated. ZnT8(+) or ZnT8(−) denotes HEK293 cells w/o ZnT8 over-expression. Red: mAb20 or mAb39 staining, blue: DAPI, scale bar: 5 µm. (FIG. 6B) Histograms of flow cytometry counting events. Arrows indicate leftward shifts of the histogram as a result of mAb serial dilutions. (FIG. 6C) mAb binding to HEK293 cells w/o ZnT8 overexpression as indicated. Immunofluorescence intensities of mAb20 or mAb39 labeling in serial dilutions were obtained from (FIG. 6B). Solid lines are least-squares fits of the binding data to a one-component binding process.

(FIG. 7B) SDS-denatured mouse ZnT8-His (labeled as M) and human ZnT8-His (labeled as H) on immunoblots were detected by mAb20 or mAb39 as indicated. A replicated immunoblot was probed by an anti-His-tag antibody to show that approximately same amounts of HEK293 crude lysates were loaded to each lane. (FIG. 7C) Detection of endogenous human ZnT8 in EndoC-βH cells by mAb20 or mAb38 immunoblotting. An equal amount of EndoC-βH lysate (5 µg total protein) was loaded to each lane. (FIG. 7D) Immunoblotting of HEK lysates with or with over-expression of a ZnT homolog as indicated. An approximately equal amount of total lysate protein (5 μg) was located to each lane, probed by either mAb20, mAb39, or anti-FALG antibody as indicated.

DETAILED DESCRIPTION OF THE INVENTION

Figure 3E:
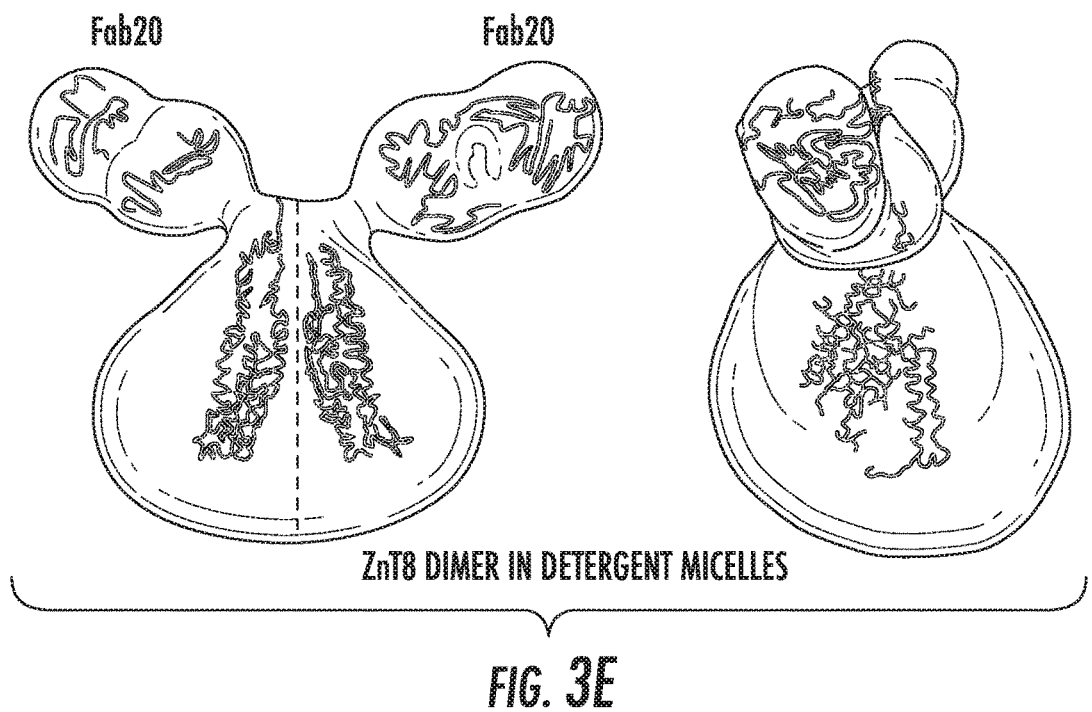

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "antibody" means an immunoglobulin molecule that recognizes and specifically binds to a target, such as a protein (e.g., the ZNT8, a subunit thereof, or the receptor complex), polypeptide, peptide, carbohydrate, polynucleotide, lipid, or combinations of the foregoing through at least one antigen recognition site within the variable region of the immunoglobulin molecule. A typical antibody comprises at least two heavy (HC) chains and two light (LC) chains interconnected by disulfide bonds. Each heavy chain is comprised of a "heavy chain variable region" or "heavy chain variable domain" (abbreviated herein as VH) and a heavy chain constant region. The heavy chain constant region is comprised of three domains, CHI, CH2, and CH3. Each light chain is comprised of a "light chain variable region" or "light chain variable domain" (abbreviated herein as VL) and a light chain constant region. The light chain constant region is comprised of one domain, CI. The VH and VL regions can be further subdivided into regions of hypervariability, termed Complementarity Determining Regions (CDR), interspersed with regions that are more conserved, termed framework regions (FRs). Each VH and VL region is composed of three CDRs and four FRs, arranged from amino-terminus to carboxy-terminus in the following order: FRI, CDRI, FR2, CDR2, FR3, CDR3, FR4. The variable regions of the heavy and light chains contain a binding domain that interacts with an antigen. As used herein, the term "antibody" encompasses intact poly clonal antibodies, intact monoclonal antibodies, antibody fragments (such as Fab, Fab', F(ab')2, Fd, Facb, and Fv fragments), single chain Fv (scFv), minibodies (e.g., sc(Fv)2, diabody), multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, radioisotopes, small molecule drugs, polypeptides, etc.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody is purified (1) to greater than 95% by weight of antibody as determined by, for example, the Lowry method, and including more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or silver stain. An isolated antibody includes the antibody in situ within recombinant cells since at least one component of the antibody's natural environment will not be present. Ordinarily, however, isolated antibody will be prepared by at least one purification step.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human.

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antigen-binding antibody fragments include, but are not limited to Fab, Fab', F(ab')2, Facb, Fd, and Fv fragments, linear antibodies, single chain antibodies, and multi-specific antibodies formed from antibody fragments. In some instances, antibody fragments may be prepared by proteolytic digestion of intact or whole antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced. The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced. The term "Fv" refers to an antibody fragment that consists of one NH and one N domain held together by noncovalent interactions.

The terms "ZNT8 antibody," "anti-ZNT8 antibody," "anti-ZNT8," "antibody that binds to ZNT8" and any grammatical variations thereof refer to an antibody that is capable of specifically binding to ZNT8 with sufficient affinity such that the antibody is useful as a therapeutic agent or diagnostic reagent in targeting ZNT8. The extent of binding of an anti-ZNT8 antibody disclosed herein to an unrelated, non-ZNT8 protein is less than about 10% of the binding of the antibody to ZNT8 as measured, e.g., by a radioimmunoassay (RIA), BIACORE™ (using recombinant ZNT8 as the analyte and antibody as the ligand, or vice versa), or other binding assays known in the art. In certain embodiments, an antibody that binds to ZNT8 has a dissociation constant (KD) of <1 µM, <100 nM, <50 nM, <10 nM, or <1 nM.

The term "% identical" between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site. Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2 (ClustalX is a version of the ClustalW2 program ported to the Windows environment). Another suitable program is MUSCLE. ClustalW2 and MUSCLE are alternatively available, e.g., from the European Bioinformatics Institute (EBI).

The term "therapeutic agent" refers to any biological or chemical agent used in the treatment of a disease or disorder. Therapeutic agents include any suitable biologically active chemical compounds, biologically derived components such as cells, peptides, antibodies, and polynucleotides, and radiochemical therapeutic agents such as radioisotopes. In some embodiments, the therapeutic agent comprises a chemotherapeutic agent or an analgesic.

As used herein, the terms "treatment," "treating," "treat" and the like, refer to obtaining a desired pharmacologic and/or physiologic effect. The terms are also used in the context of the administration of a "therapeutically effective amount" of an agent, e.g., an anti-ZnT8 antibody. The effect may be prophylactic in terms of completely or partially preventing a particular outcome, disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In particular embodiments, the term is used in the context of preventing or treating any ZnT8-mediated disease including diabetes.

II. Anti-ZnT8 Antibodies

The antibodies or antigen-binding fragment thereof of this disclosure specifically bind to ZNT8. In specific embodiments, these antibodies or antigen-binding fragments specifically bind to human ZNT8. "Specifically binds" as used herein means that the antibody or antigen-binding fragment preferentially binds ZNT8 (e.g., human ZNT8, mouse ZNT8) over other proteins. In certain instances, the anti-ZNT8 antibodies of the disclosure have a higher affinity for ZNT8 than for other proteins. Anti-ZNT8 antibodies that specifically bind ZNT8 may have a binding affinity for human ZNT8 of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6\times10^{-7}$ M, less than or equal to $7\times10^{-7}$ M, less than or equal to $8\times10^{-7}$ M, less than or equal to $9\times10^{-7}$ M, less than or equal to $1\times10^{-8}$ M, less than or equal to $2\times10^{-8}$ M, less than or equal to $3\times10^{-8}$ M, less than or equal to $4\times10^{-8}$ M, less than or equal to $5\times10^{-8}$ M, less than or equal to $6\times10^{-8}$ M, less than or equal to $7\times10^{-8}$ M, less than or equal to $8\times10^{-8}$ M, less than or equal to $9\times10^{-8}$ M, less than or equal to $1\times10^{-9}$ M, less than or equal to $2\times10^{-9}$ M, less than or equal to $3\times10^{-9}$ M, less than or equal to $4\times10^{-9}$ M, less than or equal to $5\times10^{-9}$ M, less than or equal to $6\times10^{-9}$ M, less than or equal to $7\times10^{-9}$ M, less than or equal to $8\times10^{-9}$ M, less than or equal to $9\times10^{-9}$ M, less than or equal to $1\times10^{-10}$ M, less than or equal to $2\times10^{-10}$ M, less than or equal to $3\times10^{-10}$ M, less than or equal to $4\times10^{-10}$ M, less than or equal to $5\times10^{-10}$ M, less than or equal to $6\times10^{-10}$ M, less than or equal to $7\times10^{-10}$ M, less than or equal to $8\times10^{-10}$ M, less than or equal to $9\times10^{-10}$ M, less than or equal to $1\times10^{-11}$ M, less than or equal to $2\times10^{-11}$ M, less than or equal to $3\times10^{-11}$ M, less than or equal to $4\times10^{-11}$ M, less than or equal to $5\times10^{-11}$ M, less than or equal to $6\times10^{-11}$ M, less than or equal to $7\times10^{-11}$ M, less than or equal to $8\times10^{-11}$ M, less than or equal to $9\times10^{-11}$ M, less than or equal to $1\times10^{-12}$ M, less than or equal to $2\times10^{-12}$ M, less than or equal to $3\times10^{-12}$ M, less than or equal to $4\times10^{-12}$ M, less than or equal to $5\times10^{-12}$ M, less than or equal to $6\times10^{-12}$ M, less than or equal to $7\times10^{-12}$ M, less than or equal to $8\times10^{-12}$ M, or less than or equal to $9\times10^{-12}$ M. Methods of measuring the binding affinity of an antibody are well known in the art and include Surface Plasmon Resonance (SPR) (Morton and Myszka "Kinetic analysis of macromolecular interactions using surface plasmon resonance biosensors" *Methods in Enzymology* (1998) 295, 268-294), Bio-Layer Interferometry, (Abdiche et al "Determining Kinetics and Affinities of Protein Interactions Using a Parallel Real-time Label-free Biosensor, the Octet" *Analytical Biochemistry* (2008) 377, 209-217), Kinetic Exclusion Assay (KinExA) (Darling and Brault "Kinetic exclusion assay technology: characterization of molecular interactions" *Assay and Drug Dev Tech* (2004) 2, 647-657), isothermal calorimetry (Pierce et al "Isothermal Titration Calorimetry of Protein-Protein Interactions" *Methods* (1999) 19, 213-221) and analytical ultracentrifugation (Lebowitz et al "Modern analytical ultracentrifugation in protein science: A tutorial review" *Protein Science* (2002), 11:2067-2079).

A. Antibody Fragments

The present disclosure encompasses the antibody fragments or domains described herein that retains the ability to specifically bind to ZNT8 (e.g., human ZNT8). Antibody fragments include, e.g., Fab, Fab', F(ab')2, Facb, and Fv. These fragments may be humanized or fully human. Antibody fragments may be prepared by proteolytic digestion of intact antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., *J Immunol.*, 152:2968-2976 (1994); Better, M. and Horwitz, A. H., *Methods in Enzymology*, 178:476-496 (1989); Pluckthun, A and Skerra, A, *Methods in Enzymology*, 178:476-496 (1989); Lamoyi, E., *Methods in Enzymology*, 121:652-663 (1989); Rousseaux, J. et al., *Methods in Enzymology*, (1989) 121:663-669 (1989); and Bird, R E. et al., *TIBTECH*, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)2 fragments (Carter et al., *Bio/Technology*, 10:163-167 (1992)). According to another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046.

B. Minibodies

Also encompassed are minibodies of the antibodies described herein. Minibodies of anti-ZNT8 antibodies include diabodies, single chain (scFv), and single-chain (Fv)2 (sc(Fv)2).

A "diabody" is a bivalent minibody constructed by gene fusion (see, e.g., Holliger, P. et al., *Proc. Nat. Acad. Sci. U S. A.*, 90:6444-6448 (1993); EP 404,097; WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.

An scFv is a single-chain polypeptide antibody obtained by linking the VH and VL with a linker (see e.g., Huston et al., *Proc. Nat. Acad. Sci. U S. A.*, 85:5879-5883 (1988); and Pluckthun, "The Pharmacology of Monoclonal Antibodies" Vol. 113, Ed Resenburg and Moore, Springer Verlag, New York, pp. 269-315, (1994)). Each variable domain (or a portion thereof) is derived from the same or different antibodies. Single chain Fv molecules preferably comprise an scFv linker interposed between the VH domain and the VL domain. Exemplary scFv molecules are known in the art and are described, for example, in U.S. Pat. No. 5,892,019; Ho et al, *Gene*, 77:51 (1989); Bird et al., *Science*, 242:423 (1988); Pantoliano et al, *Biochemistry*, 30: 101 17 (1991); Milenic et al, *Cancer Research*, 51:6363 (1991); Takkinen et al, *Protein Engineering*, 4:837 (1991).

The term "scFv linker" as used herein refers to a moiety interposed between the VL and VH domains of the scFv. The scFv linkers preferably maintain the scFv molecule in an antigen-binding conformation. In one embodiment, an scFv linker comprises or consists of an scFv linker peptide. In certain embodiments, an scFv linker peptide comprises or consists of a Gly-Ser peptide linker. In other embodiments, an scFv linker comprises a disulfide bond.

The order of VHs and VLs to be linked is not particularly limited, and they may be arranged in any order. Examples of arrangements include: [VH] linker [VL]; or [VL] linker [VH]. The H chain V region and L chain V region in an scFv may be derived from any anti-ZNT8 antibody or antigen-binding fragment thereof described herein.

An sc(Fv)2 is a minibody in which two VHs and two VLs are linked by a linker to form a single chain (Hudson, et al., *J Immunol. Methods*, (1999) 231: 177-189 (1999)). An sc(Fv)2 can be prepared, for example, by connecting scFvs with a linker. The sc(Fv)2 of the present invention include antibodies preferably in which two VHs and two VLs are arranged in the order of: VH, VL, VH, and VL ([VH] linker [VL] linker [VH] linker [VL]), beginning from the N terminus of a single-chain polypeptide; however, the order of the two VHs and two VLs is not limited to the above arrangement, and they may be arranged in any order. Examples of arrangements are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

Normally, three linkers are required when four antibody variable regions are linked; the linkers used may be identical or different. There is no particular limitation on the linkers that link the VH and VL regions of the minibodies. In some embodiments, the linker is a peptide linker. Any arbitrary single-chain peptide comprising about 3 to 25 residues (e.g., 5, 6, 7, 8, 9, 10, 11, 12, 13, 14, 15, 16, 17, 18) can be used as a linker.

In other embodiments, the linker is a synthetic compound linker (chemical cross-linking agent). Examples of cross-linking agents that are available on the market include N-hydroxysuccinimide (NHS), disuccinimidylsuberate (DSS), bis(sulfosuccinimidyl)suberate (BS3), dithiobis(succinimidy lpropionate) (DSP), dithiobis(sulfosuccinimidy lpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

The amino acid sequence of the VH or VL in the antibody fragments or minibodies may include modifications such as substitutions, deletions, additions, and/or insertions. For example, the modification may be in one or more of the CDRs of the anti-ZNT8 antibodies described herein. In certain embodiments, the modification involves one, two, or three amino acid substitutions in one, two, or three CDRs of the VH and/or one, two, or three CDRs of the VL domain of the anti-ZNT8 minibody. Such substitutions are made to improve the binding and/or functional activity of the anti-ZNT8 minibody. In other embodiments, one, two, or three amino acids of one or more of the six CDRs of the anti-ZNT8 antibody or antigen-binding fragment thereof may be deleted or added as long as there is ZNT8 binding and/or functional activity when VH and VL are associated.

C. VHH

VHH also known as nanobodies are derived from the antigen-binding variable heavy chain regions (VHHs) of heavy chain antibodies found in camels and llamas, which lack light chains. The present disclosure encompasses VHHs that specifically bind ZNT8.

D. Variable Domain of New Antigen Receptors (VNARs)

A VNAR is a variable domain of anew antigen receptor (IgNAR). IgNARs exist in the sera of sharks as a covalently linked heavy chain homodimer. It exists as a soluble and receptor bound form consisting of a variable domain (VNAR) with differing numbers of constant domains. The VNAR is composed of a CDR1 and CDR3 and in lieu of a CDR2 has HV2 and HV4 domains (see, e.g., Barelle and Porter, Antibodies, 4:240-258 (2015)). The present disclosure encompasses VNARs that specifically bind ZNT8.

E. Constant Regions

Antibodies of this disclosure can be whole antibodies or single chain Fc (scFc) and can comprise any constant region known in the art. The light chain constant region can be, for example, a kappa- or lambda-type light chain constant region, e.g., a human kappa or human lambda light chain constant region. The heavy chain constant region can be, e.g., an alpha-, delta-, epsilon-, gamma-, or mu-type heavy chain constant region, e.g., a human alpha-, human delta-, human epsilon-, human gamma-, or human mu-type heavy chain constant region. In certain instances, the anti-ZNT8 antibody is an IgA antibody, an IgD antibody, an IgE antibody, an IgG1 antibody, an IgG2 antibody, an IgG3 antibody, an IgG4 antibody, or an IgM antibody.

In one embodiment, the light or heavy chain constant region is a fragment, derivative, variant, or mutein of a naturally occurring constant region. In some embodiments, the variable heavy chain of the anti-ZNT8 antibodies described herein is linked to a heavy chain constant region comprising a CH1 domain and a hinge region. In some embodiments, the variable heavy chain is linked to a heavy chain constant region comprising a CH2 domain. In some embodiments, the variable heavy chain is linked to a heavy chain constant region comprising a CH3 domain. In some embodiments, the variable heavy chain is linked to a heavy chain constant region comprising a CH2 and CH3 domain. In some embodiments, the variable heavy chain is linked to a heavy chain constant region comprising a hinge region, a CH2 and a CH3 domain. The CH1, hinge region, CH2, and/or CH3 can be from an IgG antibody (e.g., IgGI, IgG4). In certain embodiments, the variable heavy chain of an anti-ZNT8 antibody described herein is linked to a heavy chain constant region comprising a CHI domain, hinge region, and CH2 domain from IgG4 and a CH3 domain from IgGI. In certain embodiments such a chimeric antibody may contain one or more additional mutations in the heavy chain constant region that increase the stability of the chimeric antibody. In certain embodiments, the heavy chain constant region includes substitutions that modify the properties of the antibody.

In certain embodiments, an anti-ZNT8 antibody of this disclosure is an IgG isotype antibody. In one embodiment, the antibody is IgG1. In another embodiment, the antibody is IgG2. In yet another embodiment, the antibody is IgG4. In some instances, the IgG4 antibody has one or more mutations that reduce or prevent it adopting a functionally monovalent format. For example, the hinge region of IgG4 can be mutated to make it identical in amino acid sequence to the hinge region of human IgG1 (mutation of a serine in human IgG4 hinge to a proline). In some embodiments, the antibody has a chimeric heavy chain constant region (e.g., having the CH1, hinge, and CH2 regions of IgG4 and CH3 region of IgG1).

F. Bispecific Antibodies

In certain embodiments, an anti-ZNT8 antibody of this disclosure is a bispecific antibody. Bispecific antibodies are antibodies that have binding specificities for at least two different epitopes. Exemplary bispecific antibodies may bind to two different epitopes of the ZNT8 protein. Other such antibodies may combine a ZNT8 binding site with a binding site for another protein. Bispecific antibodies can be prepared as full length antibodies or low molecular weight forms thereof (e.g., F(ab')2 bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., Nature, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

G. Conjugated Antibodies

The antibodies or antigen-binding fragments disclosed herein may be conjugated to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), human serum albumin or a fragment thereof, radioactive materials (e.g., $^{90}$Y, $^{131}$I), fluorescent substances, luminescent substances, haptens, enzymes, metal chelates, and drugs.

In certain embodiments, an anti-ZNT8 antibody or antigen-binding fragment thereof is modified with a moiety that improves its stabilization and/or retention in circulation, e.g., in blood, serum, or other tissues, e.g., by at least 1.5, 2, 5, 10, 15, 20, 25, 30, 40, or 50 fold. For example, the anti-ZNT8 antibody or antigen-binding fragment thereof can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-ZNT8 antibody or antigen-binding fragment thereof can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies or fragments can be prepared by performing chemical modifications on the antibodies or the lower molecular weight forms thereof described herein. Methods for modifying antibodies are well known in the art.

II. Characterization of Antibodies

The ZNT8 binding properties of the antibodies described herein may be measured by any standard method, e.g., one or more of the following methods: OCTET®, Surface Plasmon Resonance (SPR), BIACORE™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-ZNT8 antibody or functional fragment thereof) and a target (e.g., ZNT8) can be analyzed using the OCTET® systems. In this method, one of several variations of instruments (e.g., OCTET® QKe and QK), made by the ForteBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-ZNT8 antibody or functional fragment thereof) and a target (e.g., ZNT8) can be analyzed using Surface Plasmon Resonance (SPR). SPR or Biomolecular Interaction Analysis (BIA) detects biospecific interactions in real time, without labeling any of the interactants.

Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which is measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem 63:2338-2345; Szabo et al. (1995) Curr. Opin. Struct. Biol. 5:699-705 and on-line resources provide by BIAcore International AB (Uppsala, Sweden). Information from SPR can be used to provide an accurate and quantitative measure of the equilibrium dissociation constant (Kd), and kinetic parameters, including Kon and Koff, for the binding of a biomolecule to a target.

Epitopes can also be directly mapped by assessing the ability of different anti-ZNT8 antibodies or functional fragments thereof to compete with each other for binding to human ZNT8 using BIACORE chromatographic techniques (Pharmacia BIAtechnology Handbook, "Epitope Mapping", Section 6.3.2, (May 1994); see also Johne et al. (1993) J. Immunol. Methods, 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in Antibodies: A Laboratory Manual, ed. by Harlow and Lane, Cold Spring Harbor press (1988)).

III. Affinity Maturation

In one embodiment, an anti-ZNT8 antibody or antigen-binding fragment thereof is modified, e.g., by mutagenesis, to provide a pool of modified antibodies. The modified antibodies are then evaluated to identify one or more antibodies having altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used. Methods of effecting affinity maturation include random mutagenesis (e.g., Fukuda et al., *Nucleic Acids Res.*, 34:e127 (2006); targeted mutagenesis (e.g., Rajpal et al., *Proc. Natl. Acad. Sci. USA*, 102:8466-71 (2005); shuffling approaches (e.g., Jermutus et al., *Proc. Natl. Acad. Sci. USA*, 98:75-80 (2001); and in silico approaches (e.g., Lippow et al., *Nat. Biotechnol.*, 25: 1171-6 (2005).

In some embodiments, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criterion for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

Calculations of "sequence identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.*, 22:259-306. Removal of any carbohydrate moieties present on the antibodies may be accomplished chemically or enzymatically as described in the art (Hakimuddin et al. (1987) *Arch. Biochem. Biophys.*, 259:52; Edge et al. (1981) *Anal. Biochem.*, 118:131; and Thotakura et al. (1987) *Meth. Enzymol.*, 138:350). See, e.g., U.S. Pat. No. 5,869,046 for a modification that increases in vivo half-life by providing a salvage receptor binding epitope.

In one embodiment, an anti-ZNT8 antibody has one or more CDR sequences (e.g., a Chothia, an enhanced Chothia, or Kabat CDR) that differ from those described herein. In one embodiment, an anti-ZNT8 antibody has one or more CDR sequences include amino acid changes, such as substitutions of 1, 2, 3, or 4 amino acids if a CDR is 5-7 amino acids in length, or substitutions of 1, 2, 3, 4, or 5, of amino acids in the sequence of a CDR if a CDR is 8 amino acids or greater in length. The amino acid that is substituted can have similar charge, hydrophobicity, or stereochemical characteristics. In some embodiments, the amino acid substitution(s) is a conservative substitution. A "conservative amino acid substitution" is one in which the amino acid residue is replaced with an amino acid residue having a side chain with a similar charge. Families of amino acid residues having side chains with similar charges have been defined in the art.

These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). In other embodiments, the amino acid substitution(s) is anon-conservative substitution. The antibody or antibody fragments thereof that contain the substituted CDRs can be screened to identify antibodies of interest.

Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al., *J Immun.*, 147:26S7-62 (1991); Morgan et al., *Immunology*, 86:319-24 (199S)), or changing the species from which the constant region is derived.

IV. Methods of Producing Anti-ZNT8 Antibodies

The anti-ZNT8 antibodies (or antigen binding domain(s) of an antibody or functional fragment thereof) of this disclosure may be produced in bacterial or eukaryotic cells. To produce the polypeptide of interest, a polynucleotide encoding the polypeptide is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5a, HB1O1, or XL I-Blue is used as a host, the vector must have a promoter, for example, a lacZ promoter (Ward et al., 341: 544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-l (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, 293, 293T, and NIH3T3 cells, the expression vector includes a promoter necessary for expression in these cells, for example, an SV40 promoter (Mulligan et al., Nature, 277:108 (1979)), MMLV-LTR promoter, EF1a promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, the antibodies are produced in mammalian cells. Exemplary mammalian host cells for expressing a polypeptide include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

The antibodies of the present disclosure can be isolated from inside or outside (such as medium) of the host cell and purified as substantially pure and homogenous antibodies. Methods for isolation and purification commonly used for polypeptides may be used for the isolation and purification of antibodies described herein, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

The present disclosure also provides a nucleic acid molecule or a set of nucleic acid molecules encoding an anti-ZNT8 antibody or antigen binding molecule thereof disclosed herein. In one embodiment, the invention includes a nucleic acid molecule encoding a polypeptide chain, which comprises a light chain of an anti-ZNT8 antibody or antigen-binding molecule thereof as described herein. In one embodiment, the invention includes a nucleic acid molecule encoding a polypeptide chain, which comprises a heavy chain of an anti-ZNT8 antibody or antigen-binding molecule thereof as described herein.

Also provided are a vector or a set of vectors comprising such nucleic acid molecule or the set of the nucleic acid molecules or a complement thereof, as well as a host cell comprising the vector.

The instant disclosure also provides a method for producing a ZNT8 or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a ZNT8 antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

For recombinant production, a polynucleotide sequence encoding a polypeptide (e.g., a ZNT8 antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a ZNT8 antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO J. 1:841). A variety of host-expression vector systems can be utilized to express the polypeptides described herein (e.g., a ZNT8 antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a ZNT8 antibody or antigen-binding molecule thereof disclosed herein, or any of the chimeric molecules disclosed herein) can also code for a signal sequence that will permit the polypeptide to be secreted. One skilled in the art will understand that while the polypeptide is translated, the signal sequence is cleaved by the cell to form the mature chimeric molecule. Various signal sequences are known in the art and familiar to the skilled practitioner. Alternatively, where a signal sequence is not included, the polypeptide (e.g., a ZNT8 antibody or antigen-binding molecule thereof disclosed herein, or any of the chimeric molecules disclosed herein) can be recovered by lysing the cells.

V. Pharmaceutical Compositions

The present disclosure also provides pharmaceutical compositions comprising one or more of: (i) a ZNT8 antibody or antigen-binding molecule thereof disclosed herein; (ii) a nucleic acid molecule or the set of nucleic acid molecules encoding a ZNT8 antibody or antigen-binding molecule as disclosed herein; or (iii) a vector or set of vectors disclosed herein, and a pharmaceutically acceptable carrier.

Anti-ZNT8 antibodies or fragments thereof described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, an antibody described herein is formulated with excipient materials, such as sodium citrate, sodium dibasic phosphate heptahydrate, sodium monobasic phosphate, Tween®-80, and a stabilizer. It can be provided, for example, in a buffered solution at a suitable concentration and can be stored at 2-8° C. In some other embodiments, the pH of the composition is between about 5.5 and 7.5 (e.g., 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, and 7.5).

The pharmaceutical compositions can also include agents that reduce aggregation of the antibody when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization.

Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibodies may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

In one embodiment, the pharmaceutical formulation comprises an antibody at a concentration of about 0.005 mg/mL to 500 mg/mL (e.g., 0.005 mg/ml, 0.01 mg/ml, 0.05 mg/ml, 0.1 mg/ml, 0.5 mg/mL, 1 mg/mL, 5 mg/mL, 10 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 250 mg/mL, 300 mg/mL, 350 mg/mL, 400 mg/mL, 450 mg/mL, 500 mg/mL), formulated with a pharmaceutically acceptable carrier. In some embodiments, the antibody is formulated in sterile distilled water or phosphate buffered saline. The pH of the pharmaceutical formulation may be between 5.5 and 7.5 (e.g., 5.5, 5.6, 5.7, 5.8, 5.9, 6.0, 6.1, 6.2 6.3, 6.4 6.5, 6.6 6.7, 6.8, 6.9 7.0, 7.1, 7.3, 7.4, 7.5).

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

A. Administration

The antibodies or antigen-binding fragment thereof, or nucleic acids encoding same of the disclosure can be administered to a subject, e.g., a subject in need thereof, for example, a human or animal subject, by a variety of methods. For many applications, the route of administration is one of: intravenous injection or parenteral, infusion (IV), subcutaneous injection (SC), intraperitoneally (IP), or intramuscular injection, intratumor (IT). Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrastemal injection.

In one embodiment, the route of administration of the antibodies of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g., acetate, phosphate or citrate buffer), a surfactant (e.g., polysorbate), optionally a stabilizer agent (e.g., human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization.

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The route and/or mode of administration of the anti-ZNT8 antibody or fragment thereof can also be tailored for the individual case, e.g., by monitoring the subject.

The antibody or fragment thereof can be administered as a fixed dose, or in a mg/kg dose. The dose can also be chosen to reduce or avoid production of antibodies against the anti-ZNT8 antibody or fragment thereof. Dosage regimens are adjusted to provide the desired response, e.g., a therapeutic response or a combinatorial therapeutic effect. Generally, doses of the antibody or fragment thereof (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In certain embodiments, a subject in need of treatment with an antibody or fragment thereof is administered the antibody or fragment thereof at a dose of between about 1 mg/kg to about 30 mg/kg. In some embodiments, a subject in need of treatment with anti-ZNT8 antibody or fragment thereof is administered the antibody or fragment thereof at a dose of 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In a specific embodiment, the antibody or fragment thereof is administered subcutaneously at a dose of 1 mg/kg to 3 mg/kg. In another embodiment, the antibody or fragment thereof is administered intravenously at a dose of between 4 mg/kg and 30 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of the antibody or fragment thereof.

Dosage unit form or "fixed dose" as used herein refers to physically discrete units suited as unitary dosages for the subjects to be treated; each unit contains a predetermined quantity of antibody or fragment thereof calculated to produce the desired therapeutic effect in association with the required pharmaceutical carrier and optionally in association with the other agent. Single or multiple dosages may be given. Alternatively, or in addition, the antibody or fragment thereof may be administered via continuous infusion.

An antibody or fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the stage or severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein, the antibody or fragment thereof can be administered before the full onset of the disorder, e.g., as a preventative measure. The duration of such preventative treatment can be a single dosage of the antibody or fragment thereof or the treatment may continue (e.g., multiple dosages). For example, a subject at risk for the disorder or who has a predisposition for the disorder may be treated with the antibody or fragment thereof for days, weeks, months, or even years so as to prevent the disorder from occurring or fulminating.

In certain embodiments, the antibody or fragment thereof is administered subcutaneously at a concentration of about 1 mg/mL to about 500 mg/mL (e.g., 1 mg/mL, 2 mg/mL, 3 mg/mL, 4 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 400 mg/mL, 450 mg/mL). In one embodiment, the anti-ZNT8 antibody or fragment thereof is administered subcutaneously at a concentration of 50 mg/mL. In another embodiment, the antibody or fragment thereof is administered intravenously at a concentration of about 1 mg/mL to about 500 mg/mL. In one embodiment, the antibody or fragment thereof is administered intravenously at a concentration of 50 mg/mL.

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

VI. Devices and Kits for Therapy

An anti-ZNT8 antibody or fragment thereof can be provided in a kit. In one embodiment, the kit includes (a) a container that contains a composition that includes an anti-ZNT8 antibody or fragment thereof as described herein, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein. For example, the kit includes a first container that contains a composition that includes the anti-ZNT8 antibody or fragment thereof, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-ZNT8 antibody or fragment thereof, e.g., in a suitable dose, dosage form, or mode of administration (e.g., a dose, dosage form, or mode of administration described herein), to treat a subject who has had or who is at risk for a disease as described herein. The information can be provided in a variety of formats, include printed text, computer readable material, video recording, or audio recording, or information that provides a link or address to substantive material, e.g., on the internet.

In addition to the anti-ZNT8 antibody or fragment thereof, the composition in the kit can include other ingredients, such as a solvent or buffer, a stabilizer, or a preservative. The anti-ZNT8 antibody or fragment thereof can be provided in any form, e.g., liquid, dried or lyophilized form, preferably substantially pure and/or sterile. When the agents are provided in a liquid solution, the liquid solution preferably is an aqueous solution. In certain embodiments, the anti-ZNT8 antibody or fragment thereof in the liquid solution is at a concentration of about 25 mg/mL to about 250 mg/mL (e.g., 40 mg/mL, 50 mg/mL, 60 mg/mL, 75 mg/mL, 85 mg/mL, 100 mg/mL, 125 mg/mL, 150 mg/mL, and 200 mg/mL). When the anti-ZNT8 antibody or fragment thereof is provided as a lyophilized product, the anti-ZNT8 antibody or fragment thereof is at about 75 mg/vial to about 200 mg/vial (e.g., 100 mg/vial, 108.5 mg/vial, 125 mg/vial, 150 mg/vial). The lyophilized powder is generally reconstituted by the addition of a suitable solvent. The solvent, e.g., sterile water or buffer (e.g., PBS), can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-ZNT8 antibody or fragment thereof and the second agent, e.g., in a desired ratio. For example, the kit includes a plurality of syringes, ampules, foil packets, blister packs, or medical devices, e.g., each containing a single combination unit dose. The containers of the kits can be airtight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

As described below, the present inventors identified two mAbs (mAb20, mAb39) through a multitier screening against purified human ZnT8 in its native conformations. Detailed mAb characterization revealed distinct binding properties and specificities with a common ability to stabilize ZnT8 structural folding, and consequently, inhibit its transport activity by slowing down the zinc turnover rate. These findings demonstrate the utility of mAbs as allosteric inhibitors of human ZnT8. The present inventors also identified a stable ternary complex of a ZnT8 monomer with two distinct Fabs. The ZnT8-mediated proximity of two mAbs allowed for ZnT8 quantification based on a FRET signal between a pair of donor and acceptor fluorophores covalently linked to bound mAbs. In this assay, we used a caged lanthanide donor (terbium cryptate) that is characterized by a long fluorescence emission half-life. The FRET signal derived from the ternary complex can be obtained using a delayed fluorescence measurement after the decay of the short-lived background fluorescence. Thus, the assay can be performed in a homogeneous format without the need to separate the binding complex from unbound mAbs (30). This simple add-and-read HTRF assay highlights another utility of mAbs as a ZnT8-specific biosensor.

Materials and Methods

Generating hybridoma. Four pairs of male/female homozygous Slc30a8−/− mice were immunized by weekly intraperitoneal injections of a human ZnT8 antigen (the R325 variant) in reconstituted proteoliposomes. All experiments with mice were approved by the Institutional Animal Care and Use Committee of Johns Hopkins University School of Medicine. Serum antibody titering and validation of anti-ZnT8 specificity by CRISPR/Cas9 ZnT8-knockout were described previously (36). Following a final immunization boost, spleens were isolated. Splenocytes were fused with an immortalized myeloma cell line Sp2/0-Ag14 (CRL-1581, ATCC) at a 4:1 splenocytes-to-myeloma ratio by adding 1 ml of 50% PEG1500 (w/v, Roche) to the cell mixture drop-by-drop over 1 min (37). The cells stayed in the PEG solution for one more minute with gentle mixing, and then 20 ml serum free DMEM was added in a stepwise fashion over 4-5 min. Cells were pelted, and then resuspended in 15 ml DMEM with 10% FBS supplemented with Hybridoma Fusion and Cloning Supplement (HFCS) and hypoxanthine, aminopterin and thymidine (HAT). Eight days after fusion, dead Sp2/0 cells were removed, and hybridoma cells were plated in 96 well plates at a density of ~5 cells per well and maintained under HAT selection.

Screening hybridoma. Multiter ELISAs were developed to evaluate hybridoma supernatants. First screening used native human ZnT8 antigen in reconstituted proteoliposome by passive coating (200 ng ZnT8/well). The coated plates were pre-blocked with 5% BSA in an assay buffer (20 mM HEPES, 100 mM NaCl, pH7.0), and then 20 µl hybridoma supernatant was added to each well, incubated at RT for 2 hr, and then washed three times with assay buffer plus 1% BSA. Bound antibodies were detected by an HRP-conjugated goat anti-mouse secondary antibody (Invitrogen, cat. #62-6500) with 1:3000 dilutions in assay buffer, followed by ABTS colorimetric reaction (Life Technologies) and signal readout at 415 nm on a plate reader (Molecular Device). Second screening used a native CTD-His monomer by affinity binding to Ni-NTA plates (100 ng CTD/well). ELISA procedures were the same as above. Third screening used native ZnT8 in detergent micelles. The antigen was bound between two layers of antibodies: the capture antibody was mAb20 immobilized to protein A/G plates (800 ng/well). Only a detection antibody bound to a non-overlapping epitope gave a positive ELISA readout. Purified MSA and commercial NTDA (Proteintech, cat. #16169-I-AP) and CTDA (Amgen) were used as negative and positive controls to calibrate ELISA dynamic range and sensitivity.

Validating mAbs. Monoclonal hybridoma cell lines were established by flow cytometry single-cell sorting to ensure clonal purity. After clonal expansion, secreted mAbs were purified by protein-A/G affinity chromatography (Thermo Scientific, cat. #20423), subtyped (Thermo Scientific, cat. #37503), and then Fab fragments were prepared by papain digestion (Thermo Scientific, cat. #44985). Purified mAbs or Fabs were tested for: (i) formation of binding complexes with purified ZnT8 or ZnT8-GFP on size-exclusion HPLC, (ii) immunofluorescence staining of HEK293 cells w/o ZnT8 expression followed by confocal microscopy imaging, (iii) immunofluorescence staining of bulk cell population followed by flow cytometry quantitation, and (iv) formation of Fab-ZnT8 complexes by negative staining EM and single particle analysis.

Fluorescence size-exclusion HPLC. Purified mAb20/Fab20 or mAb39 was mixed with Alexa Fluor 488 or Alexa Fluor 555 carboxylic acid succinimidyl ester in a 1:20 molar ratio in PBS buffer for 60 min at RT, and then the labeling reaction was terminated by 100 mM Tris-HCL quenching. The fluorescently labelled mAb or Fab was HPLC purified to remove trace amount of free fluorescent dyes, concentrated to 1 mg/ml for storage in PBS buffer at 4° C. Purified human ZnT8 in detergent micelles was incubated with mAb20/Fab20 or mAb30 for 2 hr, centrifuged at 258,000×g for 30 min to precipitate crosslinked ZnT8 aggregates, and then injected into a TSKgel G3000SWXL size exclusion HPLC column (Tosoh Biosciences) preequilibrated with the assay buffer plus 0.02% DDM. Alternatively, ZnT8-GFP in detergent crude extract of INS-1E cells stably expressing human ZnT8 was purified by GFP-fluorescence sizing-HPLC. Next, the peak fraction of ZnT8-GFP was incubated with mAb20 or mAb39 for 3 hr at 4° C., centrifuged to remove crosslinked aggregates, and then injected into the TSK column as above. The elution profile was monitored using a multichannel fluorescence detector with the following excitation/emission pairs: 480/520, 485/555, 480/520 nm for Alexa Fluor 488, Alexa Fluor 555 and GFP fluorescence, respectively. ZnT8 peak alone was monitored by a UV detector in line with the fluorescence detector.

Negative staining electron microscopy. Human ZnT8 was purified as described previously (20). Fab20 or Fab20+Fab39 was added to ZnT8 in a 10:1 molar ratio. The binding complexes were re-purified by size-exclusion HPLC and concentrated to 1-2 mg/ml. The protein samples were diluted to 20 µg/ml, and aliquots of 3 µl diluted sample were applied on glow-discharged EM grids covered with a continuous thin carbon film and stained by 2% uranyl acetate aqueous solution for 1.5 min. Grids were loaded onto a Tecnai Spirit electron microscope operated at a high tension of 120 kV. Raw images were collected in low-dose mode (10 e/Å) using a Gatan Orius CCD camera with a underfocus value ranging from 1 µm to 2.5 µm and at a magnification of 30,000, corresponding to 2.1 Å/pixel at the specimen level. We recorded 221 and 71 micrographs for the binary (Fab20)$_2$-ZnT8 and ternary (Fab20)$_2$-ZnT8-(Fab39)$_2$ complexes, respectively. The contrast transfer function parameters of each image were determined by CTFFIND4.1.5 (38). 76,274 binary and 6,107 ternary particles were picked from the micrographs. After 2D classification in RELION2.1.0 (39) and 3D classification in cryoSPARC (40), 15,745 binary particles and 2,369 ternary particles were retained for 3D reconstruction. 3D refinement was performed using cryoSPARC. Both binary and ternary complex maps had an estimated resolution of 3 nm. Crystal structures of a Fab targeting *Shigella flexneri* Y Lipopolysaccharide (PDB ID 1M71) (41) and an *E. coli* zinc transporter YiiP (PDB ID 3H90) (29) were used to dock the 3D maps in UCSF Chimera (42).

Immunofluorescence staining and cell imaging. Flp-In, T-REx-HEK293 cells stably expressing human ZnT8 variants were grown and induced on coverslips at 50% confluence as described previously (20). Cell were fixed (R&D Systems, cat. #FC004), permeabilized (R&D Systems, cat. #FC005). HEK293 cells were stained with mAb20 or mAb39 at a 1:3000 dilution from a 1 mg/ml mAb stock while EndoC-βH cells at 1:1000 dilution from the same batch of mAb20 and mAb39. Parental Flp-In, T-REx-HEK293 cells without ZnT8 expression were used as a negative control following the identical procedure. A goat-anti-mouse secondary antibody conjugated with Alexa Fluor-594 (Thermo Scientific, cat. #A11005, dilution 1:1000) and DAPI were used for fluorescence imaging on a Zeiss LSM 700 inverted confocal microscope with a 63× oil objective as described previously (20).

Flow cytometry analysis. HEK293 cells w/o ZnT8 overexpression were fixed, permeabilized, and resuspended in PBS plus 5% BSA at a density of 1×10$^6$/ml as described previously (43). Aliquots of 100 µl cell suspension were stained with mAb20 or mAb39 in 3-fold serial dilutions for 2 hours at RT, and then stained with Alexa fluor 647-conjugated donkey-anti-mouse secondary antibody in 1:1000 dilution with 5% BSA (Thermo Fisher Scientific, cat.

A31571). The labeled cells were analyzed immediately by flow cytometry. Cells gated on forward and side scatter revealed a single population represented in a histogram of ~3000 cell counting events. The average immunofluorescence intensity and standard error were obtained using the flow cytometry analysis software Summit 4.3 (Beckman Coulter). EndoC-βH cells and HEK293 cells as ZnT8-KO surrogate were fixed and permeabilized as above, and stained by mAb20 and mAb39 at 1:1000 dilution, followed by secondary antibody staining as described above. The same flow-cytometry protocol was used to analyze labeled EndoC-βH and HEK293 cells.

Immunoblotting. SDS-solubilized cell lysate of EndoC-βH cells or HEK293 cells over-expressing ZnT8 was subjected to SDS-PAGE and probed with a 1:3000 mAb20 or mAb39, followed by 1:3000 anti-mouse HRP-conjugated secondary antibody (GE Healthcare cat. #NA931V). A duplicated gel was Coomassie-stained to show an equal protein loading for each lane (100 µg). To compare the mAb20 or mAb39 reactivities to different ZnT homolog, we used commercial HEK293 lysates with lentivirus-mediated over-expression of ZnT1, ZnT2, ZnT3, ZnT4, ZnT7, ZnT8, ZnT10, each is tagged by a Flag tag at the C-terminus (Origene, catalog nos. LY500001, LC412033, LC423751, LC401170, LY415673, LC428544, LC406320, and LC412886). Approximately equal amounts of total protein (5 µg) was loaded to each lane, and then probed with mAb20, mAb39, or anti-FLAG antibody (Origene, catalog no. TA50011-100) as above. The expression levels of ZnT homologs varied with ZnT1 most abundantly expressed.

Stopped-flow kinetics. As described previously (20), human ZnT8 (the R325 variant) was purified and reconstituted into proteoliposomes with a defined lipid composition of DOPC:DOPG:DOPE (2:1:1) at a protein-to-lipid ratio of 1:50 (wt/wt). Pre-formed proteoliposomes mixed with 200 µM Fluozin-3, w/o 100 µg Fab in 0.2 ml assay buffer underwent three cycles of freeze-thaw, followed by a 10 second sonication to complete encapsulation of dye and Fab. The extravesicular Fluozin-3 was removed by washing vesicles with 3×25 ml assay buffer, and then additional 100 µg Fab was added to ensure saturation of Fab binding. The estimated Fab-to-ZnT8 molar ratio was 2.8:1. ZnT8-mediated zinc transport into proteoliposomes was triggered by a rapid mixing of proteoliposomes and assay buffer on an SFM-3000 stopped-flow apparatus (Bio-logic) as described previously (20). Increasing amount of $ZnSO_4$ was added to the assay buffer with 1 mM sodium citrate that buffered the free zinc concertation from 6 to 116 µM according to maxchelator (maxchelator.stanford.edu). All kinetic traces were cumulative averages of 9 successive recordings. Liposome traces were collected as baselines and subtracted from proteoliposome traces to yield net fluorescence changes ΔF. $\Delta F/\Delta F_{max}$ was obtained by normalizing ΔF to the maximum proteoliposome response elicited by an assay buffer containing 2 mM $ZnSO_4$ plus 2% β-OG. The initial rate of zinc influx was obtained by linear regression of data points (t<10 s) in the quasi-linear phase of the initial fluorescence rise. Concentration dependence data were analyzed by least squares fits of the initial transport rate to a hyperbola defined by $v=V_{max} M/(M+K_m)$, where M represents the free zinc ion concentration, $V_{max}$ is the maximum transport rate when the rate of transport approaches to the quasi-stationary state, and $K_m$ is the Michaelis-Menten constant. Fits of experimental data were preformed using the data analysis software SIGMAPLOT (SPSS Inc.).

HTRF assay. Purified mAb20 and mAb39 were labeled with terbium cryptate and d2 respectively following manufacturer's protocol (Cisbio Bioassays, Bedford, MA). The molecular ratios between molecule and dye in the conjugates are xx for mAb20 and xx for mAb39. The labelled mAbs were HPLC purified in PBS (?), concentrated to 1 mg/ml for storage at 4° C. 293-F cells transiently expressing human ZnT8, human ZnT3 or mouse ZnT8 in suspension culture were harvested. Detergent crude extracts were prepared by 1% DDM solubilization of cell pellet in 20 mM HEPES, 100 mM NaCl, pH 7.0 with protease cocktail, and centrifuged at 16,000 g for 15 min to remove debris. The supernatants were collected for ZnT8 detection. The pellet was solubilized by 2% DDM in PBS, and crude extract was clear of debris for ZnT8 detection. The HTRF assays were performed in 384-well plates (Greiner Bio-one, catalog no. 784075) by adding labeled mAb20, mAb39 in a 1:1 ratio and detergent extract of 293-F cells or EndoC-βH cells in proper dilutions to a total volume of 20 µl. After mAb binding for 2 h at room temperature, fluorescence emissions were measured using a microplate reader (Molecular Devices) equipped with a flash lamp for a 40 µs delayed fluorophore excitation at 340 nm, a 620 nm filter for Terbium cryptate fluorescence reading, and a 665 nm filter for the d2 fluorescence detection. Data were reduced as a ratio of fluorescence measured at 665 nm (d2) and 620 nm (Terbium cryptate) with the signal at 620 nm used as an internal standard. The ratiometric measurement corrected for well-to-well variability and signal quenching from potential interfering components in the binding mix. Background signal was measured and used to calculate the relative ZnT8 readout ΔF for inter-assay comparisons: $\Delta F=(Ratio_{sample}-Ratio_{background})/Ratio_{background}$. The actual ZnT8 concentrations in the assay were estimated based on the ZnT8 yield of 293-F cell transient expression, correlated to the HTRF readouts by linear regression ($r^2=0.99$) to yield a standard curve. LoD and LoQ values were obtained by interpolation of measured datapoints on the standard curve. The Z'-factor values for the HTRF assay was calculated by comparing multiple replicates of HTRF readouts of detergent crude extracts collected from EndoC-βH, HEK293 and INS-1E cells in a single experiment as described previously (44).

Results

Identifying distinct anti-ZnT8 mAbs. Human ZnT8 (B-form) is a homodimer of two 35.1 kDa protomers, each consisted of a 23.8-kDa transmembrane domain (TMD) followed by a 11.3-kDa CTD. A ZnT8 homodimer is referred to as ZnT8 thereafter. Immunization of ZnT8-KO mice with purified human ZnT8 in proteoliposomes yielded serum antibodies that exhibited a ~100-fold increase in antibody titers compared to titers of two commercial antibodies directed to linear peptide sequences from N- and C-terminal domain (NTD and CTD), respectively (31). Splenocytes of immunized mice were isolated and fused with myeloma cells to establish immortalized hybridomas. Preliminary screening by enzyme linked immunosorbent assay (ELISA) identified anti-ZnT8 antibodies that showed different reactivities towards a full-length ZnT8 antigen in proteoliposomes and a monomeric CTD antigen (aa 275-369). These hybridoma cells were subjected to single cell sorting and clonal expansion, and then two secreted monoclonal antibodies (mAb20 and mAb39) were purified for further characterization. Commercial anti-NTD and anti-CTD antibodies (NTDA and CTDA) or purified mouse serum antibodies (MSA) from non-immunized ZnT8-KO mice were used as a positive or negative control. mAb20, mAb39, CTDA and NTDA all yielded positive readouts against a ZnT8 proteoliposome antigen (FIG. 1A). In contrast, only mAb20 and the positive control CTDA recognized a monomeric CTD antigen. mAb39 and the negative control NTDA gave negative results in ELISA probed with CTD (FIG. 1B), suggesting that mAb20 recognized an epitope distinct from that of mAb39.

Stable antibody-ZnT8 complexes. The formation of stable mAb- or Fab-ZnT8 complexes was examined by analytical size-exclusion HPLC. mAbs in excess to ZnT8 tended to form crosslinked protein aggregates. By adjusting the mAb-to-ZnT8 stoichiometry, we detected a series of eight distinct monodisperse peaks as labeled 1-8 in FIG. 2. mAb20 and Fab20 were labeled with a green fluorophore while mAb39 a red fluorophore. mAb20/Fab20 and mAb39 in complex with ZnT8 were monitored in separate channels of a fluorescence detector (FIG. 2). The apparent molecular weight (MW) of each peak was calculated and its predicted complex composition consistent with the MW was summarized in Table-1. For binary binding, Fab20 formed a single (Fab20)$_2$-ZnT8 complex (Peak 3) and mAb20 formed a major mAb20-ZnT8 complex (peak 2). By comparison, mAb39 predominantly formed a (mAb39)$_2$-ZnT8 complex (peak 1) and a secondary mAb39-ZnT8 complex aligning with peak 2. For ternary binding among ZnT8, mAb20/Fab20 and mAb39, both green and red channels recorded similar (mAb39)$_2$-ZnT8-mAb20 (peak 5, 7) and mAb39-ZnT8-(Fab20)$_2$ complexes (peak 6. 8), indicating that mAb20/Fab20 and mAb39 bound independently to a single ZnT8 (peak 4).

TABLE 1

Summary of the Binary and Ternary Complex Peaks

| Peak # | Elution time (min) | Apparent MW (kDa) | Complex composition |
|---|---|---|---|
| 1 | 12.3 | 490 | (mAb39)$_2$ + ZnT8 |
| 2 | 13.5 | 307 | mAb20 + ZnT8 |
| 3 | 13.9 | 260 | (Fab20)$_2$ + ZnT8 |
| 4 | 16.4 | 118 | ZnT8 |
| 5 | 11.7 | 618 | (mAb39)$_2$ + mAb20 + ZnT8 |
| 6 | 12.9 | 388 | mAb39 + (Fab20)$_2$ + ZnT8 |
| 7 | 11.7 | 618 | (mAb39)$_2$ + mAb20 + ZnT8 |
| 8 | 12.9 | 388 | mAb39 + (Fab20)$_2$ + ZnT8 |

Figure 3F:
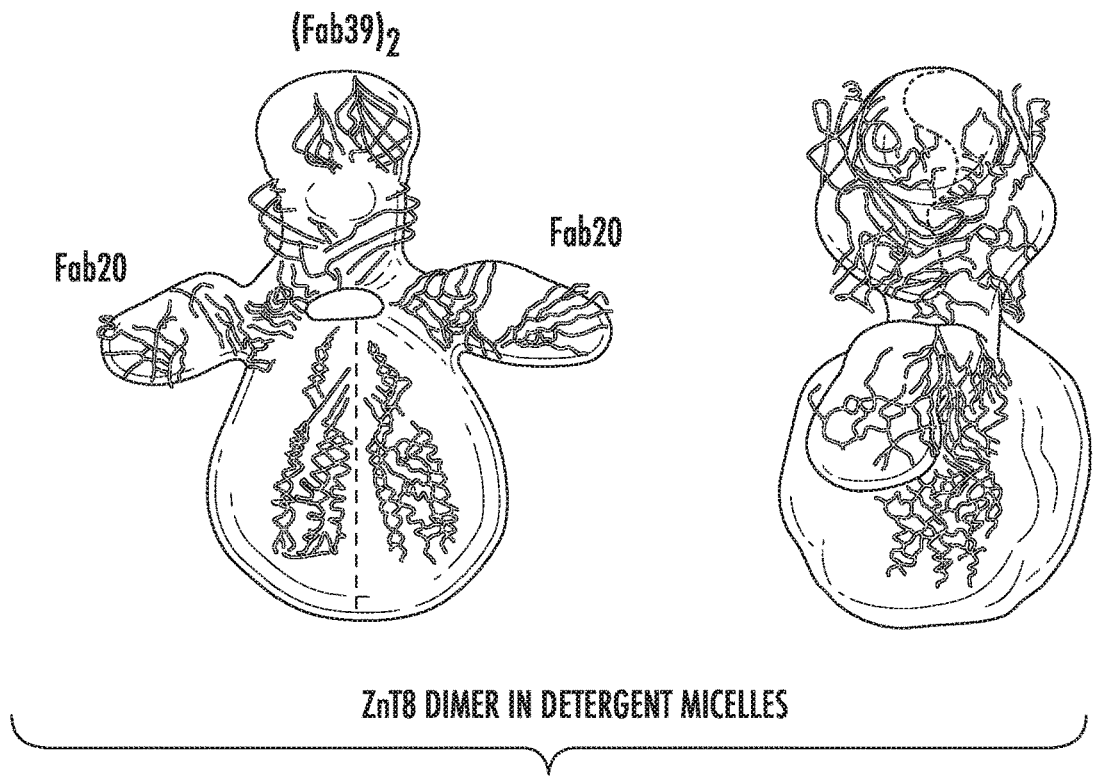

Single particle electron microscopy (EM) analysis. To further characterize antibody binding, we purified the binary (Fab20)$_2$-ZnT8 and ternary (Fab20)$_2$-ZnT8-(Fab39)$_2$ complexes and directly visualized Fab bindings by negative staining EM. The raw images of the binary complex (FIG. 3A), and corresponding 2D reference-free averages revealed two Fabs in one intact complex, each with a characteristic Fab groove that was clearly visible between the variable and constant region (FIG. 3B). Thus, 2-fold symmetry was applied to single particle 3D reconstruction, yielding a low-resolution (~3 nm) 3D map. The 3D envelope was fitted with the crystal structures of two Fab molecules (PDB ID 1M71) and one ZnT8 homolog YiiP (PDB ID 3H90). The ZnT8 envelop was larger than the crystal structure, likely due to the detergent micelles surrounding the transmembrane region (FIG. 3E). For the ternary complex, the raw images revealed bindings of multiple Fab molecules to a single ZnT8 dimer (FIG. 3C). The representative 2D averages also showed multiple Fab bindings (FIG. 3D). 3D reconstructions revealed three discrete protrusions on the CTD surface (FIG. 3F). The two outer protrusions were smaller and in similar but slightly lower positions as observed in ZnT8-(Fab20)$_2$, thus were assigned as a pair of Fab20 molecules (FIG. 3F). The middle protrusion was larger and could be fitted by two Fab molecules straddling the two-fold axis at the ZnT8 dimer interface, and therefore assigned as two Fab39 molecules (FIG. 3F). Although the map resolution was insufficient to distinguish different types of Fabs in the ternary complex, homologue structure docking of the 3-D model suggested that CTD dimerization was required for mAb39 binding. This finding was supported by a negative mAb39 readout in CTD-ELISA against a monomeric CTD antigen (FIG. 1B). By comparison, each Fab20 bound to a separate CTD monomer in the 3-D model (FIG. 3E-F), in agreement with a positive mAb20 readout in CTD-ELISA.

Figure 4A:
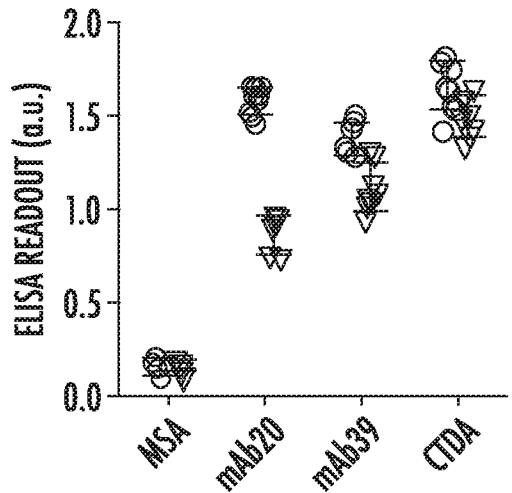
FIG. 4A-4C. mAb binding stabilized ZnT8 folding (FIG. 4A) mAb binding to folded or denatured ZnT8. ZnT8-His in detergent micelles was immobilized to a Ni-NTA plate in replication w/o SDS denaturation. ELISAs against denatured (triangle) and non-denatured ZnT8 (circle) were compared for mAb20 and mAb39 as indicated. CTDA and MSA were used as a positive and negative control, respectively. Error bars are standard deviations.
Figure 4B:
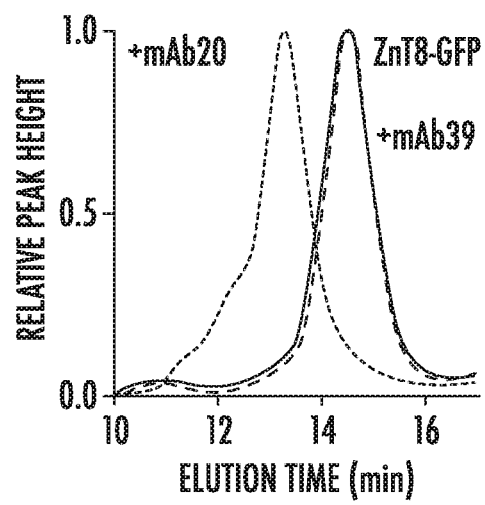

Folding dependence. To compare the difference in mAb bindings to native and denatured ZnT8, we used 2% SDS to unfold immobilized ZnT8-His on a Ni-NTA plate, and then compared denatured ELISA readouts with non-denatured replicates. The native readout of mAb20 was about two-fold higher than the denatured readout (FIG. 4A), indicating a moderate selectivity for folded conformation over unfolded ZnT8. As a control, CTDA reacted with native and denatured ZnT8 indiscriminately. Unexpectedly, mAb39, despite its binding to the dimer interface and anti-CTD negativity (FIG. 1B), was ELISA positive for denatured ZnT8 immobilized to the Ni-NTA plate (FIG. 4A). One possibility was that mAb39 epitope was close to the C-terminus where a pair of His-tags from a ZnT8 dimer might stabilize local dimeric interaction by Ni-NTA binding. To test this hypothesis, we added a bulkier green fluorescence protein (GFP) to the C-terminus and examined its potential steric hindrance to mAb binding. Size-exclusion HPLC showed that mAb20 shifted the ZnT8-GFP peak leftward as predicted for a mAb20-ZnT8-GFP binary complex (FIG. 4B). In contrast, the C-terminal GFP completely blocked the formation of mAb39-ZnT8-GFP binary complex. The steric clash between GFP and mAb39 binding localized the mAb39 binding site to the C-terminus. This result further validated the mAb39 docking to a distal CTD surface straddling the dimer interface (FIG. 3F).

Figure 4C:
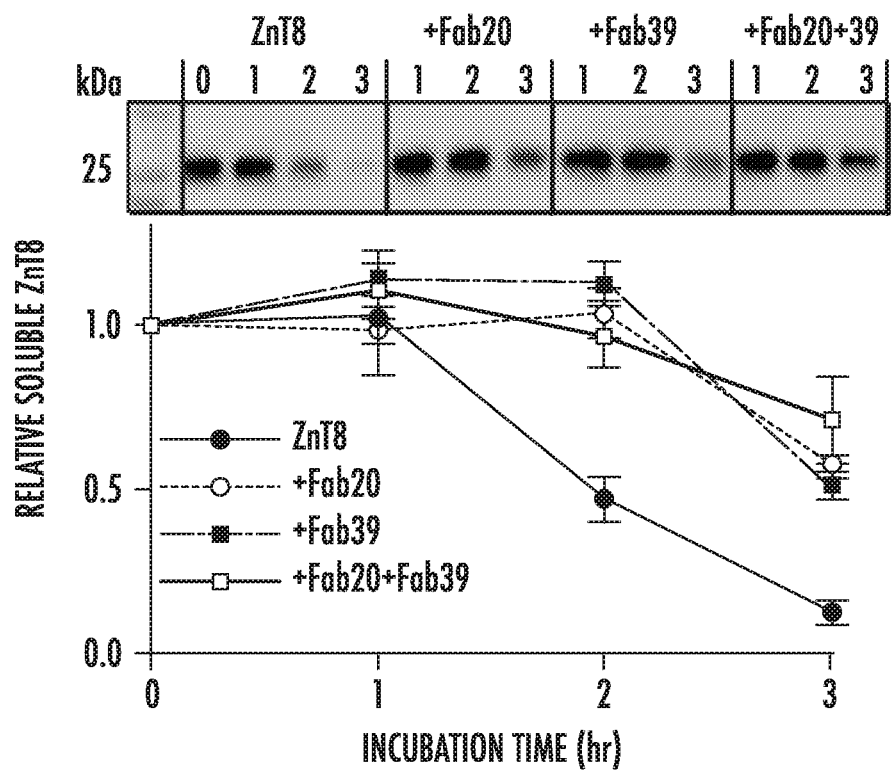

Enhancing ZnT8 stability. mAb binding to a conformational epitope is expected to stabilize the protein folding. Unfolded ZnT8 could be precipitated as protein aggregates by ultracentrifugation. To evaluate the effect of antibody binding on ZnT8 stability, we incubated detergent solubilized ZnT8 with or without a Fab, and then exposed the protein sample to heat denaturation at 37° C. and monitored the folded ZnT8 in the supernatant post-ultracentrifugation. Quantitative immunoblotting showed that ZnT8 was not stable and began to precipitate after one-hour heat exposure (FIG. 4C). Fab20 or Fab39 binding delayed the onset of ZnT8 precipitation to 2 hours, and this protective effect was further augmented by concurrent bindings of Fab20 and Fab39. At 3 hours, only 12% of initial ZnT8 remained in the supernatant while more than 70% of (Fab20)$_2$-ZnT8-(Fab39)$_2$ were still soluble.

Figure 5A:
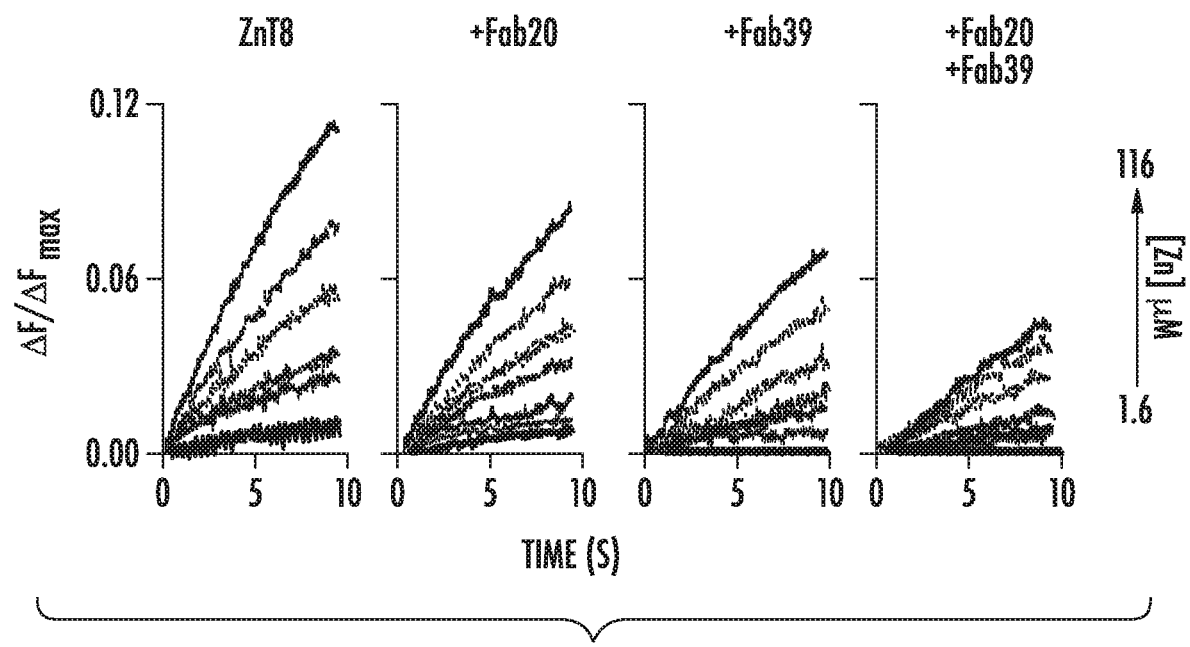
FIG. 5A-5B. Inhibiting zinc transport by Fab binding (FIG. 5A) Fluozin-3 fluorescence traces in response to a rapid mixing of ZnT8 proteoliposomes with an extravesicular zinc buffer. The free zinc concentration in the buffer was increased from 1.6 to 116 µM as indicated by an arrow.
Figure 5B:
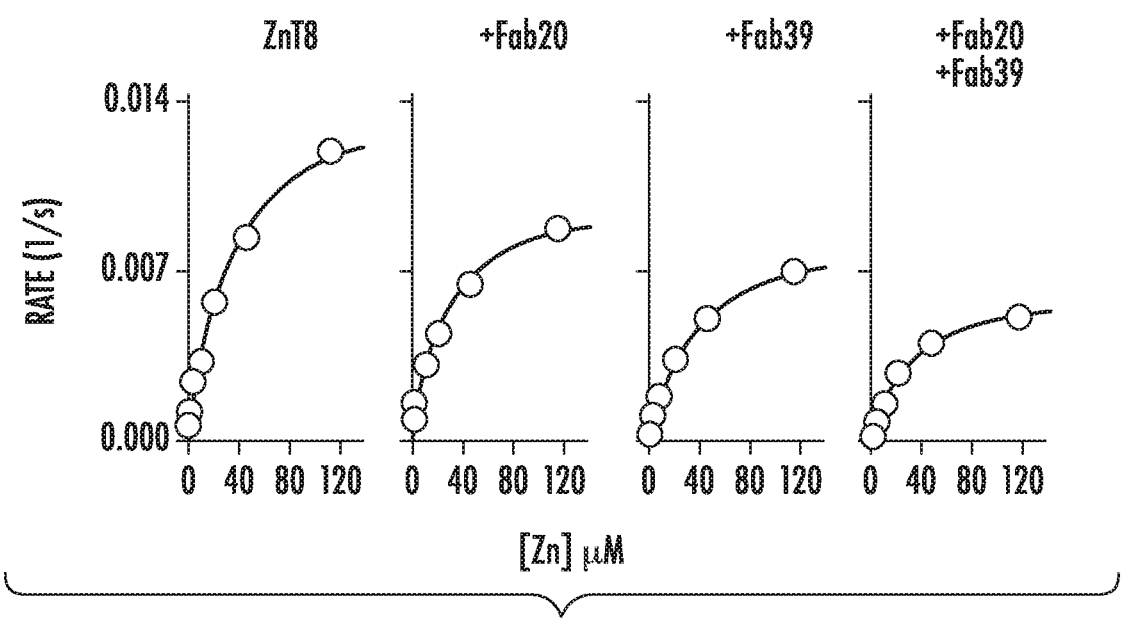

Inhibiting zinc transport. The stabilizing effects of Fab20 and Fab39 suggested that Fab binding trapped ZnT8 in more stable conformations. We further examined the effect of conformational constraints on kinetics of ZnT8-mediated zinc transport. Purified human ZnT8 was reconstituted into proteoliposomes encapsulated with a zinc fluorescent indicator Fluozin-3, and then exposed to a sequence of extravesicular zinc concentrations on a stopped-flow apparatus (FIG. 5A). A fixed 1 mM citrate was added to assay buffers with increasing zinc concentrations, yielding free zinc concentrations from 1.6 to 116 μM. This ensured a constant supply of free zinc to satisfy the steady-state condition. The transmembrane orientations of the reconstituted ZnT8 were estimated to expose 50-75% CTD on the extravesicular side of proteoliposomes based on the difference in mAb immunofluorescence staining between sealed and detergent perforated proteoliposomes. Fab20 or Fab39 was loaded to proteoliposomes with a brief sonication to equilibrate the intra- and extravesicular Fabs. Sizing HPLC of re-solubilized, Fab-treated proteoliposomes confirmed the full occupancy of Fab binding. A rapid mixing of proteoliposomes with a zinc buffer triggered a quasi-linear increase of Fluozin-3 fluorescence within the initial 10 seconds (FIG. 5A). The rate of fluorescence rise was calculated and fitted to the Michaelis-Menten equation (FIG. 5B). The $V_{max}$ and $K_m$ values of the steady-state kinetics were summarized in Table-2, showing a modest reduction (30-41%) of $V_{max}$ by Fab20 or Fab39 as compared with the unbound proteoliposome control. The inhibitory effects of individual Fab bindings were additive, giving a 57% $V_{max}$ reduction when ZnT8 was doubly bound with Fab20 and Fab39. The effect size of Fab inhibition was similar to that of a lower-risk W325 variant, which is ~50% of the higher-risk R325 variant (20). No significant difference was observed for the $K_m$ value, indicating that Fab inhibited ZnT8 by reducing its transport rate.

TABLE 2

Parameters of Steady-State Zinc Transport Kinetics

|  | $V_{max}$ (×0.001 s$^{-1}$) | $K_m$ (μM) |
| --- | --- | --- |
| ZnT8 | 15.0 ± 1.3 | 33.7 ± 7.0 |
| +Fab20 | 10.5 ± 1.0 | 28.6 ± 6.4 |
| +Fab39 | 8.9 ± 0.4 | 36.1 ± 4.1 |
| +Fab20 + Fab39 | 6.4 ± 0.2 | 28.3 ± 2.9 |

Figure 6A:
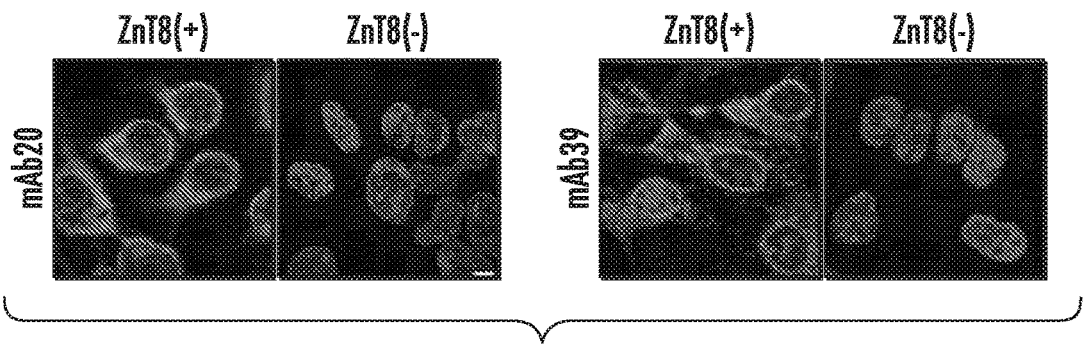
FIG. 6A-6C. mAb binding affinity.
Figure 6B:
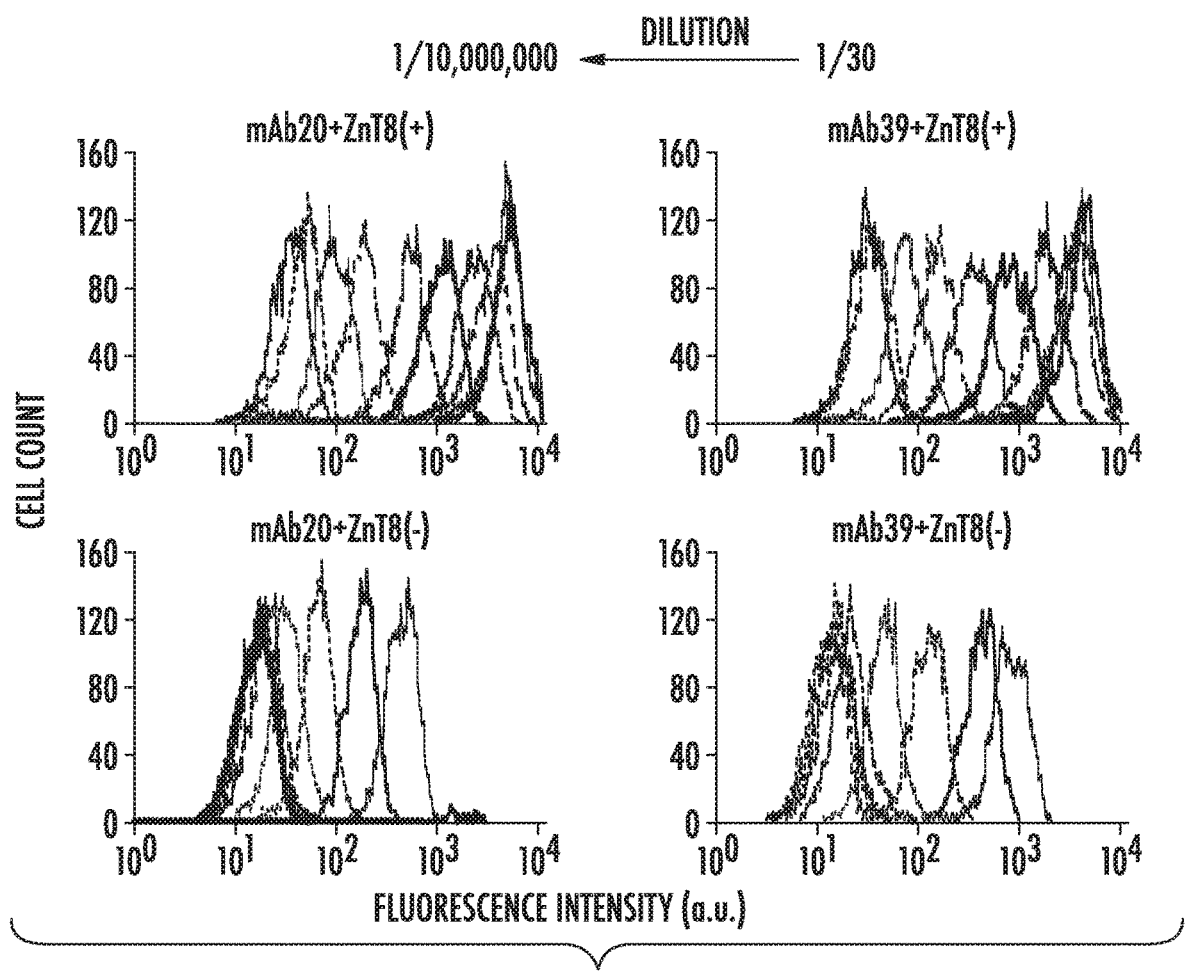
Figure 6C:
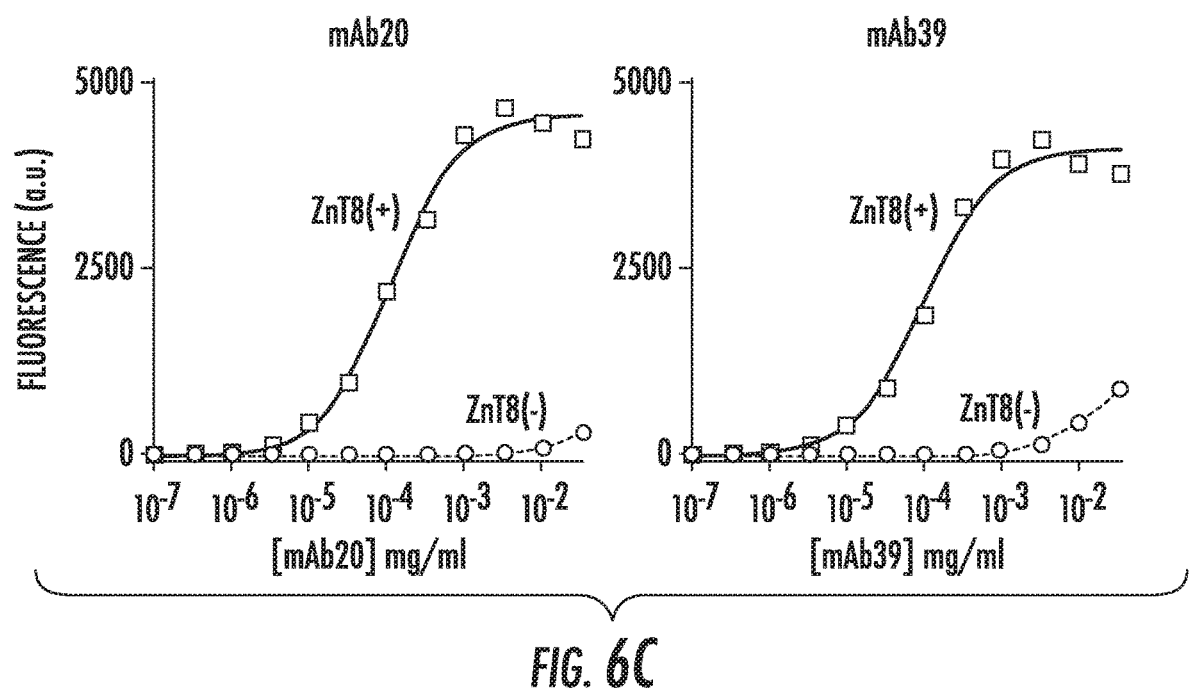

Binding affinity. We examined mAb binding to HEK293 cells stably expressing human ZnT8. Confocal microscopy imaging of immunofluorescence staining with mAb20 and mAb39 revealed strong intracellular signals (FIG. 6A). No mAb staining was detected in parental HEK293 cells without ZnT8 over-expression. Next, we extended the imaging analysis to bulk cell populations using flow cytometry to analyze stably transfected or parental cells labeled with mAb20 or mAb39 in serial dilutions. For each mAb concentration, about 3000 cell counting events were recorded to form a fluorescence intensity histogram (FIG. 6B). mAb dilutions progressively shifted the peak leftward, yielding a quantitative measure of concentration-dependent mAb labeling. mAb20 and mAb39 showed a similar binding profile with an affinity of 0.8±0.1 and 0.7±0.1 nM, respectively (FIG. 6C).

Figure 7A:
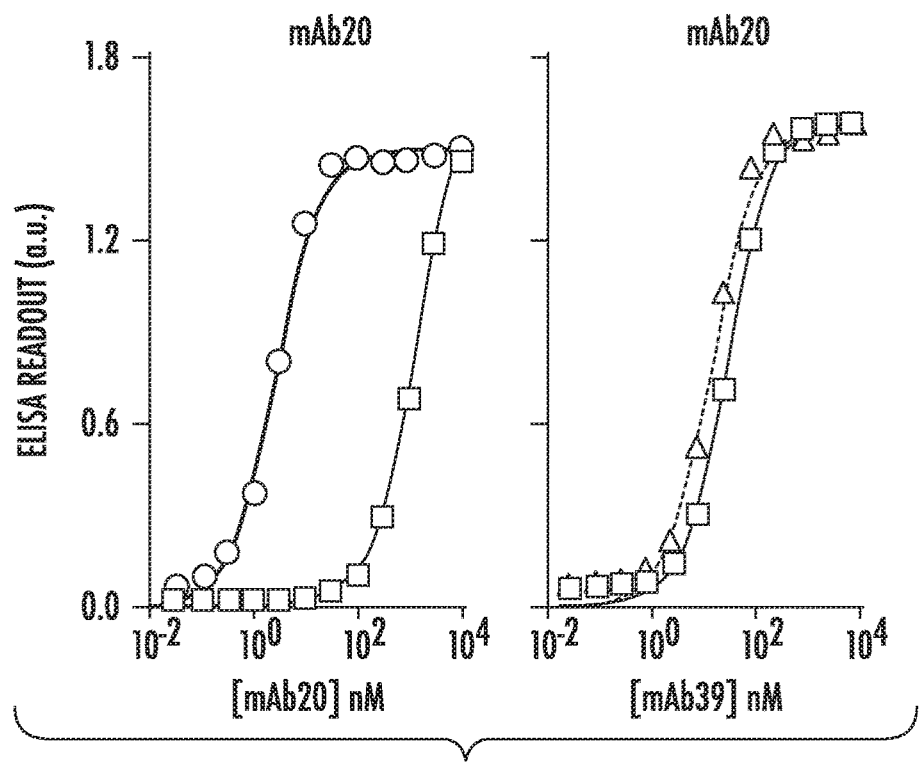
FIG. 7A-7D. mAb binding specificities (FIG. 7A) mAb binding to ZnT8-His immobilized to Ni-NTA plate. Bound mAb20 (red) or mAb39 (magenta) was detected by an HRP-conjugated secondary antibody. Solid lines are least-squares fits of binding datapoints to a one-component binding process. Error bars are standard errors (n=8).
Figure 7B:
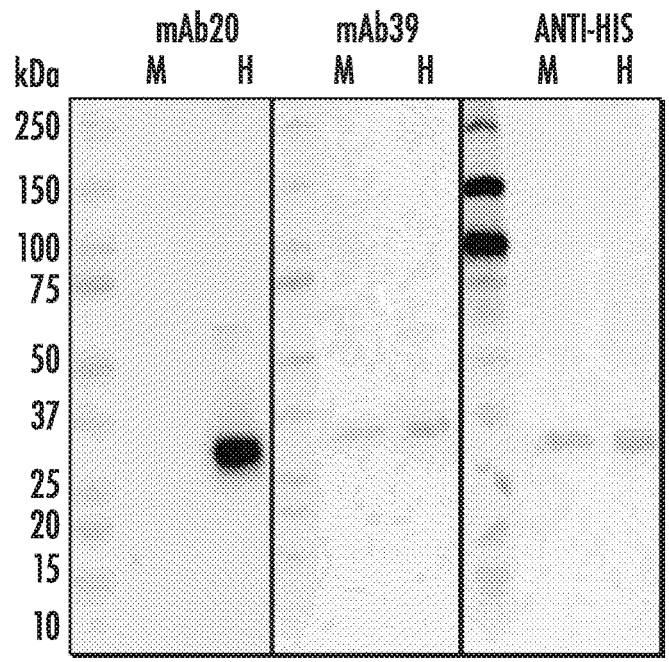
Figure 7C:
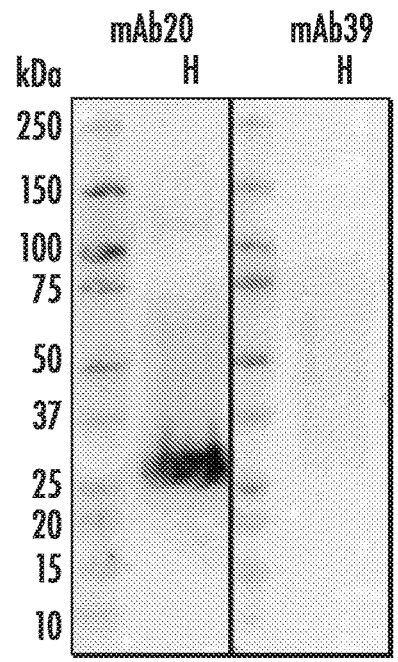
Figure 7D:
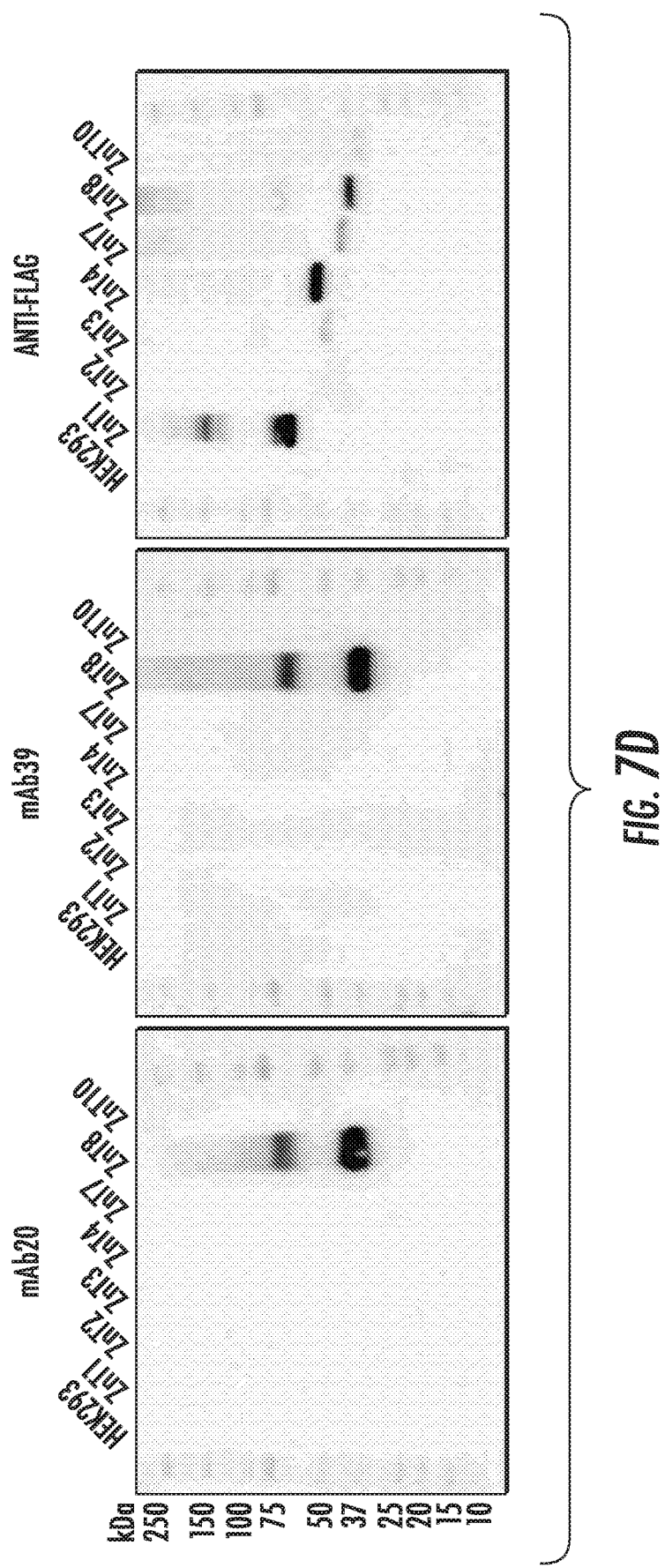

Binding specificities. We first examined the cross-species specificities by comparing mAb bindings to human and mouse ZnT8, both were over-expressed in HEK293 cells, and then solubilized by detergent (DDM) and immobilized to a Ni-NTA plate via a C-terminal poly-histidine tag. mAb titrations with mAb20 revealed a sharp human-mouse difference, shifting the mouse binding curve rightward with a 566.8-fold difference in the apparent binding affinity (2.5±0.2 versus 1422.0±72.6 nM) (FIG. 7A). In contrast, mAb39 binding to human ZnT8 was similar to that of mouse ZnT8 with a marginal 2.0-fold difference (17.6±1.7 versus 35.8±3.0 nM) (FIG. 7A). These results indicated that mAb20 is specific to human ZnT8 while mAb39 recognizes both human and mouse ZnT8. Of note, the epitope-masking effect of ZnT8 immobilization weakened the apparent binding affinities of both mAbs as compared to the affinities determined by flow-cytometry, and such a weakening effect was more pronounced for mAb39, probably due to a closer proximity of the mAb39 epitope to the C-terminal His-tag. Next, we compared the immunoreactivities of mAbs to denatured ZnT8. Immunoblotting lysates of HEK293 transfectants showed that ZnT8 denaturation on SDS-PAGE significantly reduced the immunoreactivities of mAb39 to both human and mouse ZnT8. On the other hand, mAb20 only detected human, but not mouse ZnT8 (FIG. 7B). Both human and mouse ZnT8 were detected at a similar level by an anti-His-tag antibody on a duplicated blot to confirm similar protein loadings (FIG. 7B). The reduction of the mAb39 immunoreactivity was attributed to the loss of ZnT8 dimeric association on SDS-PAGE. Although mAb39 is much weaker than mAb20 for denatured ZnT8 detection, its ZnT8 reactivity seemed comparable to that of commercial antibody to His-tagged ZnT8 on the blots (FIG. 7B). Still next, we used mAbs to probe endogenous ZnT8 expression in EndoC-βH, an insulinoma cell line derived from human pancreatic β-cells (32). Immunoblotting EndoC-βH lysates with mAb20 revealed a single ZnT8 protein band over a negligible background. mAb39 detected neither ZnT8 nor non-specific endogenous protein (FIG. 7C). Finally, we examined mAb20 and mAb39 specificities to ZnT homologs using lysates of HEK293 cells over-expressing ZnT1, ZnT2, ZnT3, ZnT4, ZnT7, ZnT8 or ZnT10, each tagged with a C-terminal FLAG octapeptide. With similar sample loading in each lane, both mAbs detected ZnT8 only (FIG. 7F-G), demonstrating superb selectivities for human ZnT8 against other ZnT homologs.

Figure 8:
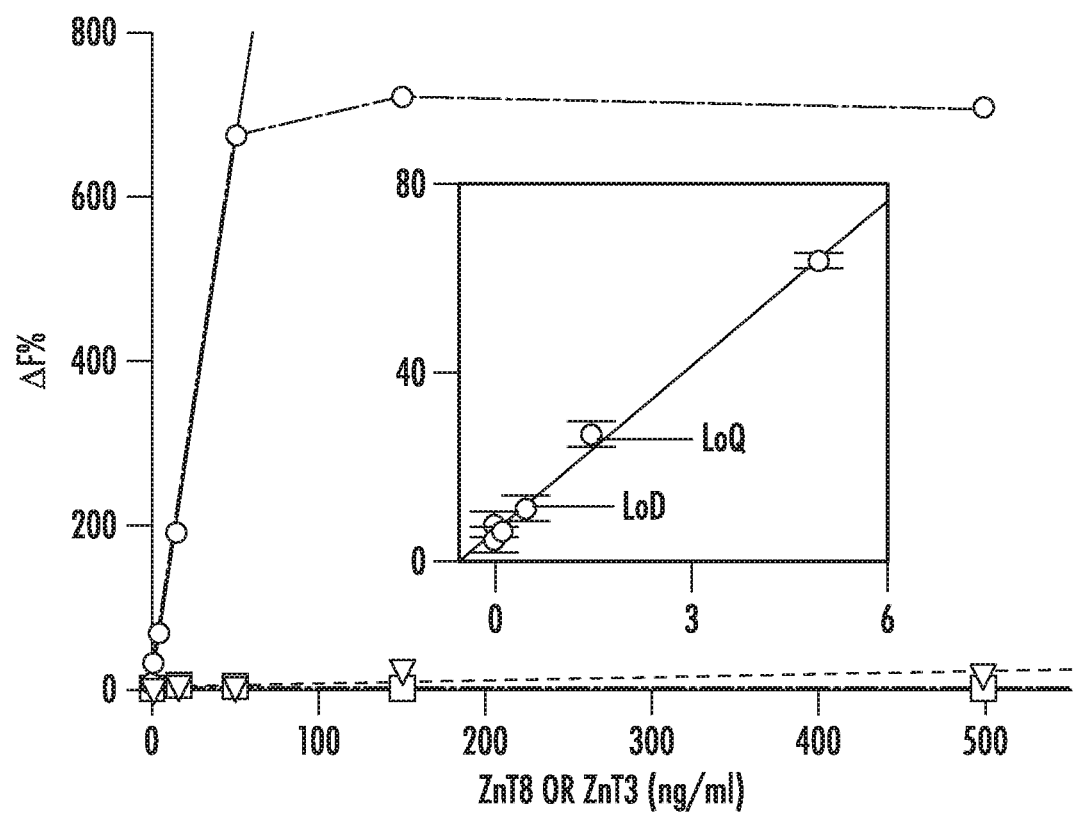
FIG. 8. HTRF response to human ZnT8, mouse ZnT8 and human ZnT3.

Quantifying the cellular ZnT8 level. The co-binding of the mAb20-mAb39 pair to a single ZnT8 protein allowed for quantification of the ZnT8 level by measuring FRET signal derived from labeled fluorescence donor and acceptor in close proximity. mAb20 was labeled with long-emitting terbium cryptate as an energy donor while mAb39 a near-infrared energy acceptor, d2. A fixed amount of donor and acceptor at a 1:1 ratio was added to lysates of HEK293 cells over-expressing human ZnT8, mouse ZnT8 or human ZnT3. HTRF calibration over a range of lysate dilutions revealed a linear HTRF response up to a human ZnT8 concentration of 50 ng/mL, which was then inflected horizontally due to binding saturation (FIG. 8). Mouse ZnT8 or human ZnT3, the closest homolog of human ZnT8, showed negligible or no HTRF response even at a high ZnT concentration of 500 ng/ml. Accordingly, the mouse ZnT8 and human ZnT3 readouts were taken as HTRF background readings. The limit of detection (LoD) for human ZnT8 was 0.51 ng/ml at 3×SD above the background, and the limit of quantification (LoQ) was 1.71 ng/ml at 10×SD above the background (FIG. 8, inset). The coefficient of variance (CV) at LoQ was 9.8%.

Discussion

Unusual biochemical properties of ZnT8 pose significant challenges to developing ZnT8-specific reagents. Until now, all anti-ZnT8 antibodies have been raised against linear epitopes derived from ZnT8 protein sequence, consequently, lacking sufficient specificity for immunodetection of endogenous ZnT8 in pancreatic β-cells. In the present work, we characterize two anti-ZnT8 mAbs raised against full-length human ZnT8 in reconstituted proteoliposomes. Both mAbs recognize folded-ZnT8 with sub-nanomolar binding affinities and are capable of protecting ZnT8 from unfolding and partially inhibiting ZnT8 transport activity. The folding-dependence does not preclude mAbs from recognizing denatured ZnT8 on SDS-PAGE, although the reactivity of mAb39 is greatly reduced. Both mAbs are highly specific for human ZnT8, showing no detectable reactivities to a panel of human ZnT homologs on immunoblots. The specific immunodetection of human ZnT8 is further augmented by simultaneous bindings of two ZnT8-specific mAbs to a single ZnT8 protein. The mAb20-mAb39 pair did not yield a detectable FRET readout for mouse ZnT8 because mAb20 does not recognize mouse ZnT8 (FIG. 7B). Binding of mAb39 alone to mouse ZnT8 (FIG. 7A) failed to elicit a FRET response above LoD of the assay, indicating that the specificity of HTRF detection is a product of multiplying two individual mAb specificities.

The inhibitory effect of Fab binding mirrored the effect of a polymorphic R-to-W substitution at position 325 of human ZnT8. An earlier comparison of steady-state kinetics between the R325 and W325 variants showed that W325 reduced $V_{max}$ by ~50% with no significant effect on $K_m$ (20). The R325W polymorphic variations were localized to a distal dimer interface near the C-terminus based on homology modeling of human ZnT8 (20). Coincidentally, Fab39 appears to bind to the same region by our EM analysis. Functional characterization of polymorphic CTD variants revealed that CTD-W325 had a higher dimerization affinity than CTD-R325 (33), whereas removal of zinc binding to CTD was shown to trigger a hinge-like motion to yield two splayed CTDs (29,34). The W325 variant and Fab39 binding both resulted in stabilization of dimeric interactions, leading to a partial inhibition of the ZnT8 transport activity. Thus, Fab39 binding may mimic the inhibitory effect of the W325 variant by acting on the same allosteric pathway. Our results demonstrate the utility of mAbs as an allosteric inhibitor.

Emerging data suggest that human ZnT8 activity in pancreatic β-cells may be inversely related to the risk of developing T2D (15,20,22). At present, the molecular mechanism underlying the causality between LOF mutations in human ZnT8 and lower T2D risk is still unclear. A mechanistic understanding of this natural protective effect can facilitate translation to novel antidiabetogenic therapies. The allele frequency for the risk R325 is about 72% in the general population (35), but its expression level in human pancreatic islets has yet to be quantified and correlated with the T2D risk. The HTRF assay is highly specific to human ZnT8, accurate and easy to perform in a clinical research setting. This assay may be adapted to measure the abundance of human ZnT8 in healthy and diseased pancreatic islets to correlate the islet ZnT8 expression profile with T2D related clinical metrics. Alteration of the R325 expression is expected to either exacerbate or alleviate hyperactivity of zinc transport. The application of mAbs as a specific ZnT8 biosensor to clinical research may yield new insights into ZnT8 pathophysiology.

REFERENCES

1. Kambe, T., Hashimoto, A., and Fujimoto, S. (2014) Current understanding of ZIP and ZnT zinc transporters in human health and diseases. *Cell Mol Life Sci* 71, 3281-3295
2. Chimienti, F., Devergnas, S., Favier, A., and Seve, M. (2004) Identification and cloning of a beta-cell-specific zinc transporter, ZnT-8, localized into insulin secretory granules. *Diabetes* 53, 2330-2337
3. Lemaire, K., Chimienti, F., and Schuit, F. (2012) Zinc transporters and their role in the pancreatic beta-cell. *J Diabetes Investig* 3, 202-211
4. Segerstolpe, A., Palasantza, A., Eliasson, P., Andersson, E. M., Andreasson, A. C., Sun, X., Picelli, S., Sabirsh, A., Clausen, M., Bjursell, M. K., Smith, D. M., Kasper, M., Ammala, C., and Sandberg, R. (2016) Single-Cell Transcriptome Profiling of Human Pancreatic Islets in Health and Type 2 Diabetes. *Cell Metab* 24, 593-607
5. Chimienti, F., Devergnas, S., Pattou, F., Schuit, F., Garcia-Cuenca, R., Vandewalle, B., Kerr-Conte, J., Van Lommel, L., Grunwald, D., Favier, A., and Seve, M. (2006) In vivo expression and functional characterization of the zinc transporter ZnT8 in glucose-induced insulin secretion. *J Cell Sci.* 119, 4199-4206.
6. Lemaire, K., Ravier, M. A., Schraenen, A., Creemers, J. W., Van de Plas, R., Granvik, M., Van Lommel, L., Waelkens, E., Chimienti, F., Rutter, G. A., Gilon, P., in't Veld, P. A., and Schuit, F. C. (2009) Insulin crystallization depends on zinc transporter ZnT8 expression, but is not required for normal glucose homeostasis in mice. *Proc Natl Acad Sci U S A* 106, 14872-14877
7. Nicolson, T. J., Bellomo, E. A., Wijesekara, N., Loder, M. K., Baldwin, J. M., Gyulkhandanyan, A. V., Koshkin, V., Tarasov, A. I., Carzaniga, R., Kronenberger, K., Taneja, T. K., da Silva Xavier, G., Libert, S., Froguel, P., Scharfmann, R., Stetsyuk, V., Ravassard, P., Parker, H., Gribble, F. M., Reimann, F., Sladek, R., Hughes, S. J., Johnson, P. R., Masseboeuf, M., Burcelin, R., Baldwin, S. A., Liu, M., Lara-Lemus, R., Arvan, P., Schuit, F. C., Wheeler, M. B., Chimienti, F., and Rutter, G. A. (2009) Insulin storage and glucose homeostasis in mice null for the granule zinc transporter ZnT8 and studies of the type 2 diabetes-associated variants. *Diabetes* 58, 2070-2083
8. Foster, M. C., Leapman, R. D., Li, M. X., and Atwater, I. (1993) Elemental composition of secretory granules in pancreatic islets of Langerhans. *Biophys J* 64, 525-532
9. Dunn, M. F. (2005) Zinc-ligand interactions modulate assembly and stability of the insulin hexamer—a review. *Biometals* 18, 295-303
10. Rutter, G. A. (2010) Think zinc: New roles for zinc in the control of insulin secretion. *Islets* 2, 49-50
11. Tamaki, M., Fujitani, Y., Hara, A., Uchida, T., Tamura, Y., Takeno, K., Kawaguchi, M., Watanabe, T., Ogihara, T., Fukunaka, A., Shimizu, T., Mita, T., Kanazawa, A., Imaizumi, M. O., Abe, T., Kiyonari, H., Hojyo, S., Fukada, T., Kawauchi, T., Nagamatsu, S., Hirano, T., Kawamori, R., and Watada, H. (2013) The diabetes-susceptible gene SLC30A8/ZnT8 regulates hepatic insulin clearance. *J Clin Invest* 123, 4513-4524
12. Ashcroft, F. M., and Rorsman, P. (2012) Diabetes mellitus and the beta cell: the last ten years. *Cell* 148, 1160-1171
13. Prasad, R. B., and Groop, L. (2015) Genetics of type 2 diabetes-pitfalls and possibilities. *Genes (Basel)* 6, 87-123
14. Bonnefond, A., and Froguel, P. (2015) Rare and common genetic events in type 2 diabetes: what should biologists know? *Cell Metab* 21, 357-368
15. Flannick, J., Thorleifsson, G., Beer, N. L., Jacobs, S. B., Grarup, N., Burtt, N. P., Mahajan, A., Fuchsberger, C., Atzmon, G., Benediktsson, R., Blangero, J., Bowden, D. W., Brandslund, I., Brosnan, J., Burslem, F., Chambers, J., Cho, Y. S., Christensen, C., Douglas, D. A., Duggirala, R., Dymek, Z., Farjoun, Y., Fennell, T., Fontanillas, P., Forsen, T., Gabriel, S., Glaser, B., Gudbjartsson, D. F., Hanis, C., Hansen, T., Hreidarsson, A. B., Hveem, K., Ingelsson, E., Isomaa, B., Johansson, S., Jorgensen, T., Jorgensen, M. E., Kathiresan, S., Kong, A., Kooner, J., Kravic, J., Laakso, M., Lee, J. Y., Lind, L., Lindgren, C. M., Linneberg, A., Masson, G., Meitinger, T., Mohlke, K. L., Molven, A., Morris, A. P., Potluri, S., Rauramaa, R., Ribel-Madsen, R., Richard, A. M., Rolph, T., Salomaa, V., Segre, A. V., Skarstrand, H., Steinthorsdottir, V., Stringham, H. M., Sulem, P., Tai, E. S., Teo, Y. Y., Teslovich, T., Thorsteinsdottir, U., Trimmer, J. K., Tuomi, T., Tuomilehto, J., Vaziri-Sani, F., Voight, B. F., Wilson, J. G., Boehnke, M., McCarthy, M. I., Njolstad, P. R., Pedersen, O., Groop, L., Cox, D. R., Stefansson, K., and Altshuler, D. (2014) Loss-of-function mutations in SLC30A8 protect against type 2 diabetes. *Nat Genet* 46, 357-363

16. Pearson, E. (2014) Zinc transport and diabetes risk. *Nat Genet* 46, 323-324

17. Sladek, R., Rocheleau, G., Rung, J., Dina, C., Shen, L., Serre, D., Boutin, P., Vincent, D., Belisle, A., Hadjadj, S., Balkau, B., Heude, B., Charpentier, G., Hudson, T. J., Montpetit, A., Pshezhetsky, A. V., Prentki, M., Posner, B. I., Balding, D. J., Meyre, D., Polychronakos, C., and Froguel, P. (2007) A genome-wide association study identifies novel risk loci for type 2 diabetes. *Nature*. 445, 881-885.

18. Scott, L. J., Mohlke, K. L., Bonnycastle, L. L., Willer, C. J., Li, Y., Duren, W. L., Erdos, M. R., Stringham, H. M., Chines, P. S., Jackson, A. U., Prokunina-Olsson, L., Ding, C. J., Swift, A. J., and et al. (2007) A genome-wide association study of type 2 diabetes in Finns detects multiple susceptibility variants. *Science*. 316, 1341-1345.

19. Zeggini, E., Weedon, M. N., Lindgren, C. M., Frayling, T. M., Elliott, K. S., Lango, H., Timpson, N. J., Perry, J. R., Rayner, N. W., Freathy, R. M., Barrett, J. C., and et al. (2007) Replication of genome-wide association signals in UK samples reveals risk loci for type 2 diabetes. *Science*. 316, 1336-1341.

20. Merriman, C., Huang, Q., Rutter, G. A., and Fu, D. (2016) Lipid-tuned Zinc Transport Activity of Human ZnT8 Protein Correlates with Risk for Type-2 Diabetes. *J Biol Chem* 291, 26950-26957

21. Wong, W. P., Allen, N. B., Meyers, M. S., Link, E. O., Zhang, X., MacRenaris, K. W., and El Muayed, M. (2017) Exploring the Association Between Demographics, SLC30A8 Genotype, and Human Islet Content of Zinc, Cadmium, Copper, Iron, Manganese and Nickel. *Sci Rep* 7, 473

22. Li, L., Bai, S., and Sheline, C. T. (2017) hZnT8 (Slc30a8) Transgenic Mice That Overexpress the R325W Polymorph Have Reduced Islet Zn2+ and Proinsulin Levels, Increased Glucose Tolerance After a High-Fat Diet, and Altered Levels of Pancreatic Zinc Binding Proteins. *Diabetes* 66, 551-559

23. Pound, L. D., Sarkar, S. A., Benninger, R. K., Wang, Y., Suwanichkul, A., Shadoan, M. K., Printz, R. L., Oeser, J. K., Lee, C. E., Piston, D. W., McGuinness, O. P., Hutton, J. C., Powell, D. R., and O'Brien, R. M. (2009) Deletion of the mouse Slc30a8 gene encoding zinc transporter-8 results in impaired insulin secretion. *Biochem J* 421, 371-376

24. Pound, L. D., Sarkar, S. A., Ustione, A., Dadi, P. K., Shadoan, M. K., Lee, C. E., Walters, J. A., Shiota, M., McGuinness, O. P., Jacobson, D. A., Piston, D. W., Hutton, J. C., Powell, D. R., and O'Brien, R. M. (2012) The physiological effects of deleting the mouse SLC30A8 gene encoding zinc transporter-8 are influenced by gender and genetic background. *PLoS One* 7, e40972

25. Friend, S. H., and Schadt, E. E. (2014) Translational genomics. Clues from the resilient. *Science* 344, 970-972

26. Ohana, E., Hoch, E., Keasar, C., Kambe, T., Yifrach, O., Hershfinkel, M., and Sekler, I. (2009) Identification of the Zn2+ binding site and mode of operation of a mammalian Zn2+ transporter. *J Biol Chem* 284, 17677-17686

27. Hoch, E., Lin, W., Chai, J., Hershfinkel, M., Fu, D., and Sekler, I. (2012) Histidine pairing at the metal transport site of mammalian ZnT transporters controls Zn2+ over Cd2+ selectivity. *Proc Natl Acad Sci U S A* 109, 7202-7207

28. Lu, M., and Fu, D. (2007) Structure of the zinc transporter YiiP. *Science*. 317, 1746-1748.

29. Lu, M., Chai, J., and Fu, D. (2009) Structural basis for autoregulation of the zinc transporter YiiP. *Nat Struct Mol Biol* 16, 1063-1067

30. Degorce, F., Card, A., Soh, S., Trinquet, E., Knapik, G. P., and Xie, B. (2009) HTRF: A technology tailored for drug discovery—a review of theoretical aspects and recent applications. *Curr Chem Genomics* 3, 22-32

31. Merriman, C. (2018) A subclass of serum anti-ZnT8 antibodies directed to the surface of live pancreatic beta-cells. 293, 579-587

32. Ravassard, P., Hazhouz, Y., Pechberty, S., Bricout-Neveu, E., Armanet, M., Czernichow, P., and Scharfmann, R. (2011) A genetically engineered human pancreatic beta cell line exhibiting glucose-inducible insulin secretion. *J Clin Invest* 121, 3589-3597

33. Parsons, D. S., Hogstrand, C., and Maret, W. (2018) The C-terminal cytosolic domain of the human zinc transporter ZnT8 and its diabetes risk variant. *FEBS J* 285, 1237-1250

34. Cherezov, V., Hofer, N., Szebenyi, D. M., Kolaj, O., Wall, J. G., Gillilan, R., Srinivasan, V., Jaroniec, C. P., and Caffrey, M. (2008) Insights into the mode of action of a putative zinc transporter CzrB in *Thermus thermophilus*. *Structure*. 16, 1378-1388.

35. Boesgaard, T. W., Zilinskaite, J., Vanttinen, M., Laakso, M., Jansson, P. A., Hammarstedt, A., Smith, U., Stefan, N., Fritsche, A., Haring, H., Hribal, M., Sesti, G., Zobel, D. P., Pedersen, O., Hansen, T., and Consortium, E. (2008) The common SLC30A8 Arg325Trp variant is associated with reduced first-phase insulin release in 846 non-diabetic offspring of type 2 diabetes patients—the EUGENE2 study. *Diabetologia* 51, 816-820

36. Merriman, C., Huang, Q., Gu, W., Yu, L., and Fu, D. (2018) A subclass of serum anti-ZnT8 antibodies directed to the surface of live pancreatic beta-cells. *J Biol Chem* 293, 579-587

37. Lim, H. H., Fang, Y., and Williams, C. (2011) High-efficiency screening of monoclonal antibodies for membrane protein crystallography. *PLoS One* 6, e24653

38. Rohou, A., and Grigorieff, N. (2015) CTFFIND4: Fast and accurate defocus estimation from electron micrographs. *J Struct Biol* 192, 216-221

39. Scheres, S. H. (2012) RELION: implementation of a Bayesian approach to cryo-EM structure determination. *J Struct Biol* 180, 519-530

40. Punjani, A., Rubinstein, J. L., Fleet, D. J., and Brubaker, M. A. (2017) cryoSPARC: algorithms for rapid unsupervised cryo-EM structure determination. *Nat Methods* 14, 290-296

41. Vyas, N. K., Vyas, M. N., Chervenak, M. C., Johnson, M. A., Pinto, B. M., Bundle, D. R., and Quiocho, F. A. (2002) Molecular recognition of oligosaccharide epitopes by a monoclonal Fab specific for *Shigella flexneri* Y lipopolysaccharide: X-ray structures and thermodynamics. *Biochemistry* 41, 13575-13586
42. Pettersen, F. F., Goddard, T. D., Huang, C. C., Couch, G. S., Greenblatt, D. M., Meng, F. C., and Ferrin, T. F. (2004) UCSF Chimera—a visualization system for exploratory research and analysis. *J Comput Chem* 25, 1605-1612
43. Huang, Q., Merriman, C., Zhang, H., and Fu, D. (2017) Coupling of Insulin Secretion and Display of a Granule-resident Zinc Transporter ZnT8 on the Surface of Pancreatic Beta Cells. *J Biol Chem* 292, 4034-4043
44. Zhang, J. H., Chung, T. D., and Oldenburg, K. R. (1999) A Simple Statistical Parameter for Use in Evaluation and Validation of High Throughput Screening Assays. *J Biomol Screen* 4, 67-73

TABLE 3

Description of Sequence Listing

| SEQ ID NO. | DESCRIPTION |
|---|---|
| 1 | mAB12 heavy chain (NT) |
| 2 | mAB12 heavy chain (AA) |
| 3 | mAb12 heavy chain CDR1 (AA) |
| 4 | mAb12 heavy chain CDR2 (AA) |
| 5 | mAb12 heavy chain CDR3 (AA) |
| 6 | mAb12 light chain (NT) |
| 7 | mAb12 light chain (AA) |
| 8 | mAb12 light chain CDR1 (AA) |
| 9 | mAb12 light chain CDR2 (AA) |
| 10 | mAb12 light chain CDR3 (AA) |
| 11 | mAb16 heavy chain (NT) |
| 12 | mAb16 heavy chain (AA) |
| 13 | mAb16 heavy chain CDR1 (AA) |
| 14 | mAb16 heavy chain CDR2 (AA) |
| 15 | mAb16 heavy chain CDR3 (AA) |
| 16 | mAb16 light chain (NT) |
| 17 | mAb16 light chain (AA) |
| 18 | mAb16 light chain CDR1 (AA) |
| 19 | mAb16 light chain CDR2 (AA) |
| 20 | mAb16 light chain CDR3 (AA) |
| 21 | mAb17 heavy chain (NT) |
| 22 | mAb17 heavy chain (AA) |

TABLE 3-continued

Description of Sequence Listing

| SEQ ID NO. | DESCRIPTION |
|---|---|
| 23 | mAb17 heavy chain CDR1 (AA) |
| 24 | mAb17 heavy chain CDR2 (AA) |
| 25 | mAb17 heavy chain CDR3 (AA) |
| 26 | mAb17 light chain (NT) |
| 27 | mAb17 light chain (AA) |
| 28 | mAb17 light chain CDR1 (AA) |
| 29 | mAb17 light chain CDR2 (AA) |
| 30 | mAb17 light chain CDR3 (AA) |
| 31 | mAb20 heavy chain (NT) |
| 32 | mAb20 heavy chain (AA) |
| 33 | mAb20 heavy chain CDR1 (AA) |
| 34 | mAb20 heavy chain CDR2 (AA) |
| 35 | mAb20 heavy chain CDR3 (AA) |
| 36 | mAb20 light chain (NT) |
| 37 | mAb20 light chain (AA) |
| 38 | mAb20 light chain CDR1 (AA) |
| 39 | mAb20 light chain CDR2 (AA) |
| 40 | mAb20 light chain CDR3 (AA) |
| 41 | mAb28 heavy chain (NT) |
| 42 | mAb28 heavy chain (AA) |
| 43 | mAb28 heavy chain CDR1 (AA) |
| 44 | mAb28 heavy chain CDR2 (AA) |
| 45 | mAb28 heavy chain CDR3 (AA) |
| 46 | mAb28 light chain (NT) |
| 47 | mAb28 light chain (AA) |
| 48 | mAb28 light chain CDR1 (AA) |
| 49 | mAb28 light chain CDR2 (AA) |
| 50 | mAb28 light chain CDR3 (AA) |
| 51 | mAb39 heavy chain (NT) |
| 52 | mAb39 heavy chain (AA) |
| 53 | mAb39 heavy chain CDR1 (AA) |
| 54 | mAb39 heavy chain CDR2 (AA) |
| 55 | mAb39 heavy chain CDR3 (AA) |
| 56 | mAb39 light chain (NT) |
| 57 | mAb39 light chain (AA) |
| 58 | mAb39 light chain CDR1 (AA) |
| 59 | mAb39 light chain CDR2 (AA) |
| 60 | mAb39 light chain CDR3 (AA) |
| 61 | mAb39 heavy chain v2 (t1375a —> S459T) |
| 62 | mAb39 heavy chain (S459T) |

What is claimed is:

1. An isolated antibody or antigen-binding fragment thereof that specifically binds ZnT8, wherein the antibody or antigen-binding fragment thereof comprises:
   (a) a VH comprising CDRs 1, 2, and 3 with the amino acid sequences set forth in SEQ ID NOS:3-5, respectively and a VL comprising CDRs 1, 2, and 3 with the amino acid sequences set forth in SEQ ID NOS:8-10, respectively; or
   (b) a VH comprising CDRs 1, 2, and 3 with the amino acid sequences set forth in SEQ ID NOS:13-15, respectively and a VL comprising CDRs 1, 2, and 3 with the amino acid sequences set forth in SEQ ID NOS:18-20, respectively; or
   (c) a VH comprising CDRs 1, 2, and 3 with the amino acid sequences set forth in SEQ ID NOS:23-25, respectively and a VL comprising CDRs 1, 2, and 3 with the amino acid sequences set forth in SEQ ID NOS:28-30, respectively; or
   (d) a VH comprising CDRs 1, 2, and 3 with the amino acid sequences set forth in SEQ ID NOS:33-35, respectively and a VL comprising CDRs 1, 2, and 3 with the amino acid sequences set forth in SEQ ID NOS:38-40, respectively; or
   (e) a VH comprising CDRs 1, 2, and 3 with the amino acid sequences set forth in SEQ ID NOS:43-45, respectively and a VL comprising CDRs 1, 2, and 3 with the amino acid sequences set forth in SEQ ID NOS:48-50, respectively; or
   (f) a VH comprising CDRs 1, 2, and 3 with the amino acid sequences set forth in SEQ ID NOS:53-55, respectively and a VL comprising CDRs 1, 2, and 3 with the amino acid sequences set forth in SEQ ID NOS:58-60, respectively.

2. An isolated antibody or antigen-binding fragment of claim 1, wherein the antibody or antigen-binding fragment thereof is an antagonist of ZnT8 activity.

3. An isolated nucleic acid molecule encoding the anti-ZnT8 antibody or antigen-binding fragment thereof of claim 1.

4. A vector comprising a nucleic acid molecule of claim 3.

5. A host cell comprising a vector of claim 4.

6. The host cell of claim 5, wherein the host cell is a prokaryotic cell.

7. The host cell of claim 5, wherein the host cell is a eukaryotic cell.

8. A method for producing an anti-ZnT8 antibody or antigen-binding fragment thereof comprising the steps of (a) culturing a host cell of claim 5 under conditions suitable for expression of the ZnT8 antibody or antigen-binding fragment thereof by the host cells; and (b) recovering the ZnT8 antibody or antigen-binding fragment thereof.

9. The method of claim 8, wherein the host cell is a prokaryotic cell.

10. The method of claim 8, wherein the host cell is a eukaryotic cell.

11. A composition comprising the anti-ZnT8 antibody or antigen-binding fragment thereof of claim 1 and a suitable pharmaceutical carrier.

12. The composition of claim 11, wherein the composition is formulated for intravenous, intramuscular, oral, subcutaneous, intraperitoneal, intrathecal or intramuscular administration.

13. A method of treating diabetes in a mammal comprising the step of administering to the mammal a therapeutically effective amount of the antibody or antigen-binding fragment thereof that specifically binds to ZnT8 of claim 1.

14. The antibody or antigen-binding fragment of claim 1, wherein the antigen-binding fragment is selected from the group consisting of an scFv, sc(Fv)2, Fab, F(ab)2, and a diabody.

15. An isolated antibody or antigen-binding fragment thereof that specifically binds ZnT8, wherein the antibody or antigen-binding fragment thereof comprises:

(a) a VH comprising the amino acid sequence as set forth in SEQ ID NO:2 and a VL comprising the amino acid sequence as set forth in SEQ ID NO:7;

(b) a VH comprising the amino acid sequence as set forth in SEQ ID NO:12 and a VL comprising the amino acid sequence as set forth in SEQ ID NO:17;

(c) a VH comprising the amino acid sequence as set forth in SEQ ID NO:22 and a VL comprising the amino acid sequence as set forth in SEQ ID NO:27;

(d) a VH comprising the amino acid sequence as set forth in SEQ ID NO:32 and a VL comprising the amino acid sequence as set forth in SEQ ID NO:37;

(e) a VH comprising the amino acid sequence as set forth in SEQ ID NO:42 and a VL comprising the amino acid sequence as set forth in SEQ ID NO:47; or (d) a VH comprising the amino acid sequence as set forth in SEQ ID NO:52 and a VL comprising the amino acid sequence as set forth in SEQ ID NO:57.

* * * * *

SEQUENCE LISTING

```
<160> NUMBER OF SEQ ID NOS: 62

<210> SEQ ID NO 1
<211> LENGTH: 1404
<212> TYPE: DNA
<213> ORGANISM: Artificial Sequence
<220> FEATURE:
<223> OTHER INFORMATION: mAB12 heavy chain

<400> SEQUENCE: 1
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatacc ttcacaaact atccaatgca ctgggtgaag     180
cagactccag gaaagggttt aaagtggatg gctggataa acacctactc tggagtgcca     240
acatatgcag atgacttcaa gggacggttt gccttctctt tggaaacctc tgccagtact     300
gcatatttgc agatcaacaa cctcaaaaat gaagacatgg ctacatattt ctgtgcaaga     360
tcgaacccct atgattactt gtatgctatg gactcctggg gtcaaggaac ctcagtcacc     420
gtctctagtg ccaaaacgac accccatct gtctaccac tggcccctgg atctgctgcc     480
```

```
caaactaact ccatggtgac cctgggatgc ctggtcaagg gctatttccc tgagccagtg     540
acagtgacct ggaactctgg atccctgtcc agcggtgtgc acaccttccc agctgtcctg     600
cagtctgacc tctacactct gagcagctca gtgactgtcc cctccagcac ctggcccagc     660
gagaccgtca cctgcaacgt tgcccacccg gccagcagca ccaaggtgga caagaaaatt     720
gtgcccaggg attgtggttg taagccttgc atatgtacag tcccagaagt atcatctgtc     780
ttcatcttcc ccccaaagcc caaggatgtg ctcaccatta ctctgactcc taaggtcacg     840
tgtgttgtgg tagacatcag caaggatgat cccgaggtcc agttcagctg gtttgtagat     900
gatgtggagg tgcacacagc tcagacgcaa ccccgggagg agcagttcaa cagcactttc     960
cgctcagtca gtgaacttcc catcatgcac caggactggc tcaatggcaa ggagttcaaa    1020
tgcagggtca acagtgcagc tttccctgcc cccatcgaga aaaccatctc aaaaccaaa     1080 ggcagaccga aggctccaca ggtgtacacc attccacctc ccaaggagca gatggccaag    1140
gataaagtca gtctgacctg catgataaca gacttcttcc ctgaagacat tactgtggag    1200
tggcagtgga atgggcagcc agcggagaac tacaagaaca ctcagcccat catggacaca    1260
gatggctctt acttcgtcta cagcaagctc aatgtgcaga gagcaactg ggaggcagga     1320 aatactttca cctgctctgt gttacatgag ggcctgcaca accaccatac tgagaagagc    1380
ctctcccact ctcctggtaa atga                                            1404
```

<210> SEQ ID NO 2
<211> LENGTH: 467
<212> TYPE: PRT
<213> ORGANISM: Artificial Sequence
<220> FEATURE:
<223> OTHER INFORMATION: mAB12 heavy chain

<400> SEQUENCE: 2

```
Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Val Lys Gln Thr Pro Gly
    50                  55                  60

Lys Gly Leu Lys Trp Met Gly Trp Ile Asn Thr Tyr Ser Gly Val Pro
65                  70                  75                  80

Thr Tyr Gly Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Met Ala Thr Tyr Phe Cys Ala Arg Ser Asn Pro Tyr Asp Tyr Leu Tyr
        115                 120                 125

Ala Met Asp Ser Trp Gly Gln Gly Thr Ser Val Thr Val Ser Ser Ala
    130                 135                 140

Lys Thr Thr Pro Pro Ser Val Tyr Pro Leu Ala Pro Gly Ser Ala Ala
145                 150                 155                 160

Gln Thr Asn Ser Met Val Thr Leu Gly Cys Leu Val Lys Gly Tyr Phe
                165                 170                 175

Pro Glu Pro Val Thr Val Thr Trp Asn Ser Gly Ser Leu Ser Ser Gly
            180                 185                 190

Val His Thr Phe Pro Ala Val Leu Gln Ser Asp Leu Tyr Thr Leu Ser
```

```
                195                 200                 205
    Ser Ser Val Thr Val Pro Ser Thr Trp Pro Ser Glu Thr Val Thr
    210                 215                 220

Cys Asn Val Ala His Pro Ala Ser Ser Thr Lys Val Asp Lys Lys Ile
225                 230                 235                 240

Val Pro Arg Asp Cys Gly Cys Lys Pro Cys Ile Cys Thr Val Pro Glu
                245                 250                 255

Val Ser Ser Val Phe Ile Phe Pro Pro Lys Pro Lys Asp Val Leu Thr
                260                 265                 270

Ile Thr Leu Thr Pro Lys Val Thr Cys Val Val Val Asp Ile Ser Lys
                275                 280                 285

Asp Asp Pro Glu Val Gln Phe Ser Trp Phe Val Asp Asp Val Glu Val
    290                 295                 300

His Thr Ala Gln Thr Gln Pro Arg Glu Glu Gln Phe Asn Ser Thr Phe
305                 310                 315                 320

Arg Ser Val Ser Glu Leu Pro Ile Met His Gln Asp Trp Leu Asn Gly
                325                 330                 335

Lys Glu Phe Lys Cys Arg Val Asn Ser Ala Ala Phe Pro Ala Pro Ile
                340                 345                 350

Glu Lys Thr Ile Ser Lys Thr Lys Gly Arg Pro Lys Ala Pro Gln Val
                355                 360                 365

Tyr Thr Ile Pro Pro Pro Lys Glu Gln Met Ala Lys Asp Lys Val Ser
                370                 375                 380

Leu Thr Cys Met Ile Thr Asp Phe Phe Pro Glu Asp Ile Thr Val Glu
385                 390                 395                 400

Trp Gln Trp Asn Gly Gln Pro Ala Glu Asn Tyr Lys Asn Thr Gln Pro
                405                 410                 415

Ile Met Asp Thr Asp Gly Ser Tyr Phe Val Tyr Ser Lys Leu Asn Val
                420                 425                 430

Gln Lys Ser Asn Trp Glu Ala Gly Asn Thr Phe Thr Cys Ser Val Leu
                435                 440                 445

His Glu Gly Leu His Asn His His Thr Glu Lys Ser Leu Ser His Ser
    450                 455                 460

Pro Gly Lys
    465

<210> SEQ ID NO 3
<211> LENGTH: 7
<212> TYPE: PRT
<213> ORGANISM: Artificial Sequence
<220> FEATURE:
<223> OTHER INFORMATION: mAb12 heavy chain CDR1

<400> SEQUENCE: 3

Gly Tyr Thr Phe Thr Asn Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: mAb12 heavy chain CDR2

<400> SEQUENCE: 4

Thr Tyr Ser Gly Val
1               5
```

<210> SEQ ID NO 5
<211> LENGTH: 12
<212> TYPE: PRT
<213> ORGANISM: Artificial Sequence
<220> FEATURE:
<223> OTHER INFORMATION: mAB heavy chain CDR3

<400> SEQUENCE: 5

Ser Asn Pro Tyr Asp Tyr Leu Tyr Ala Met Asp Ser
1               5                   10

<210> SEQ ID NO 6
<211> LENGTH: 726
<212> TYPE: DNA
<213> ORGANISM: Artificial Sequence
<220> FEATURE:
<223> OTHER INFORMATION: mAb12 light chain

<400> SEQUENCE: 6

```
atggacatga gggtgcccgc tcagctcctg gggctcctgc tgctgtggct gagaggtgcg      60
cgctgtgatg ttgtgatgac ccaaactcca ctctccctgc ctgtcagtct tggagatcaa    120
gcctccatct cctgcagatc tagtcagagc cttgtacaca tcaatggaaa cacctatata    180
cattggtacc tgcagaagcc aggccagtct ccaaagctcc tgatctacaa agtttccaac    240
cgattttctg gggtcccaga caggttcagt ggcagtggat cagggacaga ttttacactc    300
aagatcagaa gagtggaggc tgaggatctg ggagtttatt tctgctctca aaatacacat    360
gttccattca cattcggctc ggggacaaag ttggaaataa aacgtgcaga tgctgcgcca    420
actgtatcca tcttcccacc atctagcgag cagttaacat ctggaggtgc ctcagtcgtg    480
tgcttcttga caacttcta ccccaaagac atcaatgtca gtggaagat tgatggcagt    540
gaacgacaaa atggcgtcct gaacagttgg actgatcagg acagcaaaga cagcacctac    600
agcatgagca gcaccctcac gttgaccaag gacgagtatg aacgacataa cagctatacc    660
tgtgaggcca ctcacaagac atcaacttca cccattgtca agagcttcaa caggaatgag    720
tgttag                                                                726
```

<210> SEQ ID NO 7
<211> LENGTH: 241
<212> TYPE: PRT
<213> ORGANISM: Artificial Sequence
<220> FEATURE:
<223> OTHER INFORMATION: mAb12 light chain

<400> SEQUENCE: 7

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
                20                  25                  30

Leu Pro Val Ser Leu Gly Asp Gln Ala Ser Ile Ser Cys Arg Ser Ser
            35                  40                  45

Gln Ser Leu Val His Ile Asn Gly Asn Thr Tyr Ile His Trp Tyr Leu
        50                  55                  60

Gln Lys Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Arg Arg Val Glu Ala Glu Asp Leu Gly Val
                100                 105                 110

```
Tyr Phe Cys Ser Gln Asn Thr His Val Pro Phe Thr Phe Gly Ser Gly
            115                 120                 125

Thr Lys Leu Glu Ile Lys Arg Ala Asp Ala Ala Pro Thr Val Ser Ile
        130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys

<210> SEQ ID NO 8
<211> LENGTH: 16
<212> TYPE: PRT
<213> ORGANISM: Artificial Sequence
<220> FEATURE:
<223> OTHER INFORMATION: mAb12 light chain CDR1

<400> SEQUENCE: 8

Arg Ser Ser Gln Ser Leu Val His Ile Asn Gly Asn Thr Tyr Ile His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: mAb12 light chain CDR2

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: mAb12 light chain CDR3

<400> SEQUENCE: 10

Ser Gln Asn Thr His Val Pro Phe Thr
1               5

<210> SEQ ID NO 11
<211> LENGTH: 1401
<212> TYPE: DNA
<213> ORGANISM: Artificial Sequence
<220> FEATURE:
<223> OTHER INFORMATION: mAb16 heavy chain

<400> SEQUENCE: 11
atggacatga gggtgcccgc tcagctcctg gggctcctgc tgctgtggct gagaggtgcg      60
cgctgtcaga tccagttggt gcagtctgga cctgagctga agaagcctgg agagacagtc    120
```

```
acgatctcct gcaaggcttc tggatatacc ttcacacact atccagtgca ctgggtgaag      180
caggctccag gaaagggttt acagtggatg ggctggataa acacctactc tggagtgcca      240
acatatgcag atgccttcaa gaaacgtttt gccttctctt tggaaacctc tgccagcact      300
gcatatttgc agatcaacaa cctcaaaagt gaggacatgg ctacatattt ctgtgcaaga      360
tcgagggtct atgatgggta ctattttgac tactggggcc aaggcaccac tctcaccgtc      420
tctagtgcca aaacgacacc cccatctgtc tacccactgg cccctggatc tgctgcccaa      480
actaactcca tggtgaccct gggatgcctg gtcaagggct atttccctga gccagtgaca      540
gtgacctgga actctggatc cctgtccagc ggtgtgcaca ccttcccagc tgtcctgcag      600
tctgacctct acactctgag cagctcagtg actgtcccct ccagcacctg cccagcgag       660 accgtcacct gcaacgttgc ccacccggcc agcagcacca aggtggacaa gaaaattgtg      720
cccagggatt gtggttgtaa gccttgcata tgtacagtcc cagaagtatc atctgtcttc      780 atcttcccc caaagcccaa ggatgtgctc accattactc tgactcctaa ggtcacgtgt      840
gttgtggtag acatcagcaa ggatgatccc gaggtccagt tcagctggtt tgtagatgat      900
gtggaggtgc acacagctca gacgcaaccc cgggaggagc agttcaacag cactttccgc      960
tcagtcagtg aacttcccat catgcaccag gactggctca atggcaagga gttcaaatgc     1020
agggtcaaca gtgcagcttt ccctgccccc atcgagaaaa ccatctccaa aaccaaaggc     1080
agaccgaagg ctccacaggt gtacaccatt ccacctccca aggagcagat ggccaaggat     1140
aaagtcagtc tgacctgcat gataacagac ttcttccctg aagacattac tgtggagtgg     1200
cagtggaatg ggcagccagc ggagaactac aagaacactc agcccatcat ggacacagat     1260
ggctcttact cgtctacag caagctcaat gtgcagaaga gcaactggga ggcaggaaat      1320
actttcacct gctctgtgtt acatgagggc ctgcacaacc accatactga aagagcctc      1380 tcccactctc ctggtaaatg a                                               1401
```

<210> SEQ ID NO 12
<211> LENGTH: 466
<212> TYPE: PRT
<213> ORGANISM: Artificial Sequence
<220> FEATURE:
<223> OTHER INFORMATION: mAb16 heavy chain

<400> SEQUENCE: 12

```
Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Thr Ile Ser Cys Lys Ala Ser Gly
        35                  40                  45

Tyr Thr Phe Thr His Tyr Pro Val His Trp Val Lys Gln Ala Pro Gly
    50                  55                  60

Lys Gly Leu Gln Trp Met Gly Trp Ile Asn Thr Tyr Ser Gly Val Pro
65                  70                  75                  80

Thr Tyr Ala Asp Ala Phe Lys Lys Arg Phe Ala Phe Ser Leu Glu Thr
                85                  90                  95

Ser Ala Ser Thr Ala Tyr Leu Gln Ile Asn Asn Leu Lys Ser Glu Asp
            100                 105                 110

Met Ala Thr Tyr Phe Cys Ala Arg Ser Arg Val Tyr Asp Gly Tyr Tyr
        115                 120                 125
```

```
Phe Asp Tyr Trp Gly Gln Gly Thr Thr Leu Thr Val Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Asp Ile Ser Lys Asp
        275                 280                 285

Asp Pro Glu Val Gln Phe Ser Trp Phe Val Asp Val Glu Val His
290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 13
<211> LENGTH: 7
<212> TYPE: PRT
<213> ORGANISM: Artificial Sequence
<220> FEATURE:
<223> OTHER INFORMATION: mAb16 heavy chain CDR1

<400> SEQUENCE: 13

Gly Tyr Thr Phe Thr His Tyr
1               5
```

<210> SEQ ID NO 14
<211> LENGTH: 6
<212> TYPE: PRT
<213> ORGANISM: Artificial Sequence
<220> FEATURE:
<223> OTHER INFORMATION: mAb16 heavy chain CDR2

<400> SEQUENCE: 14

Asn Thr Tyr Ser Gly Val
1               5

<210> SEQ ID NO 15
<211> LENGTH: 11
<212> TYPE: PRT
<213> ORGANISM: Artificial Sequence
<220> FEATURE:
<223> OTHER INFORMATION: mAb16 heavy chain CDR3

<400> SEQUENCE: 15

Ser Arg Val Tyr Asp Gly Tyr Tyr Phe Asp Tyr
1               5                   10

<210> SEQ ID NO 16
<211> LENGTH: 726
<212> TYPE: DNA
<213> ORGANISM: Artificial Sequence
<220> FEATURE:
<223> OTHER INFORMATION: mAb16 light chain

<400> SEQUENCE: 16

| | | | | | |
|---|---|---|---|---|---|
| atggacatga | gggtgcccgc | tcagctcctg | gggctcctgc | tgctgtggct | gagaggtgcg       60 |
| cgctgtgatg | ttgtgatgac | ccaaactcca | ctctccctgc | ctgtcagtct | tggagatcaa      120 |
| gcctccatct | cttgcagatc | tagtcagagc | cttgtacaca | gtaatggaaa | gacctattta      180 |
| cattggtacc | tgcagaagcc | aggccagtct | ccaaacctcc | tgatctacaa | agtttccaac      240 |
| cgattttctg | gggtcccaga | caggttcagt | ggcagtggat | cagggacaga | tttcacactc      300 |
| aagatcagca | gagtggaggc | tgaggatctg | ggagtttatt | tctgctctca | acttacacat      360 |
| gttccgtgga | cgttcggtgg | aggcaccaag | ctggaaatca | aacgtgcaga | tgctgcgcca      420 |
| actgtatcca | tcttcccacc | atctagcgag | cagttaacat | ctggaggtgc | ctcagtcgtg      480 |
| tgcttcttga | acaacttcta | ccccaaagac | atcaatgtca | agtggaagat | tgatggcagt      540 |
| gaacgacaaa | atggcgtcct | gaacagttgg | actgatcagg | acagcaaaga | cagcacctac      600 |
| agcatgagca | gcaccctcac | gttgaccaag | gacgagtatg | aacgacataa | cagctatacc      660 |
| tgtgaggcca | ctcacaagac | atcaacttca | cccattgtca | agagcttcaa | caggaatgag      720 |
| tgttag | | | | |          726 |

<210> SEQ ID NO 17
<211> LENGTH: 241
<212> TYPE: PRT
<213> ORGANISM: Artificial Sequence
<220> FEATURE:
<223> OTHER INFORMATION: mAb16 light chain

<400> SEQUENCE: 17

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
            20                  25                  30

Leu Pro Val Ser Leu Gly Asp Gln Ala Ser Ile Ser Cys Arg Ser Ser

```
                35                  40                  45
Gln Ser Leu Val His Ser Asn Gly Lys Thr Tyr Leu His Trp Tyr Leu
 50                  55                  60

Gln Lys Pro Gly Gln Ser Pro Asn Leu Leu Ile Tyr Lys Val Ser Asn
 65                  70                  75                  80

Arg Phe Ser Gly Val Pro Asp Arg Phe Ser Gly Ser Gly Ser Gly Thr
                 85                  90                  95

Asp Phe Thr Leu Lys Ile Ser Arg Val Glu Ala Glu Asp Leu Gly Val
                100                 105                 110

Tyr Phe Cys Ser Gln Leu Thr His Val Pro Trp Thr Phe Gly Gly Gly
            115                 120                 125

Thr Lys Leu Glu Ile Lys Arg Ala Asp Ala Ala Pro Thr Val Ser Ile
130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
                180                 185                 190

Gln Asp Ser Lys Asp Ser Thr Tyr Ser Met Ser Ser Thr Leu Thr Leu
            195                 200                 205

Thr Lys Asp Glu Tyr Glu Arg His Asn Ser Tyr Thr Cys Glu Ala Thr
210                 215                 220

His Lys Thr Ser Thr Ser Pro Ile Val Lys Ser Phe Asn Arg Asn Glu
225                 230                 235                 240

Cys

<210> SEQ ID NO 18
<211> LENGTH: 16
<212> TYPE: PRT
<213> ORGANISM: Artificial Sequence
<220> FEATURE:
<223> OTHER INFORMATION: mAb16 light chain CDR1

<400> SEQUENCE: 18

Arg Ser Ser Gln Ser Leu Val His Ser Asn Gly Lys Thr Tyr Leu His
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: mAb16 light chain CDR2

<400> SEQUENCE: 19

Lys Val Ser Asn Arg Phe Ser
1               5

<210> SEQ ID NO 20
<211> LENGTH: 8
<212> TYPE: PRT
<213> ORGANISM: Artificial Sequence
<220> FEATURE:
<223> OTHER INFORMATION: mAb16 light chain CDR3

<400> SEQUENCE: 20

Ser Gln Leu Thr His Val Pro Trp
1               5
```

<210> SEQ ID NO 21
<211> LENGTH: 1407
<212> TYPE: DNA
<213> ORGANISM: Artificial Sequence
<220> FEATURE:
<223> OTHER INFORMATION: mAb17 heavy chain

<400> SEQUENCE: 21

```
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatacc ttcacaaact atccaatgca ctggttgaag     180
caggctccag gaaagggttt aaagtggatg gctggataa cacctactc tggagtgcca      240
acatatgcag atgacttcaa gggacggttt gccttctctt tggaaacctc tgccagcact     300
gcatatttgc agatcaacaa cctcaaaaat gaggacatgg ctacatattt ctgtacaaaa     360
tcgcgcatta ctacgatggg gggttatgct atggactgct ggggtcaagg aacctcagtc     420
accgtctcta gtgccaaaac gacacccccca tctgtctacc cactggcccc tggatctgct     480
gcccaaacta actccatggt gaccctggga tgcctggtca gggctatttt ccctgagcca     540
gtgacagtga cctggaactc tggatccctg tccagcggtg tgcacacctt cccagctgtc     600
ctgcagtctg acctctacac tctgagcagc tcagtgactg tccccctccag cacctggccc     660
agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tccccccaaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caaccccggg aggagcagtt caacagcact     960
ttccgctcag tcagtgaact tcccatcatg caccaggact ggctcaatgg caaggagttc    1020
aaatgcaggg tcaacagtgc agctttccct gccccccatcg agaaaaccat ctccaaaacc    1080
aaaggcagac cgaaggctcc acaggtgtac accattccac ctcccaagga gcagatggcc    1140
aaggataaag tcagtctgac ctgcatgata acagacttct ccctgaaaga cattactgtg    1200
gagtggcagt ggaatgggca gccagcggag aactacaaga cactcagcc catcatggac    1260
acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407
```

<210> SEQ ID NO 22
<211> LENGTH: 468
<212> TYPE: PRT
<213> ORGANISM: Artificial Sequence
<220> FEATURE:
<223> OTHER INFORMATION: mAb17 heavy chain

<400> SEQUENCE: 22

```
Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Leu Lys Gln Ala Pro Gly
    50                  55                  60
```

```
Lys Gly Leu Lys Trp Met Gly Trp Ile Asn Thr Tyr Ser Gly Val Pro
 65                  70                  75                  80

Thr Tyr Ala Asp Asp Phe Lys Gly Arg Phe Ala Phe Ser Leu Glu Thr
             85                  90                  95

Ser Ala Ser Thr Ala Tyr Leu Gln Ile Asn Asn Leu Lys Asn Glu Asp
            100                 105                 110

Met Ala Thr Tyr Phe Cys Thr Lys Ser Arg Ile Thr Thr Met Gly Gly
            115                 120                 125

Tyr Ala Met Asp Cys Trp Gly Gln Gly Thr Ser Val Thr Val Ser Ser
130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
            195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
            245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
            275                 280                 285

Lys Asp Asp Pro Glu Val Gln Phe Ser Trp Phe Val Asp Asp Val Glu
290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
            325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
            355                 360                 365

Val Tyr Thr Ile Pro Pro Pro Lys Glu Gln Met Ala Lys Asp Lys Val
            370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
            405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
            435                 440                 445

Leu His Glu Gly Leu His Asn His Thr Glu Lys Ser Leu Ser His
            450                 455                 460

Ser Pro Gly Lys
465
```

<210> SEQ ID NO 23
<211> LENGTH: 7
<212> TYPE: PRT
<213> ORGANISM: Artificial Sequence
<220> FEATURE:
<223> OTHER INFORMATION: mAb17 heavy chain CDR1

<400> SEQUENCE: 23

Gly Tyr Thr Phe Thr Asn Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: mAb17 heavy chain CDR2

<400> SEQUENCE: 24

Asn Thr Tyr Ser Gly Val
1               5

<210> SEQ ID NO 25
<211> LENGTH: 13
<212> TYPE: PRT
<213> ORGANISM: Artificial Sequence
<220> FEATURE:
<223> OTHER INFORMATION: mAb17 heavy chain CDR3

<400> SEQUENCE: 25

Ser Arg Ile Thr Thr Met Gly Gly Tyr Ala Met Asp Cys
1               5                   10

<210> SEQ ID NO 26
<211> LENGTH: 726
<212> TYPE: DNA
<213> ORGANISM: Artificial Sequence
<220> FEATURE:
<223> OTHER INFORMATION: mAb17 light chain

<400> SEQUENCE: 26
atggacatga gggtgcccgc tcagctcctg gggctcctgc tgctgtggct gagaggtgcg      60
cgctgtgaag ttgtgatgac ccaaactcca ctctccctgc ctgtcagtct tggagatcaa     120
gcctccatct cttgcagatc tagtcagagc cttctacaca gtaatggaaa cacctattta     180
cattggtacc tgcagaggcc aggccagtct ccaaacctcc tgatctccaa agtttccaac     240
cgattttctg ggtcccagac aggttcagtg gcagtggatc agggacagat ttcacactc     300 aagatcagca gagtggaggc tgaggatctg ggagtttatt tctgctctca aaatacacat     360
gttccgtgga cgttcggtgg aggcaccaag ctggaaatca acgtgcaga tgctgcgcca     420 actgtatcca tcttcccacc atctagcgag cagttaacat ctggaggtgc ctcagtcgtg     480
tgcttcttga caacttcta cccaaagac atcaatgtca gtggaagat tgatggcagt     540 gaacgacaaa atggcgtcct gaacagttgg actgatcagg acagcaaaga cagcaccta     600 agcatgagca gcaccctcac gttgaccaag gacgagtatg aacgacataa cagctatacc     660
tgtgaggcca ctcacaagac atcaacttca cccattgtca agagcttcaa caggaatgag     720
tgttag                                                               726

<210> SEQ ID NO 27
<211> LENGTH: 241
<212> TYPE: PRT

<213> ORGANISM: Artificial Sequence
<220> FEATURE:
<223> OTHER INFORMATION: mAb17 light chain

<400> SEQUENCE: 27

```
Met Asp Met Arg Val Pro Ala Gln Leu Leu Gly Leu Leu Leu Leu Trp
1               5                   10                  15

Leu Arg Gly Ala Arg Cys Glu Val Val Met Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Leu His Ser Asn Gly Asn Thr Tyr Leu His Trp Tyr Leu
50                  55                  60

Gln Arg Pro Gly Gln Ser Pro Asn Leu Leu Ile Ser Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
210                 215                 220

His Lys Thr Ser Thr Ser Pro Ile Val Lys Ser Phe Asn Arg Asn Glu
225                 230                 235                 240

Cys
```

<210> SEQ ID NO 28
<211> LENGTH: 16
<212> TYPE: PRT
<213> ORGANISM: Artificial Sequence
<220> FEATURE:
<223> OTHER INFORMATION: mAb17 light chain CDR1

<400> SEQUENCE: 28

```
Arg Ser Ser Gln Ser Leu Leu His Ser Asn Gly Asn Thr Tyr Leu His
1               5                   10                  15
```

<210> SEQ ID NO 29
<211> LENGTH: 7
<212> TYPE: PRT
<213> ORGANISM: Artificial Sequence
<220> FEATURE:
<223> OTHER INFORMATION: mAb17 light chain CDR2

<400> SEQUENCE: 29

```
Lys Val Ser Asn Arg Phe Ser
1               5
```

<210> SEQ ID NO 30
<211> LENGTH: 9
<212> TYPE: PRT
<213> ORGANISM: Artificial Sequence
<220> FEATURE:
<223> OTHER INFORMATION: mAb17 light chain CDR3

<400> SEQUENCE: 30

Ser Gln Asn Thr His Val Pro Trp Thr
1               5

<210> SEQ ID NO 31
<211> LENGTH: 1407
<212> TYPE: DNA
<213> ORGANISM: Artificial Sequence
<220> FEATURE:
<223> OTHER INFORMATION: mAb20 heavy chain

<400> SEQUENCE: 31

```
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatatc ttcacaaaac tatccaatgca ctgggtgaag     180 caggctccag gaaagggttt aaagtggatg gctggataaa cacctactc tggagtgcca     240 acacatgcag atgacttcaa gggacggttt gccttctctt tggaaacctc tgccaacagt     300 gcattttgc agatcaacaa cctcaaaaat gaggacacgg ctacatattt ctgtacaaga     360
tcgcgcatta ctccgacggg gggctatgct atggactact ggggtcaagg aacctcagtc     420
accgtctcta gtgccaaaac gacacccca tctgtctacc cactggcccc tggatctgct     480
gcccaaacta actccatggt gaccctggga tgcctggtca agggctattt ccctgagcca     540
gtgacagtga cctggaactc tggatccctg tccagcggtg tgcacacctt cccagctgtc     600
ctgcagtctg acctctacac tctgagcagc tcagtgactg tccctccag cacctggccc     660 agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tcccccaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caacccgggg aggagcagtt caacagcact     960
ttccgctcag tcagtgaact tcccatcatg caccaggact ggctcaatgg caaggagttc    1020
aaatgcaggg tcaacagtgc agctttccct gcccccatcg agaaaccat ctccaaaacc    1080 aaaggcagac cgaaggctcc acaggtgtac accattccac ctcccaagga gcagatggcc    1140
aaggataaag tcagtctgac ctgcatgata acagacttct ccctgaaga cattactgtg    1200 gagtggcagt ggaatgggca gccagcggag aactacaaga cactcagcc catcatggac    1260 acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407
```

<210> SEQ ID NO 32
<211> LENGTH: 468
<212> TYPE: PRT
<213> ORGANISM: Artificial Sequence
<220> FEATURE:
<223> OTHER INFORMATION: mAb20 heavy chain

<400> SEQUENCE: 32

```
Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Ile Phe Thr Asn Tyr Pro Met His Trp Val Lys Gln Ala Pro Gly
    50                  55                  60

Lys Gly Leu Lys Trp Met Gly Trp Ile Asn Thr Tyr Ser Gly Val Pro
65                  70                  75                  80

Thr His Ala Asp Asp Phe Lys Gly Arg Phe Ala Phe Ser Leu Glu Thr
                85                  90                  95

Ser Ala Asn Ser Ala Phe Leu Gln Ile Asn Asn Leu Lys Asn Glu Asp
            100                 105                 110

Thr Ala Thr Tyr Phe Cys Thr Arg Ser Arg Ile Thr Pro Thr Gly Gly
        115                 120                 125

Tyr Ala Met Asp Tyr Trp Gly Gln Gly Thr Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415
```

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
            435                 440                 445

Leu His Glu Gly Leu His Asn His His Thr Glu Lys Ser Leu Ser His
            450                 455                 460

Ser Pro Gly Lys
465

<210> SEQ ID NO 33
<211> LENGTH: 7
<212> TYPE: PRT
<213> ORGANISM: Artificial Sequence
<220> FEATURE:
<223> OTHER INFORMATION: mAb20 heavy chain CDR1

<400> SEQUENCE: 33

Gly Tyr Ile Phe Thr Asn Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: mAb20 heavy chain CDR2

<400> SEQUENCE: 34

Asn Thr Tyr Ser Gly Val
1               5

<210> SEQ ID NO 35
<211> LENGTH: 13
<212> TYPE: PRT
<213> ORGANISM: Artificial Sequence
<220> FEATURE:
<223> OTHER INFORMATION: mAb20 heavy chain CDR3

<400> SEQUENCE: 35

Ser Arg Ile Thr Pro Thr Gly Gly Tyr Ala Met Asp Tyr
1               5                   10

<210> SEQ ID NO 36
<211> LENGTH: 726
<212> TYPE: DNA
<213> ORGANISM: Artificial Sequence
<220> FEATURE:
<223> OTHER INFORMATION: mAb20 light chain

<400> SEQUENCE: 36
atggacatga gggtgcccgc tcagctcctg gggctcctgc tgctgtggct gagaggtgcg      60
cgctgtgatg ttgtgatgac ccaaactcca ctctccctgc ctgtcagtct tggagatcaa     120
gcctccatct cttgcagatc tagtcagagc cttgtacaca gtaatggaaa cacctattta     180
cattggtacc tgcagaagcc aggccagtct ccaaacctcc tgatctccaa agtttccaac     240
cgattttctg ggtcccccaga aaggttcagt ggcagtggat cagggacaga tttcacactc     300
aagatcagca gagtggaggc tgaggatctg ggagtttatt tctgctctca aaatacacat     360
gttccgtgga cgttcggtgg aggcaccaag ctggaaatca aacgtgcaga tgctgcgcca     420
actgtatcca tcttcccacc atctagcgag cagttaacat ctggaggtgc ctcagtcgtg     480
tgcttcttga acaacttcta ccccaaagac atcaatgtca agtggaagat tgatggcagt     540

```
gaacgacaaa atggcgtcct gaacagttgg actgatcagg acagcaaaga cagcacctac    600
agcatgagca gcaccctcac gttgaccaag gacgagtatg aacgacataa cagctatacc    660
tgtgaggcca ctcacaagac atcaacttca cccattgtca agagcttcaa caggaatgag    720
tgttag                                                               726
```

```
<210> SEQ ID NO 37
<211> LENGTH: 241
<212> TYPE: PRT
<213> ORGANISM: Artificial Sequence
<220> FEATURE:
<223> OTHER INFORMATION: mAb20 light chain

<400> SEQUENCE: 37
```

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Ser Asn Gly Asn Thr Tyr Leu His Trp Tyr Leu
    50                  55                  60

Gln Lys Pro Gly Gln Ser Pro Asn Leu Leu Ile Ser Lys Val Ser Asn
65                  70                  75                  80

Arg Phe Ser Gly Val Pro Glu Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys

```
<210> SEQ ID NO 38
<211> LENGTH: 16
<212> TYPE: PRT
<213> ORGANISM: Artificial Sequence
<220> FEATURE:
<223> OTHER INFORMATION: mAb20 light chain CDR1

<400> SEQUENCE: 38
```

Arg Ser Ser Gln Ser Leu Val His Ser Asn Gly Asn Thr Tyr Leu His
1               5                   10                  15

```
<210> SEQ ID NO 39
<211> LENGTH: 7
<212> TYPE: PRT
<213> ORGANISM: Artificial Sequence
<220> FEATURE:
<223> OTHER INFORMATION: mAb20 light chain CDR2

<400> SEQUENCE: 39

Lys Val Ser Asn Arg Phe Ser
1               5

<210> SEQ ID NO 40
<211> LENGTH: 9
<212> TYPE: PRT
<213> ORGANISM: Artificial Sequence
<220> FEATURE:
<223> OTHER INFORMATION: mAb40 light chain CDR3

<400> SEQUENCE: 40

Ser Gln Asn Thr His Val Pro Trp Thr
1               5

<210> SEQ ID NO 41
<211> LENGTH: 1407
<212> TYPE: DNA
<213> ORGANISM: Artificial Sequence
<220> FEATURE:
<223> OTHER INFORMATION: mAb28 heavy chain

<400> SEQUENCE: 41
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatacc ttcacaaaac tatccaatgca ctgggtaaag    180 caggctccag gaaaggattt aaagtggatg gctggataaa cacctactc tggaatgtca     240 acatatgcag atgacttcaa gggacggttt gccttctctt tggaaacctc tgccagcact    300
gcgtatttgc agatcaacaa cctcaaaaat gaggacatgg ctacatattt ctgtgcaaga    360
tcgcgcatta acgatggg gggctatgct atggactact ggggtcaagg agcctcagtc      420
accgtctcta gtgccaaaac gacaccccca tctgtctacc cactggcccc tggatctgct    480
gcccaaacta actccatggt gaccctggga tgcctggtca aggctatttt ccctgagcca    540
gtgacagtga cctggaactc tggatccctg tccagcggtg tgcacacctt cccagctgtc    600
ctgcagtctg acctctacac tctgagcagc tcagtgactg tccccctccag cacctggccc   660 agcgagaccg tcacctgcaa cgttgcccac ccggccagca gcaccaaggt ggacaagaaa    720
attgtgccca gggattgtgg ttgtaagcct tgcatatgta cagtcccaga agtatcatct    780
gtcttcatct tccccccaaa gcccaaggat gtgctcacca ttactctgac tcctaaggtc    840
acgtgtgttg tggtagacat cagcaaggat gatcccgagg tccagttcag ctggtttgta    900
gatgatgtgg aggtgcacac agctcagacg caaccccggg aggagcagtt caacagcact    960
ttccgctcag tcagtgaact tcccatcatg caccaggact ggctcaatgg caaggagttc   1020
aaatgcaggg tcaacagtgc agctttccct gcccccatcg agaaaaccat ctccaaaacc   1080
aaaggcagac cgaaggctcc acaggtgtac accattccac ctcccaagga gcagatggcc   1140
aaggataaag tcagtctgac ctgcatgata acagacttct tccctgaaga cattactgtg   1200
gagtggcagt ggaatgggca gccagcgag aactacaaga acactcagcc catcatggac    1260
acagatggct cttacttcgt ctacagcaag ctcaatgtgc agaagagcaa ctgggaggca   1320
```
ggaaatactt tcacctgctc tgtgttacat gagggcctgc acaaccacca tactgagaag    1380
agcctctccc actctcctgg taaatga                                        1407

<210> SEQ ID NO 42
<211> LENGTH: 468
<212> TYPE: PRT
<213> ORGANISM: Artificial Sequence
<220> FEATURE:
<223> OTHER INFORMATION: mAb28 heavy chain

<400> SEQUENCE: 42

Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Val Lys Gln Ala Pro Gly
    50                  55                  60

Lys Asp Leu Lys Trp Met Gly Trp Ile Asn Thr Tyr Ser Gly Met Ser
65                  70                  75                  80

Thr Tyr Ala Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Met Ala Thr Tyr Phe Cys Ala Arg Ser Arg Ile Thr Thr Met Gly Gly
        115                 120                 125

Tyr Ala Met Asp Tyr Trp Gly Gln Gly Ala Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro

```
               340                 345                 350
Ile Glu Lys Thr Ile Ser Lys Thr Lys Gly Arg Pro Lys Ala Pro Gln
            355                 360                 365

Val Tyr Thr Ile Pro Pro Lys Glu Gln Met Ala Lys Asp Lys Val
        370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
450                 455                 460

Ser Pro Gly Lys
465

<210> SEQ ID NO 43
<211> LENGTH: 7
<212> TYPE: PRT
<213> ORGANISM: Artificial Sequence
<220> FEATURE:
<223> OTHER INFORMATION: mAb28 heavy chain CDR1

<400> SEQUENCE: 43

Gly Tyr Thr Phe Thr Asn Tyr
1               5

<210> SEQ ID NO 44
<211> LENGTH: 6
<212> TYPE: PRT
<213> ORGANISM: Artificial Sequence
<220> FEATURE:
<223> OTHER INFORMATION: mAb28 heavy chain CDR2

<400> SEQUENCE: 44

Asn Thr Tyr Ser Gly Met
1               5

<210> SEQ ID NO 45
<211> LENGTH: 13
<212> TYPE: PRT
<213> ORGANISM: Artificial Sequence
<220> FEATURE:
<223> OTHER INFORMATION: mAb28 heavy chain CDR3

<400> SEQUENCE: 45

Ser Arg Ile Thr Thr Met Gly Gly Tyr Ala Met Asp Tyr
1               5                   10

<210> SEQ ID NO 46
<211> LENGTH: 726
<212> TYPE: DNA
<213> ORGANISM: Artificial Sequence
<220> FEATURE:
<223> OTHER INFORMATION: mAb28 light chain

<400> SEQUENCE: 46
atggacatga gggtgcccgc tcagctcctg gggctcctgc tgctgtggct gagaggtgcg      60
cgctgtgaag ttgtgatgac ccaaactcca ctctcccctgc ctgtcagtct tggagatcaa    120
```

```
gcctccatct cttgcagatc tagtcagagc cttgtacaca gtaatggaaa cacctattta        180
cattggtacc tgcagaagcc aggccagtct ccaaagctcc tgatctccaa agtttccaac        240 cgatttctg gggtcccaga caggttcagt ggcagtggat cagggacaga tttcacactc         300
aagatcatca gagtggaggc tgaggatctg ggagtttatt tctgctctca aaatacacat        360
gttccgtgga cgttcggtgg aggcaccaag ctggaaatca aacgtgcaga tgctgcgcca        420
actgtatcca tcttcccacc atctagcgag cagttaacat ctggaggtgc ctcagtcgtg        480
tgcttcttga acaacttcta ccccaaagac atcaatgtca agtggaagat tgatggcagt        540
gaacgacaaa atggcgtcct gaacagttgg actgatcagg acagcaaaga cagcacctac        600
agcatgagca gcaccctcac gttgaccaag gacgagtatg aacgacataa cagctatacc        660
tgtgaggcca ctcacaagac atcaacttca cccattgtca agagcttcaa caggaatgag        720
tgttag                                                                   726
```

<210> SEQ ID NO 47
<211> LENGTH: 241
<212> TYPE: PRT
<213> ORGANISM: Artificial Sequence
<220> FEATURE:
<223> OTHER INFORMATION: mAb28 light chain

<400> SEQUENCE: 47

```
Met Asp Met Arg Val Pro Ala Gln Leu Leu Gly Leu Leu Leu Leu Trp
1               5                   10                  15

Leu Arg Gly Ala Arg Cys Glu Val Val Met Thr Gln Thr Pro Leu Ser
                20                  25                  30

Leu Pro Val Ser Leu Gly Asp Gln Ala Ser Ile Ser Cys Arg Ser Ser
            35                  40                  45

Gln Ser Leu Val His Ser Asn Gly Asn Thr Tyr Leu His Trp Tyr Leu
        50                  55                  60

Gln Lys Pro Gly Gln Ser Pro Lys Leu Leu Ile Ser Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ile Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys
```

<210> SEQ ID NO 48
<211> LENGTH: 16
<212> TYPE: PRT
<213> ORGANISM: Artificial Sequence
<220> FEATURE:
<223> OTHER INFORMATION: mAb28 light chain CDR1

<400> SEQUENCE: 48

Arg Ser Ser Gln Ser Leu Val His Ser Asn Gly Asn Thr Tyr Leu His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: mAb28 light chain CDR2

<400> SEQUENCE: 49

Lys Val Ser Asn Arg Phe Ser
1               5

<210> SEQ ID NO 50
<211> LENGTH: 9
<212> TYPE: PRT
<213> ORGANISM: Artificial Sequence
<220> FEATURE:
<223> OTHER INFORMATION: mAb28 light chain CDR3

<400> SEQUENCE: 50

Ser Gln Asn Thr His Val Pro Trp Thr
1               5

<210> SEQ ID NO 51
<211> LENGTH: 1389
<212> TYPE: DNA
<213> ORGANISM: Artificial Sequence
<220> FEATURE:
<223> OTHER INFORMATION: mAb39 heavy chain

<400> SEQUENCE: 51
atgggatgga gctgtatcat gttcttttg gtagcaacag ctacagatgt ccactcccag      60
gtccaactgc agcagcctgg ggctgaactg gtgaagcctg gggcttcagt gaagctgtcc    120
tgcaaggctt ctggctactc cttcaccacc tactggatgc actgggtgaa gcagaggcct    180
ggacaaggcc tagagtgggt tggagatatt aatcctagga acgtcgtac taactacaat    240 gagaagtcca agagcaaggc cacactgact gtagacatat catccagcac agtatacatg    300
caagtcagca gcctgacatc tgaggactct gcggtctatt actgtgcaat atggtcgggt    360
gctatggact actggggtcc aggaaccctca gtcaccgtct cctcagccaa aacaacagcc    420
ccatcggtct atccactggc ccctgtgtgt ggagatacaa ctggctcctc ggtgactcta    480
ggatgcctgg tcaagggtta tttcccctgag ccagtgacct tgacctggaa ctctggatcc    540
ctgtccagtg atgtgcacac cttcccagct ctcctgcagt ctggcctcta caccctcagc    600
agctcagtga ctgtaaccac ctggcccagc cagaccatca cctgcaatgt ggcccacccg    660
gcaagcagca ccaaagtgga caagaaaatt gagcccagag gtccccaac acataaaccc    720 tgtcctccat gcccagctcc taacctcttg ggtggaccat ccgtcttcat cttccctcca    780
aagatcaagg atgtactcat gatctccctg agcccatgg tcacgtgtgt ggtggtggat    840
gtgagcgagg atgacccaga tgtccatgtc agctggttcg tgaacaacgt ggaagtacac    900

```
acagctcaga cacaaaccca tagagaggat tacaacagta ctatccgggt ggtcagtgcc    960
ctccccatcc agcaccagga ctggatgagt ggcaaggagt tcaaatgcaa ggtcaacaac   1020
aaagccctcc cagcgcccat cgagagaacc atctcaaaac ccaagggcc  agtaagagct   1080 ccacaggtat atgtcttgcc tccaccagaa gaagagatga ctaagaaaca ggtcactctg   1140
acctgcatga tcacagactt catgcctgaa gacatttacg tggagtggac caacaacggg   1200
caaacagagc taaactacaa gaacactgaa ccagtcctgg actctgatgg ttcttacttc   1260
atgtacagca agctgagagt ggaaaagaag aactgggtgg aaagaaatag ctactcctgt   1320
tcagtggtcc acgagggtct gcacaatcac cacacgacta gagcttctc  ccggtctccg   1380 ggtaaatga                                                          1389
```

<210> SEQ ID NO 52
<211> LENGTH: 462
<212> TYPE: PRT
<213> ORGANISM: Artificial Sequence
<220> FEATURE:
<223> OTHER INFORMATION: mAb39 heavy chain

<400> SEQUENCE: 52

```
Met Gly Trp Ser Cys Ile Met Phe Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Ser Phe
        35                  40                  45

Thr Thr Tyr Trp Met His Trp Val Lys Gln Arg Pro Gly Gln Gly Leu
    50                  55                  60

Glu Trp Val Gly Asp Ile Asn Pro Arg Asn Gly Arg Thr Asn Tyr Asn
65                  70                  75                  80

Glu Lys Ser Lys Ser Lys Ala Thr Leu Thr Val Asp Ile Ser Ser Ser
                85                  90                  95

Thr Val Tyr Met Gln Val Ser Ser Leu Thr Ser Glu Asp Ser Ala Val
            100                 105                 110

Tyr Tyr Cys Ala Ile Trp Ser Gly Ala Met Asp Tyr Trp Gly Pro Gly
        115                 120                 125

Thr Ser Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Asp Val His Thr Phe Pro Ala Leu Leu
            180                 185                 190

Gln Ser Gly Leu Tyr Thr Leu Ser Ser Ser Val Thr Val Thr Thr Trp
        195                 200                 205

Pro Ser Gln Thr Ile Thr Cys Asn Val Ala His Pro Ala Ser Ser Thr
    210                 215                 220

Lys Val Asp Lys Lys Ile Glu Pro Arg Gly Ser Pro Thr His Lys Pro
225                 230                 235                 240

Cys Pro Pro Cys Pro Ala Pro Asn Leu Leu Gly Gly Pro Ser Val Phe
                245                 250                 255

Ile Phe Pro Pro Lys Ile Lys Asp Val Leu Met Ile Ser Leu Ser Pro
            260                 265                 270
```

```
Met Val Thr Cys Val Val Asp Val Ser Glu Asp Pro Asp Val
            275                 280                 285

His Val Ser Trp Phe Val Asn Asn Val Glu Val His Thr Ala Gln Thr
        290                 295                 300

Gln Thr His Arg Glu Asp Tyr Asn Ser Thr Ile Arg Val Val Ser Ala
305                 310                 315                 320

Leu Pro Ile Gln His Gln Asp Trp Met Ser Gly Lys Glu Phe Lys Cys
                325                 330                 335

Lys Val Asn Asn Lys Ala Leu Pro Ala Pro Ile Glu Arg Thr Ile Ser
                340                 345                 350

Lys Pro Lys Gly Pro Val Arg Ala Pro Gln Val Tyr Val Leu Pro Pro
                355                 360                 365

Pro Glu Glu Glu Met Thr Lys Lys Gln Val Thr Leu Thr Cys Met Ile
        370                 375                 380

Thr Asp Phe Met Pro Glu Asp Ile Tyr Val Glu Trp Thr Asn Asn Gly
385                 390                 395                 400

Gln Thr Glu Leu Asn Tyr Lys Asn Thr Glu Pro Val Leu Asp Ser Asp
                405                 410                 415

Gly Ser Tyr Phe Met Tyr Ser Lys Leu Arg Val Glu Lys Lys Asn Trp
                420                 425                 430

Val Glu Arg Asn Ser Tyr Ser Cys Ser Val Val His Glu Gly Leu His
                435                 440                 445

Asn His His Thr Thr Lys Ser Phe Ser Arg Ser Pro Gly Lys
        450                 455                 460

<210> SEQ ID NO 53
<211> LENGTH: 7
<212> TYPE: PRT
<213> ORGANISM: Artificial Sequence
<220> FEATURE:
<223> OTHER INFORMATION: mAb39 heavy chain CDR1

<400> SEQUENCE: 53

Gly Tyr Ser Phe Thr Thr Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: mAb39 heavy chain CDR2

<400> SEQUENCE: 54

Asn Pro Arg Asn Gly Arg
1               5

<210> SEQ ID NO 55
<211> LENGTH: 7
<212> TYPE: PRT
<213> ORGANISM: Artificial Sequence
<220> FEATURE:
<223> OTHER INFORMATION: mAb39 heavy chain CDR3

<400> SEQUENCE: 55

Trp Ser Gly Ala Met Asp Tyr
1               5

<210> SEQ ID NO 56
<211> LENGTH: 717
<212> TYPE: DNA
```

<213> ORGANISM: Artificial Sequence
<220> FEATURE:
<223> OTHER INFORMATION: mAb39 light chain

<400> SEQUENCE: 56

```
atgaagttgc ctgttaggct gttggtgctg atgttctgga ttcctgcttc cagcagtgat      60
gttgtgatga cccaaactcc actctccctg cctgtcagtc ttggagatca accctccatc     120
tcttgcaaat ctagtcagag ccttgtacac aataatggaa acacctattt acattggtac     180
ctgcagaagc caggccagtc tccaaagctc ctgatctaca agtttccaa ccgatttct      240
ggggtcccag acaggttcag tggcagtgga tcagggacag atttcacact caagatcagc     300
agagtggagg ctgaggatct gggagtttat ttctgctctc aaactacaca tgttcctccg     360
acgttcggtg aggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660
actcacaaga catcaacttc acccattgtc aagagcttca caggggaga gtgttga         717
```

<210> SEQ ID NO 57
<211> LENGTH: 238
<212> TYPE: PRT
<213> ORGANISM: Artificial Sequence
<220> FEATURE:
<223> OTHER INFORMATION: mAb39 light chain

<400> SEQUENCE: 57

```
Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Pro Ser Ile Ser Cys Lys Ser Ser Gln Ser Leu
        35                  40                  45

Val His Asn Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Thr Thr His Val Pro Pro Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205
```

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Gly Glu Cys
225                 230                 235

<210> SEQ ID NO 58
<211> LENGTH: 16
<212> TYPE: PRT
<213> ORGANISM: Artificial Sequence
<220> FEATURE:
<223> OTHER INFORMATION: mAb39 light chain CDR1

<400> SEQUENCE: 58

Lys Ser Ser Gln Ser Leu Val His Asn Asn Gly Asn Thr Tyr Leu His
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: mAb39 light chain CDR2

<400> SEQUENCE: 59

Lys Val Ser Asn Arg Phe Ser
1               5

<210> SEQ ID NO 60
<211> LENGTH: 9
<212> TYPE: PRT
<213> ORGANISM: Artificial Sequence
<220> FEATURE:
<223> OTHER INFORMATION: mAb39 light chain CDR3

<400> SEQUENCE: 60

Ser Gln Thr Thr His Val Pro Pro Thr
1               5

<210> SEQ ID NO 61
<211> LENGTH: 1389
<212> TYPE: DNA
<213> ORGANISM: Artificial Sequence
<220> FEATURE:
<223> OTHER INFORMATION: mAb39 heavy chain v2 (t1375a-->S459T)

<400> SEQUENCE: 61
atgggatgga gctgtatcat gttcttttg gtagcaacag ctacagatgt ccactcccag      60
gtccaactgc agcagcctgg ggctgaactg gtgaagcctg ggcttcagt gaagctgtcc     120 tgcaaggctt ctggctactc cttcaccacc tactggatgc actgggtgaa gcagaggcct     180
ggacaaggcc tagagtgggt tggagatatt aatcctagga cggtcgtac taactacaat     240 gagaagtcca agagcaaggc cacactgact gtagacatat catccagcac agtatacatg     300
caagtcagca gcctgacatc tgaggactct gcggtctatt actgtgcaat atggtcgggt     360
gctatggact actgggtcc aggaacctca gtcaccgtct cctcagccaa aacaacagcc     420
ccatcggtct atccactggc ccctgtgtgt ggagatacaa ctggctcctc ggtgactcta     480
ggatgcctgg tcaagggtta tttccctgag ccagtgacct tgacctggaa ctctggatcc     540
ctgtccagtg atgtgcacac cttcccagct ctcctgcagt ctggcctcta cacactcagc     600
agctcagtga ctgtaaccac ctggcccagc cagaccatca cctgcaatgt ggcccacccg     660
gcaagcagca ccaaagtgga caagaaaatt gagcccagag ggtccccaac acataaaccc     720

```
tgtcctccat gcccagctcc taacctcttg ggtggaccat ccgtcttcat cttccctcca    780
aagatcaagg atgtactcat gatctccctg agccccatgg tcacgtgtgt ggtggtggat    840
gtgagcgagg atgacccaga tgtccatgtc agctggttcg tgaacaacgt ggaagtacac    900
acagctcaga cacaaaccca tagagaggat tacaacagta ctatccgggt ggtcagtgcc    960
ctccccatcc agcaccagga ctggatgagt ggcaaggagt tcaaatgcaa ggtcaacaac   1020
aaagccctcc cagcgcccat cgagagaacc atctcaaaac ccaagggcc agtaagagct    1080 ccacaggtat atgtcttgcc tccaccagaa gaagagatga ctaagaaaca ggtcactctg    1140
acctgcatga tcacagactt catgcctgaa gacatttacg tggagtggac caacaacggg    1200
caaacagagc taaactacaa gaacactgaa ccagtcctgg actctgatgg ttcttacttc    1260
atgtacagca agctgagagt ggaaaagaag aactgggtgg aaagaaatag ctactcctgt    1320
tcagtggtcc acgagggtct gcacaatcac cacacgacta gagcttctc ccggactccg    1380 ggtaaatga                                                            1389
```

<210> SEQ ID NO 62
<211> LENGTH: 462
<212> TYPE: PRT
<213> ORGANISM: Artificial Sequence
<220> FEATURE:
<223> OTHER INFORMATION: mAb39 heavy chain (S459T)

<400> SEQUENCE: 62

```
Met Gly Trp Ser Cys Ile Met Phe Phe Leu Val Ala Thr Ala Thr Asp
1               5                   10                  15

Val His Ser Gln Val Gln Leu Gln Gln Pro Gly Ala Glu Leu Val Lys
                20                  25                  30

Pro Gly Ala Ser Val Lys Leu Ser Cys Lys Ala Ser Gly Tyr Ser Phe
            35                  40                  45

Thr Thr Tyr Trp Met His Trp Val Lys Gln Arg Pro Gly Gln Gly Leu
        50                  55                  60

Glu Trp Val Gly Asp Ile Asn Pro Arg Asn Gly Arg Thr Asn Tyr Asn
65                  70                  75                  80

Glu Lys Ser Lys Ser Lys Ala Thr Leu Thr Val Asp Ile Ser Ser Ser
                85                  90                  95

Thr Val Tyr Met Gln Val Ser Ser Leu Thr Ser Glu Asp Ser Ala Val
            100                 105                 110

Tyr Tyr Cys Ala Ile Trp Ser Gly Ala Met Asp Tyr Trp Gly Pro Gly
        115                 120                 125

Thr Ser Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Asp Val His Thr Phe Pro Ala Leu Leu
            180                 185                 190

Gln Ser Gly Leu Tyr Thr Leu Ser Ser Ser Val Thr Val Thr Thr Trp
        195                 200                 205

Pro Ser Gln Thr Ile Thr Cys Asn Val Ala His Pro Ala Ser Ser Thr
    210                 215                 220

Lys Val Asp Lys Lys Ile Glu Pro Arg Gly Ser Pro Thr His Lys Pro
225                 230                 235                 240
```

```
Cys Pro Pro Cys Pro Ala Pro Asn Leu Leu Gly Gly Pro Ser Val Phe
            245             250             255

Ile Phe Pro Pro Lys Ile Lys Asp Val Leu Met Ile Ser Leu Ser Pro
        260             265             270

Met Val Thr Cys Val Val Val Asp Val Ser Glu Asp Pro Asp Val
        275             280             285

His Val Ser Trp Phe Val Asn Asn Val Glu Val His Thr Ala Gln Thr
    290             295             300

Gln Thr His Arg Glu Asp Tyr Asn Ser Thr Ile Arg Val Val Ser Ala
305             310             315             320

Leu Pro Ile Gln His Gln Asp Trp Met Ser Gly Lys Glu Phe Lys Cys
            325             330             335

Lys Val Asn Asn Lys Ala Leu Pro Ala Pro Ile Glu Arg Thr Ile Ser
            340             345             350

Lys Pro Lys Gly Pro Val Arg Ala Pro Gln Val Tyr Val Leu Pro Pro
            355             360             365

Pro Glu Glu Glu Met Thr Lys Lys Gln Val Thr Leu Thr Cys Met Ile
    370             375             380

Thr Asp Phe Met Pro Glu Asp Ile Tyr Val Glu Trp Thr Asn Asn Gly
385             390             395             400

Gln Thr Glu Leu Asn Tyr Lys Asn Thr Glu Pro Val Leu Asp Ser Asp
            405             410             415

Gly Ser Tyr Phe Met Tyr Ser Lys Leu Arg Val Glu Lys Lys Asn Trp
            420             425             430

Val Glu Arg Asn Ser Tyr Ser Cys Ser Val Val His Glu Gly Leu His
        435             440             445

Asn His His Thr Thr Lys Ser Phe Ser Arg Thr Pro Gly Lys
    450             455             460
```